(12) United States Patent
Pötter et al.

(10) Patent No.: US 12,146,167 B2
(45) Date of Patent: Nov. 19, 2024

(54) ENZYMATIC METHOD FOR PRODUCING L-GLUFOSINATE AND ITS PHOSPHOESTERS

(71) Applicant: Evonik Operations GmbH, Essen (DE)

(72) Inventors: Markus Pötter, Muenster (DE); Ludger Lautenschütz, Hanau (DE); Daniel Fischer, Hanau (DE); Jakob Müller, Haltern am See (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 18/553,072

(22) PCT Filed: Mar. 28, 2022

(86) PCT No.: PCT/EP2022/058082
§ 371 (c)(1),
(2) Date: Sep. 28, 2023

(87) PCT Pub. No.: WO2022/207543
PCT Pub. Date: Oct. 6, 2022

(65) Prior Publication Data
US 2024/0117327 A1    Apr. 11, 2024

(30) Foreign Application Priority Data
Apr. 1, 2021   (EP) .................................... 21166546

(51) Int. Cl.
*C12N 9/88*    (2006.01)
*C12N 9/00*    (2006.01)
(Continued)

(52) U.S. Cl.
CPC ............. *C12N 9/1085* (2013.01); *C12N 9/88* (2013.01); *C12N 9/93* (2013.01); *C12P 13/04* (2013.01);
(Continued)

(58) Field of Classification Search
CPC .......... C12N 9/88; C12N 9/93; C12N 9/1085; C12P 13/04
See application file for complete search history.

(56) References Cited

U.S. PATENT DOCUMENTS

| 5,442,088 A | 8/1995 | Hoffmann |
| 6,359,162 B1 | 3/2002 | Willms |

(Continued)

FOREIGN PATENT DOCUMENTS

| CN | 106083922 | 11/2016 |
| CN | 108516991 | 9/2018 |

(Continued)

OTHER PUBLICATIONS

Fransceus. J Ind Microbiol Biotechnol. May 2017;44(4-5):687-695.*

(Continued)

*Primary Examiner* — Yong D Pak
(74) *Attorney, Agent, or Firm* — Grüneberg and Myers PLLC

(57) ABSTRACT

An enzymatically catalyzed method for producing L-glufosinate or a phosphoester of L-glufosinate can be performed. An activated L-homoserine $H_A$ is reacted with a substrate S selected from methylphosphinic acid and the esters of methylphosphinic acid. The method makes accessible new substrates in the enzymatic production of L-glufosinate and its phosphoesters.

11 Claims, 4 Drawing Sheets

Figure 1:
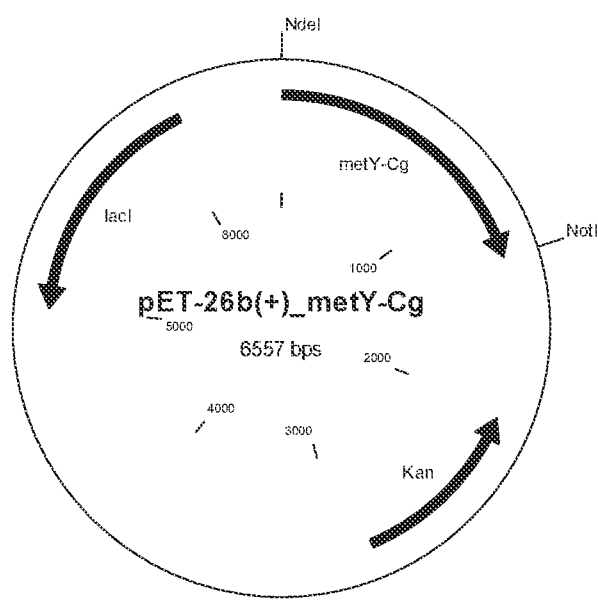

Specification includes a Sequence Listing.

(51) Int. Cl.
  *C12N 9/10* (2006.01)
  *C12P 13/04* (2006.01)
(52) U.S. Cl.
  CPC ................ *C12Y 205/01048* (2013.01); *C12Y 205/01049* (2013.01)

(56) References Cited

U.S. PATENT DOCUMENTS

| | | | |
|---|---|---|---|
| 6,812,016 B2 * | 11/2004 | Moeckel | ............... C12P 13/12 435/6.15 |
| 10,800,736 B2 | 10/2020 | Fischer et al. | |
| 10,815,508 B2 | 10/2020 | Skerra et al. | |
| 10,899,706 B2 | 1/2021 | Hierold et al. | |
| 11,034,985 B2 | 6/2021 | Ochrombel et al. | |
| 11,306,334 B2 | 4/2022 | Haas et al. | |
| 2010/0184164 A1 | 7/2010 | Kim et al. | |
| 2012/0123158 A1 | 5/2012 | Kim et al. | |
| 2013/0273615 A1 | 10/2013 | Kim et al. | |
| 2017/0051323 A1 | 2/2017 | Ochrombel et al. | |
| 2017/0253897 A1 | 9/2017 | Green et al. | |
| 2018/0298410 A1 | 10/2018 | Skerra et al. | |
| 2018/0346946 A1 | 12/2018 | Ochrombel et al. | |
| 2020/0024624 A1 | 1/2020 | Haas et al. | |
| 2020/0115334 A1 | 4/2020 | Hierold et al. | |
| 2020/0157045 A1 | 5/2020 | Fischer et al. | |
| 2020/0181179 A1 | 6/2020 | Fields et al. | |
| 2021/0214754 A1 | 7/2021 | Green et al. | |
| 2022/0024955 A1 | 1/2022 | Jeon et al. | |
| 2022/0306658 A1 | 9/2022 | Jeon et al. | |

FOREIGN PATENT DOCUMENTS

| | | |
|---|---|---|
| EP | 0508296 | 10/1992 |
| EP | 2402453 | 1/2012 |
| EP | 2657250 | 10/2013 |
| EP | 2657345 | 10/2013 |
| EP | 4151643 | 3/2023 |
| WO | 1999/009039 | 2/1999 |
| WO | 02/18613 | 3/2002 |
| WO | 2015/165746 | 11/2015 |
| WO | 2017/151573 | 9/2017 |
| WO | 2019/018406 | 1/2019 |
| WO | 2020/051188 | 3/2020 |
| WO | 2020/145513 | 7/2020 |
| WO | 2020/145514 | 7/2020 |
| WO | 2020/145627 | 7/2020 |
| WO | 2022/248739 | 12/2022 |
| WO | 2023/174511 | 9/2023 |
| WO | 2023/222226 | 11/2023 |
| WO | 2023/222227 | 11/2023 |
| WO | 2023/232225 | 12/2023 |
| WO | 2024/061455 | 3/2024 |
| WO | 2024/061456 | 3/2024 |

OTHER PUBLICATIONS

Sanavia. Computational and Structural Biotechnology Journal, vol. 18, 2020, pp. 1968-1979.*
Studer. Residue mutations and their impact on protein structure and function: detecting beneficial and pathogenic changes. Biochem. J. (2013) 449, 581-594.*
U.S. Appl. No. 18/569,989, filed Dec. 13, 2023, Lautenschütz et al.
Clausen et al., "Crystal structure of *Escherichia coli* cystathionine γ-synthase at 1.5 Å resolution", The EMBO Journal, vol. 17, No. 23, 1998, pp. 6827-6838.
Ferla et al., "Bacterial methionine biosynthesis", Microbiology, vol. 160, 2014, pp. 1571-1584.
Gerhard Hoerlein, "Glufosinate (Phosphinothricin), A Natural Amino Acid with Unexpected Herbicidal Properties", Reviews of Environmental Contamination and Toxicology, vol. 138, 1994, pp. 73-145.
Karl-Josef Haack, "Synthese-Entwicklung unter speziellen Randbedingungen", Chem. Unserer Zeit, vol. 37, 2003, pp. 128-138 with partial English translation of pp. 128 to 130.
International Search Report dated Jun. 27, 2022, in PCT/EP2022/058082, 5 pages.
Written Opinion dated Jun. 27, 2022, in PCT/EP2022/058082, 6 pages.

* cited by examiner ns

SEQUENCE LISTING

<160> NUMBER OF SEQ ID NOS: 34

<210> SEQ ID NO 1
<211> LENGTH: 1314
<212> TYPE: DNA
<213> ORGANISM: Corynebacterium glutamicum
<220> FEATURE:
<221> NAME/KEY: misc_feature
<222> LOCATION: 1..1314
<223> OTHER INFORMATION: Corynebacterium glutamicum ATCC 13032 (strain)
<220> FEATURE:
<221> NAME/KEY: CDS
<222> LOCATION: 1..1314
<223> OTHER INFORMATION: /note="nucleotide sequence comprising locus_tag
    NCgl0625 disclosed in NC_003450"
    /transl_table=11
<220> FEATURE:
<221> NAME/KEY: misc_feature
<222> LOCATION: 1..1314
<223> OTHER INFORMATION: /gene="metY from Corynebacterium glutamicum
    ATCC 13032"

<400> SEQUENCE: 1

```
atg cca aag tac gac aat tcc aat gct gac cag tgg ggc ttt gaa acc        48
Met Pro Lys Tyr Asp Asn Ser Asn Ala Asp Gln Trp Gly Phe Glu Thr
1               5                   10                  15 cgc tcc att cac gca ggc cag tca gta gac gca cag acc agc gca cga        96
Arg Ser Ile His Ala Gly Gln Ser Val Asp Ala Gln Thr Ser Ala Arg
            20                  25                  30 aac ctt ccg atc tac caa tcc acc gct ttc gtg ttc gac tcc gct gag       144
Asn Leu Pro Ile Tyr Gln Ser Thr Ala Phe Val Phe Asp Ser Ala Glu
        35                  40                  45 cac gcc aag cag cgt ttc gca ctt gag gat cta ggc cct gtt tac tcc       192
His Ala Lys Gln Arg Phe Ala Leu Glu Asp Leu Gly Pro Val Tyr Ser
    50                  55                  60 cgc ctc acc aac cca acc gtt gag gct ttg gaa aac cgc atc gct tcc       240
Arg Leu Thr Asn Pro Thr Val Glu Ala Leu Glu Asn Arg Ile Ala Ser
65                  70                  75                  80 ctc gaa ggt ggc gtc cac gct gta gcg ttc tcc tcc gga cag gcc gca       288
Leu Glu Gly Gly Val His Ala Val Ala Phe Ser Ser Gly Gln Ala Ala
                85                  90                  95 acc acc aac gcc att ttg aac ctg gca gga gcg ggc gac cac atc gtc       336
Thr Thr Asn Ala Ile Leu Asn Leu Ala Gly Ala Gly Asp His Ile Val
            100                 105                 110 acc tcc cca cgc ctc tac ggt ggc acc gag act cta ttc ctt atc act       384
Thr Ser Pro Arg Leu Tyr Gly Gly Thr Glu Thr Leu Phe Leu Ile Thr
        115                 120                 125 ctt aac cgc ctg ggt atc gat gtt tcc ttc gtg gaa aac ccc gac gac       432
Leu Asn Arg Leu Gly Ile Asp Val Ser Phe Val Glu Asn Pro Asp Asp
    130                 135                 140 cct gag tcc tgg cag gca gcc gtt cag cca aac acc aaa gca ttc ttc       480
Pro Glu Ser Trp Gln Ala Ala Val Gln Pro Asn Thr Lys Ala Phe Phe
145                 150                 155                 160 ggc gag act ttc gcc aac cca cag gca gac gtc ctg gat att cct gcg       528
Gly Glu Thr Phe Ala Asn Pro Gln Ala Asp Val Leu Asp Ile Pro Ala
                165                 170                 175 gtg gct gaa gtt gcg cac cgc aac agc gtt cca ctg atc atc gac aac       576
Val Ala Glu Val Ala His Arg Asn Ser Val Pro Leu Ile Ile Asp Asn
            180                 185                 190 acc atc gct acc gca gcg ctc gtg cgc ccg ctc gag ctc ggc gca gac       624
Thr Ile Ala Thr Ala Ala Leu Val Arg Pro Leu Glu Leu Gly Ala Asp
        195                 200                 205 gtt gtc gtc gct tcc ctc acc aag ttc tac acc ggc aac ggc tcc gga       672
Val Val Val Ala Ser Leu Thr Lys Phe Tyr Thr Gly Asn Gly Ser Gly
```

```
ctg ggc ggc gtg ctt atc gac ggc gga aag ttc gat tgg act gtc gaa      720
Leu Gly Gly Val Leu Ile Asp Gly Gly Lys Phe Asp Trp Thr Val Glu
225                 230                 235                 240 aag gat gga aag cca gta ttc ccc tac ttc gtc act cca gat gct gct      768
Lys Asp Gly Lys Pro Val Phe Pro Tyr Phe Val Thr Pro Asp Ala Ala
                245                 250                 255 tac cac gga ttg aag tac gca gac ctt ggt gca cca gcc ttc ggc ctc      816
Tyr His Gly Leu Lys Tyr Ala Asp Leu Gly Ala Pro Ala Phe Gly Leu
            260                 265                 270 aag gtt cgc gtt ggc ctt cta cgc gac acc ggc tcc acc ctc tcc gca      864
Lys Val Arg Val Gly Leu Leu Arg Asp Thr Gly Ser Thr Leu Ser Ala
        275                 280                 285 ttc aac gca tgg gct gca gtc cag ggc atc gac acc ctt tcc ctg cgc      912
Phe Asn Ala Trp Ala Ala Val Gln Gly Ile Asp Thr Leu Ser Leu Arg
    290                 295                 300 ctg gag cgc cac aac gaa aac gcc atc aag gtt gca gaa ttc ctc aac      960
Leu Glu Arg His Asn Glu Asn Ala Ile Lys Val Ala Glu Phe Leu Asn
305                 310                 315                 320 aac cac gag aag gtg gaa aag gtt aac ttc gca ggc ctg aag gat tcc     1008
Asn His Glu Lys Val Glu Lys Val Asn Phe Ala Gly Leu Lys Asp Ser
                325                 330                 335 cct tgg tac gca acc aag gaa aag ctt ggc ctg aag tac acc ggc tcc     1056
Pro Trp Tyr Ala Thr Lys Glu Lys Leu Gly Leu Lys Tyr Thr Gly Ser
            340                 345                 350 gtt ctc acc ttc gag atc aag ggc ggc aag gat gag gct tgg gca ttt     1104
Val Leu Thr Phe Glu Ile Lys Gly Gly Lys Asp Glu Ala Trp Ala Phe
        355                 360                 365 atc gac gcc ctg aag cta cac tcc aac ctt gca aac atc ggc gat gtt     1152
Ile Asp Ala Leu Lys Leu His Ser Asn Leu Ala Asn Ile Gly Asp Val
    370                 375                 380 cgc tcc ctc gtt gtt cac cca gca acc acc acc cat tca cag tcc gac     1200
Arg Ser Leu Val Val His Pro Ala Thr Thr Thr His Ser Gln Ser Asp
385                 390                 395                 400 gaa gct ggc ctg gca cgc gcg ggc gtt acc cag tcc acc gtc cgc ctg     1248
Glu Ala Gly Leu Ala Arg Ala Gly Val Thr Gln Ser Thr Val Arg Leu
                405                 410                 415 tcc gtt ggc atc gag acc att gat gat atc atc gct gac ctc gaa ggc     1296
Ser Val Gly Ile Glu Thr Ile Asp Asp Ile Ile Ala Asp Leu Glu Gly
            420                 425                 430 ggc ttt gct gca atc tag                                              1314
Gly Phe Ala Ala Ile
        435

<210> SEQ ID NO 2
<211> LENGTH: 437
<212> TYPE: PRT
<213> ORGANISM: Corynebacterium glutamicum
<220> FEATURE:
<221> NAME/KEY: misc_feature
<222> LOCATION: 1..437
<223> OTHER INFORMATION: Corynebacterium glutamicum ATCC 13032 (strain)
<220> FEATURE:
<223> OTHER INFORMATION: [CDS]:1..1314 from SEQ ID NO 1

<400> SEQUENCE: 2

Met Pro Lys Tyr Asp Asn Ser Asn Ala Asp Gln Trp Gly Phe Glu Thr
1               5                   10                  15

Arg Ser Ile His Ala Gly Gln Ser Val Asp Ala Gln Thr Ser Ala Arg
            20                  25                  30

Asn Leu Pro Ile Tyr Gln Ser Thr Ala Phe Val Phe Asp Ser Ala Glu
```

```
                35                  40                  45
    His Ala Lys Gln Arg Phe Ala Leu Glu Asp Leu Gly Pro Val Tyr Ser
    50                  55                  60

Arg Leu Thr Asn Pro Thr Val Glu Ala Leu Glu Asn Arg Ile Ala Ser
65                  70                  75                  80

Leu Glu Gly Gly Val His Ala Val Ala Phe Ser Ser Gly Gln Ala Ala
                    85                  90                  95

Thr Thr Asn Ala Ile Leu Asn Leu Ala Gly Ala Gly Asp His Ile Val
                100                 105                 110

Thr Ser Pro Arg Leu Tyr Gly Gly Thr Glu Thr Leu Phe Leu Ile Thr
                115                 120                 125

Leu Asn Arg Leu Gly Ile Asp Val Ser Phe Val Glu Asn Pro Asp Asp
                130                 135                 140

Pro Glu Ser Trp Gln Ala Ala Val Gln Pro Asn Thr Lys Ala Phe Phe
    145                 150                 155                 160

Gly Glu Thr Phe Ala Asn Pro Gln Ala Asp Val Leu Asp Ile Pro Ala
                    165                 170                 175

Val Ala Glu Val Ala His Arg Asn Ser Val Pro Leu Ile Ile Asp Asn
                180                 185                 190

Thr Ile Ala Thr Ala Ala Leu Val Arg Pro Leu Glu Leu Gly Ala Asp
                195                 200                 205

Val Val Val Ala Ser Leu Thr Lys Phe Tyr Thr Gly Asn Gly Ser Gly
                210                 215                 220

Leu Gly Gly Val Leu Ile Asp Gly Gly Lys Phe Asp Trp Thr Val Glu
    225                 230                 235                 240

Lys Asp Gly Lys Pro Val Phe Pro Tyr Phe Val Thr Pro Asp Ala Ala
                    245                 250                 255

Tyr His Gly Leu Lys Tyr Ala Asp Leu Gly Ala Pro Ala Phe Gly Leu
                260                 265                 270

Lys Val Arg Val Gly Leu Leu Arg Asp Thr Gly Ser Thr Leu Ser Ala
                275                 280                 285

Phe Asn Ala Trp Ala Ala Val Gln Gly Ile Asp Thr Leu Ser Leu Arg
    290                 295                 300

Leu Glu Arg His Asn Glu Asn Ala Ile Lys Val Ala Glu Phe Leu Asn
    305                 310                 315                 320

Asn His Glu Lys Val Glu Lys Val Asn Phe Ala Gly Leu Lys Asp Ser
                    325                 330                 335

Pro Trp Tyr Ala Thr Lys Glu Lys Leu Gly Leu Lys Tyr Thr Gly Ser
                    340                 345                 350

Val Leu Thr Phe Glu Ile Lys Gly Gly Lys Asp Glu Ala Trp Ala Phe
                    355                 360                 365

Ile Asp Ala Leu Lys Leu His Ser Asn Leu Ala Asn Ile Gly Asp Val
                370                 375                 380

Arg Ser Leu Val Val His Pro Ala Thr Thr Thr His Ser Gln Ser Asp
    385                 390                 395                 400

Glu Ala Gly Leu Ala Arg Ala Gly Val Thr Gln Ser Thr Val Arg Leu
                    405                 410                 415

Ser Val Gly Ile Glu Thr Ile Asp Asp Ile Ile Ala Asp Leu Glu Gly
                420                 425                 430

Gly Phe Ala Ala Ile
                435

<210> SEQ ID NO 3
```

```
<211> LENGTH: 1331
<212> TYPE: DNA
<213> ORGANISM: Corynebacterium glutamicum
<220> FEATURE:
<221> NAME/KEY: misc_feature
<222> LOCATION: 1..1331
<223> OTHER INFORMATION: Corynebacterium glutamicum ATCC 13032 (strain)
<220> FEATURE:
<221> NAME/KEY: misc_feature
<222> LOCATION: 4..9
<223> OTHER INFORMATION: /note="restriction site NdeI"
<220> FEATURE:
<221> NAME/KEY: CDS
<222> LOCATION: 7..1320
<223> OTHER INFORMATION: /transl_table=11
<220> FEATURE:
<221> NAME/KEY: misc_feature
<222> LOCATION: 1321..1328
<223> OTHER INFORMATION: /note="restriction site NotI"

<400> SEQUENCE: 3
```

| | | | | | | | | | | | | | | |
|---|---|---|---|---|---|---|---|---|---|---|---|---|---|---|
| aaacat | atg | cca | aag | tac | gac | aat | tcc | aat | gct | gac | cag | tgg | ggc | ttt | 48 |
| | Met | Pro | Lys | Tyr | Asp | Asn | Ser | Asn | Ala | Asp | Gln | Trp | Gly | Phe | |
| | 1 | | | 5 | | | | | 10 | | | | | | |
| gaa | acc | cgc | tcc | att | cac | gca | ggc | cag | tca | gta | gac | gca | cag | acc | agc | 96 |
| Glu | Thr | Arg | Ser | Ile | His | Ala | Gly | Gln | Ser | Val | Asp | Ala | Gln | Thr | Ser |
| 15 | | | | 20 | | | | | 25 | | | | | 30 | |
| gca | cga | aac | ctt | ccg | atc | tac | caa | tcc | acc | gct | ttc | gtg | ttc | gac | tcc | 144 |
| Ala | Arg | Asn | Leu | Pro | Ile | Tyr | Gln | Ser | Thr | Ala | Phe | Val | Phe | Asp | Ser |
| | | | 35 | | | | | 40 | | | | | 45 | | |
| gct | gag | cac | gcc | aag | cag | cgt | ttc | gca | ctt | gag | gat | cta | ggc | cct | gtt | 192 |
| Ala | Glu | His | Ala | Lys | Gln | Arg | Phe | Ala | Leu | Glu | Asp | Leu | Gly | Pro | Val |
| | | 50 | | | | | 55 | | | | | 60 | | | |
| tac | tcc | cgc | ctc | acc | aac | cca | acc | gtt | gag | gct | ttg | gaa | aac | cgc | atc | 240 |
| Tyr | Ser | Arg | Leu | Thr | Asn | Pro | Thr | Val | Glu | Ala | Leu | Glu | Asn | Arg | Ile |
| 65 | | | | | 70 | | | | | 75 | | | | | |
| gct | tcc | ctc | gaa | ggt | ggc | gtc | cac | gct | gta | gcg | ttc | tcc | tcc | gga | cag | 288 |
| Ala | Ser | Leu | Glu | Gly | Gly | Val | His | Ala | Val | Ala | Phe | Ser | Ser | Gly | Gln |
| 80 | | | | | 85 | | | | | 90 | | | | | |
| gcc | gca | acc | acc | aac | gcc | att | ttg | aac | ctg | gca | gga | gcg | ggc | gac | cac | 336 |
| Ala | Ala | Thr | Thr | Asn | Ala | Ile | Leu | Asn | Leu | Ala | Gly | Ala | Gly | Asp | His |
| 95 | | | | 100 | | | | | 105 | | | | | 110 | |
| atc | gtc | acc | tcc | cca | cgc | ctc | tac | ggt | ggc | acc | gag | act | cta | ttc | ctt | 384 |
| Ile | Val | Thr | Ser | Pro | Arg | Leu | Tyr | Gly | Gly | Thr | Glu | Thr | Leu | Phe | Leu |
| | | | 115 | | | | | 120 | | | | | 125 | | |
| atc | act | ctt | aac | cgc | ctg | ggt | atc | gat | gtt | tcc | ttc | gtg | gaa | aac | ccc | 432 |
| Ile | Thr | Leu | Asn | Arg | Leu | Gly | Ile | Asp | Val | Ser | Phe | Val | Glu | Asn | Pro |
| | | 130 | | | | | 135 | | | | | 140 | | | |
| gac | gac | cct | gag | tcc | tgg | cag | gca | gcc | gtt | cag | cca | aac | acc | aaa | gca | 480 |
| Asp | Asp | Pro | Glu | Ser | Trp | Gln | Ala | Ala | Val | Gln | Pro | Asn | Thr | Lys | Ala |
| | | 145 | | | | | 150 | | | | | 155 | | | |
| ttc | ttc | ggc | gag | act | ttc | gcc | aac | cca | cag | gca | gac | gtc | ctg | gat | att | 528 |
| Phe | Phe | Gly | Glu | Thr | Phe | Ala | Asn | Pro | Gln | Ala | Asp | Val | Leu | Asp | Ile |
| 160 | | | | | 165 | | | | | 170 | | | | | |
| cct | gcg | gtg | gct | gaa | gtt | gcg | cac | cgc | aac | agc | gtt | cca | ctg | atc | atc | 576 |
| Pro | Ala | Val | Ala | Glu | Val | Ala | His | Arg | Asn | Ser | Val | Pro | Leu | Ile | Ile |
| 175 | | | | | 180 | | | | | 185 | | | | | 190 |
| gac | aac | acc | atc | gct | acc | gca | gcg | ctc | gtg | cgc | ccg | ctc | gag | ctc | ggc | 624 |
| Asp | Asn | Thr | Ile | Ala | Thr | Ala | Ala | Leu | Val | Arg | Pro | Leu | Glu | Leu | Gly |
| | | | 195 | | | | | 200 | | | | | 205 | | |
| gca | gac | gtt | gtc | gtc | gct | tcc | ctc | acc | aag | ttc | tac | acc | ggc | aac | ggc | 672 |
| Ala | Asp | Val | Val | Val | Ala | Ser | Leu | Thr | Lys | Phe | Tyr | Thr | Gly | Asn | Gly |
| | | 210 | | | | | 215 | | | | | 220 | | | |
| tcc | gga | ctg | ggc | ggc | gtg | ctt | atc | gac | ggc | gga | aag | ttc | gat | tgg | act | 720 |

```
Ser Gly Leu Gly Gly Val Leu Ile Asp Gly Gly Lys Phe Asp Trp Thr
            225                 230                 235 gtc gaa aag gat gga aag cca gta ttc ccc tac ttc gtc act cca gat       768
Val Glu Lys Asp Gly Lys Pro Val Phe Pro Tyr Phe Val Thr Pro Asp
        240                 245                 250 gct gct tac cac gga ttg aag tac gca gac ctt ggt gca cca gcc ttc       816
Ala Ala Tyr His Gly Leu Lys Tyr Ala Asp Leu Gly Ala Pro Ala Phe
    255                 260                 265                 270 ggc ctc aag gtt cgc gtt ggc ctt cta cgc gac acc ggc tcc acc ctc       864
Gly Leu Lys Val Arg Val Gly Leu Leu Arg Asp Thr Gly Ser Thr Leu
                275                 280                 285 tcc gca ttc aac gca tgg gct gca gtc cag ggc atc gac acc ctt tcc       912
Ser Ala Phe Asn Ala Trp Ala Ala Val Gln Gly Ile Asp Thr Leu Ser
            290                 295                 300 ctg cgc ctg gag cgc cac aac gaa aac gcc atc aag gtt gca gaa ttc       960
Leu Arg Leu Glu Arg His Asn Glu Asn Ala Ile Lys Val Ala Glu Phe
305                 310                 315 ctc aac aac cac gag aag gtg gaa aag gtt aac ttc gca ggc ctg aag      1008
Leu Asn Asn His Glu Lys Val Glu Lys Val Asn Phe Ala Gly Leu Lys
        320                 325                 330 gat tcc cct tgg tac gca acc aag gaa aag ctt ggc ctg aag tac acc      1056
Asp Ser Pro Trp Tyr Ala Thr Lys Glu Lys Leu Gly Leu Lys Tyr Thr
335                 340                 345                 350 ggc tcc gtt ctc acc ttc gag atc aag ggc ggc aag gat gag gct tgg      1104
Gly Ser Val Leu Thr Phe Glu Ile Lys Gly Gly Lys Asp Glu Ala Trp
                355                 360                 365 gca ttt atc gac gcc ctg aag cta cac tcc aac ctt gca aac atc ggc      1152
Ala Phe Ile Asp Ala Leu Lys Leu His Ser Asn Leu Ala Asn Ile Gly
            370                 375                 380 gat gtt cgc tcc ctc gtt gtt cac cca gca acc acc acc cat tca cag      1200
Asp Val Arg Ser Leu Val Val His Pro Ala Thr Thr Thr His Ser Gln
        385                 390                 395 tcc gac gaa gct ggc ctg gca cgc gcg ggc gtt acc cag tcc acc gtc      1248
Ser Asp Glu Ala Gly Leu Ala Arg Ala Gly Val Thr Gln Ser Thr Val
400                 405                 410 cgc ctg tcc gtt ggc atc gag acc att gat gat atc atc gct gac ctc      1296
Arg Leu Ser Val Gly Ile Glu Thr Ile Asp Asp Ile Ile Ala Asp Leu
415                 420                 425                 430 gaa ggc ggc ttt gct gca atc tag gcggccgcaa a                         1331
Glu Gly Gly Phe Ala Ala Ile
                435
```

<210> SEQ ID NO 4
<211> LENGTH: 437
<212> TYPE: PRT
<213> ORGANISM: Corynebacterium glutamicum
<220> FEATURE:
<221> NAME/KEY: misc_feature
<222> LOCATION: 1..437
<223> OTHER INFORMATION: Corynebacterium glutamicum ATCC 13032 (strain)
<220> FEATURE:
<223> OTHER INFORMATION: [CDS]:7..1320 from SEQ ID NO 3

<400> SEQUENCE: 4

```
Met Pro Lys Tyr Asp Asn Ser Asn Ala Asp Gln Trp Gly Phe Glu Thr
1               5                   10                  15

Arg Ser Ile His Ala Gly Gln Ser Val Asp Ala Gln Thr Ser Ala Arg
                20                  25                  30

Asn Leu Pro Ile Tyr Gln Ser Thr Ala Phe Val Phe Asp Ser Ala Glu
            35                  40                  45

His Ala Lys Gln Arg Phe Ala Leu Glu Asp Leu Gly Pro Val Tyr Ser
```

```
            50                  55                  60
Arg Leu Thr Asn Pro Thr Val Glu Ala Leu Glu Asn Arg Ile Ala Ser
 65                  70                  75                  80

Leu Glu Gly Gly Val His Ala Val Ala Phe Ser Ser Gly Gln Ala Ala
                 85                  90                  95

Thr Thr Asn Ala Ile Leu Asn Leu Ala Gly Ala Gly Asp His Ile Val
            100                 105                 110

Thr Ser Pro Arg Leu Tyr Gly Gly Thr Glu Thr Leu Phe Leu Ile Thr
        115                 120                 125

Leu Asn Arg Leu Gly Ile Asp Val Ser Phe Val Glu Asn Pro Asp Asp
    130                 135                 140

Pro Glu Ser Trp Gln Ala Val Gln Pro Asn Thr Lys Ala Phe Phe
145                 150                 155                 160

Gly Glu Thr Phe Ala Asn Pro Gln Ala Asp Val Leu Asp Ile Pro Ala
                165                 170                 175

Val Ala Glu Val Ala His Arg Asn Ser Val Pro Leu Ile Ile Asp Asn
            180                 185                 190

Thr Ile Ala Thr Ala Ala Leu Val Arg Pro Leu Glu Leu Gly Ala Asp
        195                 200                 205

Val Val Val Ala Ser Leu Thr Lys Phe Tyr Thr Gly Asn Gly Ser Gly
    210                 215                 220

Leu Gly Gly Val Leu Ile Asp Gly Gly Lys Phe Asp Trp Thr Val Glu
225                 230                 235                 240

Lys Asp Gly Lys Pro Val Phe Pro Tyr Phe Val Thr Pro Asp Ala Ala
                245                 250                 255

Tyr His Gly Leu Lys Tyr Ala Asp Leu Gly Ala Pro Ala Phe Gly Leu
            260                 265                 270

Lys Val Arg Val Gly Leu Leu Arg Asp Thr Gly Ser Thr Leu Ser Ala
        275                 280                 285

Phe Asn Ala Trp Ala Ala Val Gln Gly Ile Asp Thr Leu Ser Leu Arg
    290                 295                 300

Leu Glu Arg His Asn Glu Asn Ala Ile Lys Val Ala Glu Phe Leu Asn
305                 310                 315                 320

Asn His Glu Lys Val Glu Lys Val Asn Phe Ala Gly Leu Lys Asp Ser
                325                 330                 335

Pro Trp Tyr Ala Thr Lys Glu Lys Leu Gly Leu Lys Tyr Thr Gly Ser
            340                 345                 350

Val Leu Thr Phe Glu Ile Lys Gly Gly Lys Asp Glu Ala Trp Ala Phe
        355                 360                 365

Ile Asp Ala Leu Lys Leu His Ser Asn Leu Ala Asn Ile Gly Asp Val
    370                 375                 380

Arg Ser Leu Val Val His Pro Ala Thr Thr Thr His Ser Gln Ser Asp
385                 390                 395                 400

Glu Ala Gly Leu Ala Arg Ala Gly Val Thr Gln Ser Thr Val Arg Leu
                405                 410                 415

Ser Val Gly Ile Glu Thr Ile Asp Asp Ile Ile Ala Asp Leu Glu Gly
            420                 425                 430

Gly Phe Ala Ala Ile
            435

<210> SEQ ID NO 5
<211> LENGTH: 1314
<212> TYPE: DNA
<213> ORGANISM: Corynebacterium glutamicum
```

<220> FEATURE:
<221> NAME/KEY: misc_feature
<222> LOCATION: 1..1314
<223> OTHER INFORMATION: Corynebacterium glutamicum ATCC 13032 (strain)
<220> FEATURE:
<221> NAME/KEY: CDS
<222> LOCATION: 1..1314
<223> OTHER INFORMATION: /transl_table=11
<220> FEATURE:
<221> NAME/KEY: misc_feature
<222> LOCATION: 1..1314
<223> OTHER INFORMATION: /gene="metY allelic varation from
    Corynebacterium glutamicum ATCC 13032"
<220> FEATURE:
<221> NAME/KEY: misc_feature
<222> LOCATION: 4..6
<223> OTHER INFORMATION: /note="aca codon for threonine at amino acid
    position 2"

<400> SEQUENCE: 5

| | | |
|---|---|---|
| atg aca aag tac gac aat tcc aat gct gac cag tgg ggc ttt gaa acc<br>Met Thr Lys Tyr Asp Asn Ser Asn Ala Asp Gln Trp Gly Phe Glu Thr<br>1               5                   10                  15 | 48 |
| cgc tcc att cac gca ggc cag tca gta gac gca cag acc agc gca cga<br>Arg Ser Ile His Ala Gly Gln Ser Val Asp Ala Gln Thr Ser Ala Arg<br>            20                  25                  30 | 96 |
| aac ctt ccg atc tac caa tcc acc gct ttc gtg ttc gac tcc gct gag<br>Asn Leu Pro Ile Tyr Gln Ser Thr Ala Phe Val Phe Asp Ser Ala Glu<br>        35                  40                  45 | 144 |
| cac gcc aag cag cgt ttc gca ctt gag gat cta ggc cct gtt tac tcc<br>His Ala Lys Gln Arg Phe Ala Leu Glu Asp Leu Gly Pro Val Tyr Ser<br>    50                  55                  60 | 192 |
| cgc ctc acc aac cca acc gtt gag gct ttg gaa aac cgc atc gct tcc<br>Arg Leu Thr Asn Pro Thr Val Glu Ala Leu Glu Asn Arg Ile Ala Ser<br>65                  70                  75                  80 | 240 |
| ctc gaa ggt ggc gtc cac gct gta gcg ttc tcc tcc gga cag gcc gca<br>Leu Glu Gly Gly Val His Ala Val Ala Phe Ser Ser Gly Gln Ala Ala<br>                85                  90                  95 | 288 |
| acc acc aac gcc att ttg aac ctg gca gga gcg ggc gac cac atc gtc<br>Thr Thr Asn Ala Ile Leu Asn Leu Ala Gly Ala Gly Asp His Ile Val<br>            100                 105                 110 | 336 |
| acc tcc cca cgc ctc tac ggt ggc acc gag act cta ttc ctt atc act<br>Thr Ser Pro Arg Leu Tyr Gly Gly Thr Glu Thr Leu Phe Leu Ile Thr<br>        115                 120                 125 | 384 |
| ctt aac cgc ctg ggt atc gat gtt tcc ttc gtg gaa aac ccc gac gac<br>Leu Asn Arg Leu Gly Ile Asp Val Ser Phe Val Glu Asn Pro Asp Asp<br>    130                 135                 140 | 432 |
| cct gag tcc tgg cag gca gcc gtt cag cca aac acc aaa gca ttc ttc<br>Pro Glu Ser Trp Gln Ala Ala Val Gln Pro Asn Thr Lys Ala Phe Phe<br>145                 150                 155                 160 | 480 |
| ggc gag act ttc gcc aac cca cag gca gac gtc ctg gat att cct gcg<br>Gly Glu Thr Phe Ala Asn Pro Gln Ala Asp Val Leu Asp Ile Pro Ala<br>                165                 170                 175 | 528 |
| gtg gct gaa gtt gcg cac cgc aac agc gtt cca ctg atc atc gac aac<br>Val Ala Glu Val Ala His Arg Asn Ser Val Pro Leu Ile Ile Asp Asn<br>            180                 185                 190 | 576 |
| acc atc gct acc gca gcg ctc gtg cgc ccg ctc gag ctc ggc gca gac<br>Thr Ile Ala Thr Ala Ala Leu Val Arg Pro Leu Glu Leu Gly Ala Asp<br>        195                 200                 205 | 624 |
| gtt gtc gtc gct tcc ctc acc aag ttc tac acc ggc aac ggc tcc gga<br>Val Val Val Ala Ser Leu Thr Lys Phe Tyr Thr Gly Asn Gly Ser Gly<br>    210                 215                 220 | 672 |
| ctg ggc ggc gtg ctt atc gac ggc gga aag ttc gat tgg act gtc gaa<br>Leu Gly Gly Val Leu Ile Asp Gly Gly Lys Phe Asp Trp Thr Val Glu | 720 |

-continued

```
              225                 230                 235                 240
        aag gat gga aag cca gta ttc ccc tac ttc gtc act cca gat gct gct      768
        Lys Asp Gly Lys Pro Val Phe Pro Tyr Phe Val Thr Pro Asp Ala Ala
                        245                 250                 255 tac cac gga ttg aag tac gca gac ctt ggt gca cca gcc ttc ggc ctc      816
        Tyr His Gly Leu Lys Tyr Ala Asp Leu Gly Ala Pro Ala Phe Gly Leu
                    260                 265                 270 aag gtt cgc gtt ggc ctt cta cgc gac acc ggc tcc acc ctc tcc gca      864
        Lys Val Arg Val Gly Leu Leu Arg Asp Thr Gly Ser Thr Leu Ser Ala
                275                 280                 285 ttc aac gca tgg gct gca gtc cag ggc atc gac acc ctt tcc ctg cgc      912
        Phe Asn Ala Trp Ala Ala Val Gln Gly Ile Asp Thr Leu Ser Leu Arg
            290                 295                 300 ctg gag cgc cac aac gaa aac gcc atc aag gtt gca gaa ttc ctc aac      960
        Leu Glu Arg His Asn Glu Asn Ala Ile Lys Val Ala Glu Phe Leu Asn
        305                 310                 315                 320 aac cac gag aag gtg gaa aag gtt aac ttc gca ggc ctg aag gat tcc     1008
        Asn His Glu Lys Val Glu Lys Val Asn Phe Ala Gly Leu Lys Asp Ser
                        325                 330                 335 cct tgg tac gca acc aag gaa aag ctt ggc ctg aag tac acc ggc tcc     1056
        Pro Trp Tyr Ala Thr Lys Glu Lys Leu Gly Leu Lys Tyr Thr Gly Ser
                    340                 345                 350 gtt ctc acc ttc gag atc aag ggc ggc aag gat gag gct tgg gca ttt     1104
        Val Leu Thr Phe Glu Ile Lys Gly Gly Lys Asp Glu Ala Trp Ala Phe
                355                 360                 365 atc gac gcc ctg aag cta cac tcc aac ctt gca aac atc ggc gat gtt     1152
        Ile Asp Ala Leu Lys Leu His Ser Asn Leu Ala Asn Ile Gly Asp Val
            370                 375                 380 cgc tcc ctc gtt gtt cac cca gca acc acc acc cat tca cag tcc gac     1200
        Arg Ser Leu Val Val His Pro Ala Thr Thr Thr His Ser Gln Ser Asp
        385                 390                 395                 400 gaa gct ggc ctg gca cgc gcg ggc gtt acc cag tcc acc gtc cgc ctg     1248
        Glu Ala Gly Leu Ala Arg Ala Gly Val Thr Gln Ser Thr Val Arg Leu
                        405                 410                 415 tcc gtt ggc atc gag acc att gat gat atc atc gct gac ctc gaa ggc     1296
        Ser Val Gly Ile Glu Thr Ile Asp Asp Ile Ile Ala Asp Leu Glu Gly
                    420                 425                 430 ggc ttt gct gca atc tag                                             1314
        Gly Phe Ala Ala Ile
                435

<210> SEQ ID NO 6
<211> LENGTH: 437
<212> TYPE: PRT
<213> ORGANISM: Corynebacterium glutamicum
<220> FEATURE:
<221> NAME/KEY: misc_feature
<222> LOCATION: 1..437
<223> OTHER INFORMATION: Corynebacterium glutamicum ATCC 13032 (strain)
<220> FEATURE:
<223> OTHER INFORMATION: [CDS]:1..1314 from SEQ ID NO 5

<400> SEQUENCE: 6

Met Thr Lys Tyr Asp Asn Ser Asn Ala Asp Gln Trp Gly Phe Glu Thr
1               5                   10                  15

Arg Ser Ile His Ala Gly Gln Ser Val Asp Ala Gln Thr Ser Ala Arg
            20                  25                  30

Asn Leu Pro Ile Tyr Gln Ser Thr Ala Phe Val Phe Asp Ser Ala Glu
        35                  40                  45

His Ala Lys Gln Arg Phe Ala Leu Glu Asp Leu Gly Pro Val Tyr Ser
    50                  55                  60
```

```
Arg Leu Thr Asn Pro Thr Val Glu Ala Leu Glu Asn Arg Ile Ala Ser
 65                  70                  75                  80

Leu Glu Gly Gly Val His Ala Val Ala Phe Ser Ser Gly Gln Ala Ala
                 85                  90                  95

Thr Thr Asn Ala Ile Leu Asn Leu Ala Gly Ala Gly Asp His Ile Val
            100                 105                 110

Thr Ser Pro Arg Leu Tyr Gly Gly Thr Glu Thr Leu Phe Leu Ile Thr
        115                 120                 125

Leu Asn Arg Leu Gly Ile Asp Val Ser Phe Val Glu Asn Pro Asp Asp
130                 135                 140

Pro Glu Ser Trp Gln Ala Ala Val Gln Pro Asn Thr Lys Ala Phe Phe
145                 150                 155                 160

Gly Glu Thr Phe Ala Asn Pro Gln Ala Asp Val Leu Asp Ile Pro Ala
                165                 170                 175

Val Ala Glu Val Ala His Arg Asn Ser Val Pro Leu Ile Ile Asp Asn
            180                 185                 190

Thr Ile Ala Thr Ala Ala Leu Val Arg Pro Leu Glu Leu Gly Ala Asp
        195                 200                 205

Val Val Val Ala Ser Leu Thr Lys Phe Tyr Thr Gly Asn Gly Ser Gly
210                 215                 220

Leu Gly Gly Val Leu Ile Asp Gly Gly Lys Phe Asp Trp Thr Val Glu
225                 230                 235                 240

Lys Asp Gly Lys Pro Val Phe Pro Tyr Phe Val Thr Pro Asp Ala Ala
                245                 250                 255

Tyr His Gly Leu Lys Tyr Ala Asp Leu Gly Ala Pro Ala Phe Gly Leu
            260                 265                 270

Lys Val Arg Val Gly Leu Leu Arg Asp Thr Gly Ser Thr Leu Ser Ala
        275                 280                 285

Phe Asn Ala Trp Ala Ala Val Gln Gly Ile Asp Thr Leu Ser Leu Arg
290                 295                 300

Leu Glu Arg His Asn Glu Asn Ala Ile Lys Val Ala Glu Phe Leu Asn
305                 310                 315                 320

Asn His Glu Lys Val Glu Lys Val Asn Phe Ala Gly Leu Lys Asp Ser
                325                 330                 335

Pro Trp Tyr Ala Thr Lys Glu Lys Leu Gly Leu Lys Tyr Thr Gly Ser
            340                 345                 350

Val Leu Thr Phe Glu Ile Lys Gly Gly Lys Asp Glu Ala Trp Ala Phe
        355                 360                 365

Ile Asp Ala Leu Lys Leu His Ser Asn Leu Ala Asn Ile Gly Asp Val
370                 375                 380

Arg Ser Leu Val Val His Pro Ala Thr Thr Thr His Ser Gln Ser Asp
385                 390                 395                 400

Glu Ala Gly Leu Ala Arg Ala Gly Val Thr Gln Ser Thr Val Arg Leu
                405                 410                 415

Ser Val Gly Ile Glu Thr Ile Asp Asp Ile Ile Ala Asp Leu Glu Gly
            420                 425                 430

Gly Phe Ala Ala Ile
            435

<210> SEQ ID NO 7
<211> LENGTH: 1331
<212> TYPE: DNA
<213> ORGANISM: Corynebacterium glutamicum
<220> FEATURE:
```

-continued

```
<221> NAME/KEY: misc_feature
<222> LOCATION: 1..1331
<223> OTHER INFORMATION: Corynebacterium glutamicum ATCC 13032 (strain)
<220> FEATURE:
<221> NAME/KEY: misc_feature
<222> LOCATION: 4..9
<223> OTHER INFORMATION: /note="restriction site NdeI"
<220> FEATURE:
<221> NAME/KEY: CDS
<222> LOCATION: 7..1320
<223> OTHER INFORMATION: /transl_table=11
<220> FEATURE:
<221> NAME/KEY: misc_feature
<222> LOCATION: 10..12
<223> OTHER INFORMATION: /note="aca codon for threonine at amino acid
      position 2"
<220> FEATURE:
<221> NAME/KEY: misc_feature
<222> LOCATION: 1321..1328
<223> OTHER INFORMATION: /note="restriction site NotI"

<400> SEQUENCE: 7 aaacat atg aca aag tac gac aat tcc aat gct gac cag tgg ggc ttt         48
       Met Thr Lys Tyr Asp Asn Ser Asn Ala Asp Gln Trp Gly Phe
       1               5                   10 gaa acc cgc tcc att cac gca ggc cag tca gta gac gca cag acc agc        96
Glu Thr Arg Ser Ile His Ala Gly Gln Ser Val Asp Ala Gln Thr Ser
15                  20                  25                  30 gca cga aac ctt ccg atc tac caa tcc acc gct ttc gtg ttc gac tcc       144
Ala Arg Asn Leu Pro Ile Tyr Gln Ser Thr Ala Phe Val Phe Asp Ser
                35                  40                  45 gct gag cac gcc aag cag cgt ttc gca ctt gag gat cta ggc cct gtt       192
Ala Glu His Ala Lys Gln Arg Phe Ala Leu Glu Asp Leu Gly Pro Val
            50                  55                  60 tac tcc cgc ctc acc aac cca acc gtt gag gct ttg gaa aac cgc atc       240
Tyr Ser Arg Leu Thr Asn Pro Thr Val Glu Ala Leu Glu Asn Arg Ile
        65                  70                  75 gct tcc ctc gaa ggt ggc gtc cac gct gta gcg ttc tcc tcc gga cag       288
Ala Ser Leu Glu Gly Gly Val His Ala Val Ala Phe Ser Ser Gly Gln
80                  85                  90 gcc gca acc acc aac gcc att ttg aac ctg gca gga gcg ggc gac cac       336
Ala Ala Thr Thr Asn Ala Ile Leu Asn Leu Ala Gly Ala Gly Asp His
95                  100                 105                 110 atc gtc acc tcc cca cgc ctc tac ggt ggc acc gag act cta ttc ctt       384
Ile Val Thr Ser Pro Arg Leu Tyr Gly Gly Thr Glu Thr Leu Phe Leu
                115                 120                 125 atc act ctt aac cgc ctg ggt atc gat gtt tcc ttc gtg gaa aac ccc       432
Ile Thr Leu Asn Arg Leu Gly Ile Asp Val Ser Phe Val Glu Asn Pro
            130                 135                 140 gac gac cct gag tcc tgg cag gca gcc gtt cag cca aac acc aaa gca       480
Asp Asp Pro Glu Ser Trp Gln Ala Ala Val Gln Pro Asn Thr Lys Ala
        145                 150                 155 ttc ttc ggc gag act ttc gcc aac cca cag gca gac gtc ctg gat att       528
Phe Phe Gly Glu Thr Phe Ala Asn Pro Gln Ala Asp Val Leu Asp Ile
    160                 165                 170 cct gcg gtg gct gaa gtt gcg cac cgc aac agc gtt cca ctg atc atc       576
Pro Ala Val Ala Glu Val Ala His Arg Asn Ser Val Pro Leu Ile Ile
175                 180                 185                 190 gac aac acc atc gct acc gca gcg ctc gtg cgc ccg ctc gag ctc ggc       624
Asp Asn Thr Ile Ala Thr Ala Ala Leu Val Arg Pro Leu Glu Leu Gly
                195                 200                 205 gca gac gtt gtc gtc gct tcc ctc acc aag ttc tac acc ggc aac ggc       672
Ala Asp Val Val Val Ala Ser Leu Thr Lys Phe Tyr Thr Gly Asn Gly
            210                 215                 220
```

-continued

| | | |
|---|---|---|
| tcc gga ctg ggc ggc gtg ctt atc gac ggc gga aag ttc gat tgg act<br>Ser Gly Leu Gly Gly Val Leu Ile Asp Gly Gly Lys Phe Asp Trp Thr<br>225 230 235 | 720 |
| gtc gaa aag gat gga aag cca gta ttc ccc tac ttc gtc act cca gat<br>Val Glu Lys Asp Gly Lys Pro Val Phe Pro Tyr Phe Val Thr Pro Asp<br>240 245 250 | 768 |
| gct gct tac cac gga ttg aag tac gca gac ctt ggt gca cca gcc ttc<br>Ala Ala Tyr His Gly Leu Lys Tyr Ala Asp Leu Gly Ala Pro Ala Phe<br>255 260 265 270 | 816 |
| ggc ctc aag gtt cgc gtt ggc ctt cta cgc gac acc ggc tcc acc ctc<br>Gly Leu Lys Val Arg Val Gly Leu Leu Arg Asp Thr Gly Ser Thr Leu<br>275 280 285 | 864 |
| tcc gca ttc aac gca tgg gct gca gtc cag ggc atc gac acc ctt tcc<br>Ser Ala Phe Asn Ala Trp Ala Ala Val Gln Gly Ile Asp Thr Leu Ser<br>290 295 300 | 912 |
| ctg cgc ctg gag cgc cac aac gaa aac gcc atc aag gtt gca gaa ttc<br>Leu Arg Leu Glu Arg His Asn Glu Asn Ala Ile Lys Val Ala Glu Phe<br>305 310 315 | 960 |
| ctc aac aac cac gag aag gtg gaa aag gtt aac ttc gca ggc ctg aag<br>Leu Asn Asn His Glu Lys Val Glu Lys Val Asn Phe Ala Gly Leu Lys<br>320 325 330 | 1008 |
| gat tcc cct tgg tac gca acc aag gaa aag ctt ggc ctg aag tac acc<br>Asp Ser Pro Trp Tyr Ala Thr Lys Glu Lys Leu Gly Leu Lys Tyr Thr<br>335 340 345 350 | 1056 |
| ggc tcc gtt ctc acc ttc gag atc aag ggc ggc aag gat gag gct tgg<br>Gly Ser Val Leu Thr Phe Glu Ile Lys Gly Gly Lys Asp Glu Ala Trp<br>355 360 365 | 1104 |
| gca ttt atc gac gcc ctg aag cta cac tcc aac ctt gca aac atc ggc<br>Ala Phe Ile Asp Ala Leu Lys Leu His Ser Asn Leu Ala Asn Ile Gly<br>370 375 380 | 1152 |
| gat gtt cgc tcc ctc gtt gtt cac cca gca acc acc acc cat tca cag<br>Asp Val Arg Ser Leu Val Val His Pro Ala Thr Thr Thr His Ser Gln<br>385 390 395 | 1200 |
| tcc gac gaa gct ggc ctg gca cgc gcg ggc gtt acc cag tcc acc gtc<br>Ser Asp Glu Ala Gly Leu Ala Arg Ala Gly Val Thr Gln Ser Thr Val<br>400 405 410 | 1248 |
| cgc ctg tcc gtt ggc atc gag acc att gat gat atc atc gct gac ctc<br>Arg Leu Ser Val Gly Ile Glu Thr Ile Asp Asp Ile Ile Ala Asp Leu<br>415 420 425 430 | 1296 |
| gaa ggc ggc ttt gct gca atc tag gcggccgcaa a<br>Glu Gly Gly Phe Ala Ala Ile<br>435 | 1331 |

<210> SEQ ID NO 8
<211> LENGTH: 437
<212> TYPE: PRT
<213> ORGANISM: Corynebacterium glutamicum
<220> FEATURE:
<221> NAME/KEY: misc_feature
<222> LOCATION: 1..437
<223> OTHER INFORMATION: Corynebacterium glutamicum ATCC 13032 (strain)
<220> FEATURE:
<223> OTHER INFORMATION: [CDS]:7..1320 from SEQ ID NO 7

<400> SEQUENCE: 8

Met Thr Lys Tyr Asp Asn Ser Asn Ala Asp Gln Trp Gly Phe Glu Thr
1               5                   10                  15

Arg Ser Ile His Ala Gly Gln Ser Val Asp Ala Gln Thr Ser Ala Arg
            20                  25                  30

Asn Leu Pro Ile Tyr Gln Ser Thr Ala Phe Val Phe Asp Ser Ala Glu
        35                  40                  45

```
His Ala Lys Gln Arg Phe Ala Leu Glu Asp Leu Gly Pro Val Tyr Ser
    50                  55                  60

Arg Leu Thr Asn Pro Thr Val Glu Ala Leu Glu Asn Arg Ile Ala Ser
65                  70                  75                  80

Leu Glu Gly Gly Val His Ala Val Ala Phe Ser Ser Gly Gln Ala Ala
                85                  90                  95

Thr Thr Asn Ala Ile Leu Asn Leu Ala Gly Ala Gly Asp His Ile Val
            100                 105                 110

Thr Ser Pro Arg Leu Tyr Gly Gly Thr Glu Thr Leu Phe Leu Ile Thr
            115                 120                 125

Leu Asn Arg Leu Gly Ile Asp Val Ser Phe Val Glu Asn Pro Asp Asp
130                 135                 140

Pro Glu Ser Trp Gln Ala Val Gln Pro Asn Thr Lys Ala Phe Phe
145                 150                 155                 160

Gly Glu Thr Phe Ala Asn Pro Gln Ala Asp Val Leu Asp Ile Pro Ala
                165                 170                 175

Val Ala Glu Val Ala His Arg Asn Ser Val Pro Leu Ile Ile Asp Asn
            180                 185                 190

Thr Ile Ala Thr Ala Ala Leu Val Arg Pro Leu Glu Leu Gly Ala Asp
            195                 200                 205

Val Val Val Ala Ser Leu Thr Lys Phe Tyr Thr Gly Asn Gly Ser Gly
210                 215                 220

Leu Gly Gly Val Leu Ile Asp Gly Gly Lys Phe Asp Trp Thr Val Glu
225                 230                 235                 240

Lys Asp Gly Lys Pro Val Phe Pro Tyr Phe Val Thr Pro Asp Ala Ala
                245                 250                 255

Tyr His Gly Leu Lys Tyr Ala Asp Leu Gly Ala Pro Ala Phe Gly Leu
            260                 265                 270

Lys Val Arg Val Gly Leu Leu Arg Asp Thr Gly Ser Thr Leu Ser Ala
            275                 280                 285

Phe Asn Ala Trp Ala Ala Val Gln Gly Ile Asp Thr Leu Ser Leu Arg
290                 295                 300

Leu Glu Arg His Asn Glu Asn Ala Ile Lys Val Ala Glu Phe Leu Asn
305                 310                 315                 320

Asn His Glu Lys Val Glu Lys Val Asn Phe Ala Gly Leu Lys Asp Ser
                325                 330                 335

Pro Trp Tyr Ala Thr Lys Glu Lys Leu Gly Leu Lys Tyr Thr Gly Ser
            340                 345                 350

Val Leu Thr Phe Glu Ile Lys Gly Gly Lys Asp Glu Ala Trp Ala Phe
            355                 360                 365

Ile Asp Ala Leu Lys Leu His Ser Asn Leu Ala Asn Ile Gly Asp Val
370                 375                 380

Arg Ser Leu Val Val His Pro Ala Thr Thr Thr His Ser Gln Ser Asp
385                 390                 395                 400

Glu Ala Gly Leu Ala Arg Ala Gly Val Thr Gln Ser Thr Val Arg Leu
                405                 410                 415

Ser Val Gly Ile Glu Thr Ile Asp Asp Ile Ala Asp Leu Glu Gly
            420                 425                 430

Gly Phe Ala Ala Ile
            435

<210> SEQ ID NO 9
<211> LENGTH: 1185
<212> TYPE: DNA
```

<213> ORGANISM: Chromobacterium violaceum
<220> FEATURE:
<221> NAME/KEY: misc_feature
<222> LOCATION: 1..1185
<223> OTHER INFORMATION: Chromobacterium violaceum ATCC 12472 (strain)
<220> FEATURE:
<221> NAME/KEY: CDS
<222> LOCATION: 1..1185
<223> OTHER INFORMATION: /note="nucleotide sequence comprising locus_tag
    CV_2725 disclosed in AE016825"
    /transl_table=11
<220> FEATURE:
<221> NAME/KEY: misc_feature
<222> LOCATION: 1..1185
<223> OTHER INFORMATION: /gene="metZ from Chromobacterium violaceaum
    ATCC 12472"

<400> SEQUENCE: 9

```
atg gca tcc gac gcg ccg cat ctt ccg ctg cac cct gaa acc ctg gcc        48
Met Ala Ser Asp Ala Pro His Leu Pro Leu His Pro Glu Thr Leu Ala
1               5                   10                  15 atc cgg gcc ggg ttg gaa acc agc cag ttc aac gag cac agc cag ggc        96
Ile Arg Ala Gly Leu Glu Thr Ser Gln Phe Asn Glu His Ser Gln Gly
            20                  25                  30 ctg ttc ctg acg tcc agc ttc acc tac gaa tcg gcg gcg cag gcg gcg       144
Leu Phe Leu Thr Ser Ser Phe Thr Tyr Glu Ser Ala Ala Gln Ala Ala
        35                  40                  45 gcg atg ttc ctg ggc gag atc gac ggc tac acc tat tcc cgc ttc acc       192
Ala Met Phe Leu Gly Glu Ile Asp Gly Tyr Thr Tyr Ser Arg Phe Thr
    50                  55                  60 aat ccg acc gtc gcc gcg ttc cag cat agg ctg gcg cag atg gag ggc       240
Asn Pro Thr Val Ala Ala Phe Gln His Arg Leu Ala Gln Met Glu Gly
65                  70                  75                  80 ggg gag cgc gcc atc gcc acc gcc acc ggc atg gcg gcg atc cag gcc       288
Gly Glu Arg Ala Ile Ala Thr Ala Thr Gly Met Ala Ala Ile Gln Ala
                85                  90                  95 atc atg atg act ttg ctg cag gct ggc gac cac atc gtg tcg tcg caa       336
Ile Met Met Thr Leu Leu Gln Ala Gly Asp His Ile Val Ser Ser Gln
            100                 105                 110 agc ctg ttc ggc tcc acc acc aat ctg ttc gcc aac cag ttg gcc aag       384
Ser Leu Phe Gly Ser Thr Thr Asn Leu Phe Ala Asn Gln Leu Ala Lys
        115                 120                 125 ttc gcc gtg gcc acc gac ttc gtc gac gcg cgc gac ctg tcc gcc tgg       432
Phe Ala Val Ala Thr Asp Phe Val Asp Ala Arg Asp Leu Ser Ala Trp
    130                 135                 140 cgg gag gcg ctg cgg ccg aac acc aag ctg ctg ttc ctg gag acg ccg       480
Arg Glu Ala Leu Arg Pro Asn Thr Lys Leu Leu Phe Leu Glu Thr Pro
145                 150                 155                 160 tcc aat ccc ttg acc gaa gtg gcc gac atc gcg gcc atc gcc gac atc       528
Ser Asn Pro Leu Thr Glu Val Ala Asp Ile Ala Ala Ile Ala Asp Ile
                165                 170                 175 gcc cac gcg cat ggc gcg ctg ctg gtg gtg gac aac agc ttc tgt tcg       576
Ala His Ala His Gly Ala Leu Leu Val Val Asp Asn Ser Phe Cys Ser
            180                 185                 190 ccg gcc ttg cag cag ccg ttg aaa ctg ggc gcc gat ctg gtc atg cat       624
Pro Ala Leu Gln Gln Pro Leu Lys Leu Gly Ala Asp Leu Val Met His
        195                 200                 205 tcc gcc acc aag ttc atc gac ggc cat ggc cgg gtg atg ggc ggg gcg       672
Ser Ala Thr Lys Phe Ile Asp Gly His Gly Arg Val Met Gly Gly Ala
    210                 215                 220 gtg gtc ggc agc gac aag ctg gtc gag cag gtc tat ttg cac gtg cgc       720
Val Val Gly Ser Asp Lys Leu Val Glu Gln Val Tyr Leu His Val Arg
225                 230                 235                 240
```

```
gcc gcc ggt ccc tcg ctg gcg ccg ttc aat gcc tgg acg ctg ctg tcc      768
Ala Ala Gly Pro Ser Leu Ala Pro Phe Asn Ala Trp Thr Leu Leu Ser
            245                 250                 255 ggt ttg gag acg ctg cac ctg cgg atg gag aag cac agc gcc aac gcg      816
Gly Leu Glu Thr Leu His Leu Arg Met Glu Lys His Ser Ala Asn Ala
        260                 265                 270 ctg gag ctg gcg cgc tgg ctg gag gcg cag ccc aat gtg gag cgc gtc      864
Leu Glu Leu Ala Arg Trp Leu Glu Ala Gln Pro Asn Val Glu Arg Val
    275                 280                 285 tat tac ccg ggc ctg gag agc cac ccc cag cac gag ctg gcg ctg cgc      912
Tyr Tyr Pro Gly Leu Glu Ser His Pro Gln His Glu Leu Ala Leu Arg
290                 295                 300 cag cag aag agc ggc gga gcg gtg gtg tcc ttc gtg gtc aag ggc ggc      960
Gln Gln Lys Ser Gly Gly Ala Val Val Ser Phe Val Val Lys Gly Gly
305                 310                 315                 320 cgc aag gcc gcg tgg aaa gtg gtg gac gcg gtc agg gtg atc tcg cgc     1008
Arg Lys Ala Ala Trp Lys Val Val Asp Ala Val Arg Val Ile Ser Arg
                325                 330                 335 acc gcc aat ctg ggc gat gtg aaa acc acc ctc act cat ccg gcc agc     1056
Thr Ala Asn Leu Gly Asp Val Lys Thr Thr Leu Thr His Pro Ala Ser
            340                 345                 350 acc acc cac gcc cgc gtg acg cag gag gcg cgc gag cgc gcc ggc atc     1104
Thr Thr His Ala Arg Val Thr Gln Glu Ala Arg Glu Arg Ala Gly Ile
        355                 360                 365 gtc gag ggg ctg ttg cgc gtc agc gtc ggc ctg gaa aat gta cgg gac     1152
Val Glu Gly Leu Leu Arg Val Ser Val Gly Leu Glu Asn Val Arg Asp
    370                 375                 380 ctt caa caa gat ctg ttg cgg ggc ctt gac taa                          1185
Leu Gln Gln Asp Leu Leu Arg Gly Leu Asp
385                 390
```

<210> SEQ ID NO 10
<211> LENGTH: 394
<212> TYPE: PRT
<213> ORGANISM: Chromobacterium violaceum
<220> FEATURE:
<221> NAME/KEY: misc_feature
<222> LOCATION: 1..394
<223> OTHER INFORMATION: Chromobacterium violaceum ATCC 12472 (strain)
<220> FEATURE:
<223> OTHER INFORMATION: [CDS]:1..1185 from SEQ ID NO 9

<400> SEQUENCE: 10

```
Met Ala Ser Asp Ala Pro His Leu Pro Leu His Pro Glu Thr Leu Ala
1               5                   10                  15

Ile Arg Ala Gly Leu Glu Thr Ser Gln Phe Asn Glu His Ser Gln Gly
            20                  25                  30

Leu Phe Leu Thr Ser Ser Phe Thr Tyr Glu Ser Ala Ala Gln Ala Ala
        35                  40                  45

Ala Met Phe Leu Gly Glu Ile Asp Gly Tyr Thr Tyr Ser Arg Phe Thr
    50                  55                  60

Asn Pro Thr Val Ala Ala Phe Gln His Arg Leu Ala Gln Met Glu Gly
65                  70                  75                  80

Gly Glu Arg Ala Ile Ala Thr Ala Thr Gly Met Ala Ala Ile Gln Ala
                85                  90                  95

Ile Met Met Thr Leu Leu Gln Ala Gly Asp His Ile Val Ser Ser Gln
            100                 105                 110

Ser Leu Phe Gly Ser Thr Thr Asn Leu Phe Ala Asn Gln Leu Ala Lys
        115                 120                 125

Phe Ala Val Ala Thr Asp Phe Val Asp Ala Arg Asp Leu Ser Ala Trp
```

```
                   130                 135                 140
Arg Glu Ala Leu Arg Pro Asn Thr Lys Leu Leu Phe Leu Glu Thr Pro
145                 150                 155                 160

Ser Asn Pro Leu Thr Glu Val Ala Asp Ile Ala Ala Ile Ala Asp Ile
                165                 170                 175

Ala His Ala His Gly Ala Leu Leu Val Val Asp Asn Ser Phe Cys Ser
                180                 185                 190

Pro Ala Leu Gln Gln Pro Leu Lys Leu Gly Ala Asp Leu Val Met His
                195                 200                 205

Ser Ala Thr Lys Phe Ile Asp Gly His Gly Arg Val Met Gly Gly Ala
                210                 215                 220

Val Val Gly Ser Asp Lys Leu Val Glu Gln Val Tyr Leu His Val Arg
225                 230                 235                 240

Ala Ala Gly Pro Ser Leu Ala Pro Phe Asn Ala Trp Thr Leu Leu Ser
                245                 250                 255

Gly Leu Glu Thr Leu His Leu Arg Met Glu Lys His Ser Ala Asn Ala
                260                 265                 270

Leu Glu Leu Ala Arg Trp Leu Glu Ala Gln Pro Asn Val Glu Arg Val
                275                 280                 285

Tyr Tyr Pro Gly Leu Glu Ser His Pro Gln His Glu Leu Ala Leu Arg
                290                 295                 300

Gln Gln Lys Ser Gly Gly Ala Val Val Ser Phe Val Val Lys Gly Gly
305                 310                 315                 320

Arg Lys Ala Ala Trp Lys Val Val Asp Ala Val Arg Val Ile Ser Arg
                325                 330                 335

Thr Ala Asn Leu Gly Asp Val Lys Thr Thr Leu Thr His Pro Ala Ser
                340                 345                 350

Thr Thr His Ala Arg Val Thr Gln Glu Ala Arg Glu Arg Ala Gly Ile
                355                 360                 365

Val Glu Gly Leu Leu Arg Val Ser Val Gly Leu Glu Asn Val Arg Asp
                370                 375                 380

Leu Gln Gln Asp Leu Leu Arg Gly Leu Asp
385                 390

<210> SEQ ID NO 11
<211> LENGTH: 1200
<212> TYPE: DNA
<213> ORGANISM: Chromobacterium violaceum
<220> FEATURE:
<221> NAME/KEY: misc_feature
<222> LOCATION: 1..1200
<223> OTHER INFORMATION: Chromobacterium violaceum ATCC 12472 (strain)
<220> FEATURE:
<221> NAME/KEY: misc_feature
<222> LOCATION: 4..9
<223> OTHER INFORMATION: /note="restriction site NdeI"
<220> FEATURE:
<221> NAME/KEY: CDS
<222> LOCATION: 7..1191
<223> OTHER INFORMATION: /transl_table=11
<220> FEATURE:
<221> NAME/KEY: misc_feature
<222> LOCATION: 1191..1197
<223> OTHER INFORMATION: /note="restriction site XhoI"

<400> SEQUENCE: 11 aaacat atg gca tcc gac gcg ccg cat ctt ccg ctg cac cct gaa acc        48
       Met Ala Ser Asp Ala Pro His Leu Pro Leu His Pro Glu Thr
       1               5                   10 ctg gcc atc cgg gcc ggg ttg gaa acc agc cag ttc aac gag cac agc       96
```

-continued

| | | |
|---|---|---|
| Leu Ala Ile Arg Ala Gly Leu Glu Thr Ser Gln Phe Asn Glu His Ser<br>15                    20                    25                    30 | |
| cag ggc ctg ttc ctg acg tcc agc ttc acc tac gaa tcg gcc gcg cag<br>Gln Gly Leu Phe Leu Thr Ser Ser Phe Thr Tyr Glu Ser Ala Ala Gln<br>                    35                    40                    45 | 144 |
| gcg gcg gcg atg ttc ctg ggc gag atc gac ggc tac acc tat tcc cgc<br>Ala Ala Ala Met Phe Leu Gly Glu Ile Asp Gly Tyr Thr Tyr Ser Arg<br>             50                    55                    60 | 192 |
| ttc acc aat ccg acc gtc gcc gcg ttc cag cat agg ctg gcg cag atg<br>Phe Thr Asn Pro Thr Val Ala Ala Phe Gln His Arg Leu Ala Gln Met<br>        65                    70                    75 | 240 |
| gag ggc ggg gag cgc gcc atc gcc acc gcc acc ggc atg gcg gcg atc<br>Glu Gly Gly Glu Arg Ala Ile Ala Thr Ala Thr Gly Met Ala Ala Ile<br>80                    85                    90 | 288 |
| cag gcc atc atg atg act ttg ctg cag gct ggc gac cac atc gtg tcg<br>Gln Ala Ile Met Met Thr Leu Leu Gln Ala Gly Asp His Ile Val Ser<br>95                    100                 105             110 | 336 |
| tcg caa agc ctg ttc ggc tcc acc acc aat ctg ttc gcc aac cag ttg<br>Ser Gln Ser Leu Phe Gly Ser Thr Thr Asn Leu Phe Ala Asn Gln Leu<br>                115                 120                 125 | 384 |
| gcc aag ttc gcc gtg gcc acc gac ttc gtc gac gcg cgc gac ctg tcc<br>Ala Lys Phe Ala Val Ala Thr Asp Phe Val Asp Ala Arg Asp Leu Ser<br>           130                   135                 140 | 432 |
| gcc tgg cgg gag gcg ctg cgg ccg aac acc aag ctg ctg ttc ctg gag<br>Ala Trp Arg Glu Ala Leu Arg Pro Asn Thr Lys Leu Leu Phe Leu Glu<br>                145                 150                 155 | 480 |
| acg ccg tcc aat ccc ttg acc gaa gtg gcc gac atc gcg gcc atc gcc<br>Thr Pro Ser Asn Pro Leu Thr Glu Val Ala Asp Ile Ala Ala Ile Ala<br>160                    165                 170 | 528 |
| gac atc gcc cac gcg cat ggc gcg ctg ctg gtg gtg gac aac agc ttc<br>Asp Ile Ala His Ala His Gly Ala Leu Leu Val Val Asp Asn Ser Phe<br>175                    180                 185                 190 | 576 |
| tgt tcg ccg gcc ttg cag cag ccg ttg aaa ctg ggc gcc gat ctg gtc<br>Cys Ser Pro Ala Leu Gln Gln Pro Leu Lys Leu Gly Ala Asp Leu Val<br>                195                 200                 205 | 624 |
| atg cat tcc gcc acc aag ttc atc gac ggc cat ggc cgg gtg atg ggc<br>Met His Ser Ala Thr Lys Phe Ile Asp Gly His Gly Arg Val Met Gly<br>210                    215                 220 | 672 |
| ggg gcg gtg gtc ggc agc gac aag ctg gtc gag cag gtc tat ttg cac<br>Gly Ala Val Val Gly Ser Asp Lys Leu Val Glu Gln Val Tyr Leu His<br>225                    230                 235 | 720 |
| gtg cgc gcc gcc ggt ccc tcg ctg gcg ccg ttc aat gcc tgg acg ctg<br>Val Arg Ala Ala Gly Pro Ser Leu Ala Pro Phe Asn Ala Trp Thr Leu<br>240                    245                 250 | 768 |
| ctg tcc ggt ttg gag acg ctg cac ctg cgg atg gag aag cac agc gcc<br>Leu Ser Gly Leu Glu Thr Leu His Leu Arg Met Glu Lys His Ser Ala<br>255                    260                 265                 270 | 816 |
| aac gcg ctg gag ctg gcg cgc tgg ctg gag gcg cag ccc aat gtg gag<br>Asn Ala Leu Glu Leu Ala Arg Trp Leu Glu Ala Gln Pro Asn Val Glu<br>                275                 280                 285 | 864 |
| cgc gtc tat tac ccg ggc ctg gag agc cac ccc cag cac gag ctg gcg<br>Arg Val Tyr Tyr Pro Gly Leu Glu Ser His Pro Gln His Glu Leu Ala<br>                    290                 295                 300 | 912 |
| ctg cgc cag cag aag agc ggc gga gcg gtg gtg tcc ttc gtg gtc aag<br>Leu Arg Gln Gln Lys Ser Gly Gly Ala Val Val Ser Phe Val Val Lys<br>           305                    310                 315 | 960 |
| ggc ggc cgc aag gcc gcg tgg aaa gtg gtg gac gcg gtc agg gtg atc<br>Gly Gly Arg Lys Ala Ala Trp Lys Val Val Asp Ala Val Arg Val Ile<br>320                    325                 330 | 1008 |

```
tcg cgc acc gcc aat ctg ggc gat gtg aaa acc acc ctc act cat ccg    1056
Ser Arg Thr Ala Asn Leu Gly Asp Val Lys Thr Thr Leu Thr His Pro
335                 340                 345                 350 gcc agc acc acc cac gcc cgc gtg acg cag gag gcg cgc gag cgc gcc    1104
Ala Ser Thr Thr His Ala Arg Val Thr Gln Glu Ala Arg Glu Arg Ala
        355                 360                 365 ggc atc gtc gag ggg ctg ttg cgc gtc agc gtc ggc ctg gaa aat gta    1152
Gly Ile Val Glu Gly Leu Leu Arg Val Ser Val Gly Leu Glu Asn Val
370                 375                 380 cgg gac ctt caa caa gat ctg ttg cgg ggc ctt gac taa ctcgagaaa     1200
Arg Asp Leu Gln Gln Asp Leu Leu Arg Gly Leu Asp
        385                 390
```

<210> SEQ ID NO 12
<211> LENGTH: 394
<212> TYPE: PRT
<213> ORGANISM: Chromobacterium violaceum
<220> FEATURE:
<221> NAME/KEY: misc_feature
<222> LOCATION: 1..394
<223> OTHER INFORMATION: Chromobacterium violaceum ATCC 12472 (strain)
<220> FEATURE:
<223> OTHER INFORMATION: [CDS]:7..1191 from SEQ ID NO 11

<400> SEQUENCE: 12

```
Met Ala Ser Asp Ala Pro His Leu Pro Leu His Pro Glu Thr Leu Ala
1               5                   10                  15

Ile Arg Ala Gly Leu Glu Thr Ser Gln Phe Asn Glu His Ser Gln Gly
            20                  25                  30

Leu Phe Leu Thr Ser Ser Phe Thr Tyr Glu Ser Ala Ala Gln Ala Ala
        35                  40                  45

Ala Met Phe Leu Gly Glu Ile Asp Gly Tyr Thr Tyr Ser Arg Phe Thr
    50                  55                  60

Asn Pro Thr Val Ala Ala Phe Gln His Arg Leu Ala Gln Met Glu Gly
65                  70                  75                  80

Gly Glu Arg Ala Ile Ala Thr Ala Thr Gly Met Ala Ala Ile Gln Ala
                85                  90                  95

Ile Met Met Thr Leu Leu Gln Ala Gly Asp His Ile Val Ser Ser Gln
            100                 105                 110

Ser Leu Phe Gly Ser Thr Thr Asn Leu Phe Ala Asn Gln Leu Ala Lys
        115                 120                 125

Phe Ala Val Ala Thr Asp Phe Val Asp Ala Arg Asp Leu Ser Ala Trp
    130                 135                 140

Arg Glu Ala Leu Arg Pro Asn Thr Lys Leu Leu Phe Leu Glu Thr Pro
145                 150                 155                 160

Ser Asn Pro Leu Thr Glu Val Ala Asp Ile Ala Ala Ile Ala Asp Ile
                165                 170                 175

Ala His Ala His Gly Ala Leu Leu Val Val Asp Asn Ser Phe Cys Ser
            180                 185                 190

Pro Ala Leu Gln Gln Pro Leu Lys Leu Gly Ala Asp Leu Val Met His
        195                 200                 205

Ser Ala Thr Lys Phe Ile Asp Gly His Gly Arg Val Met Gly Gly Ala
    210                 215                 220

Val Val Gly Ser Asp Lys Leu Val Glu Gln Val Tyr Leu His Val Arg
225                 230                 235                 240

Ala Ala Gly Pro Ser Leu Ala Pro Phe Asn Ala Trp Thr Leu Leu Ser
                245                 250                 255

Gly Leu Glu Thr Leu His Leu Arg Met Glu Lys His Ser Ala Asn Ala
```

```
                  260                 265                 270
Leu Glu Leu Ala Arg Trp Leu Glu Ala Gln Pro Asn Val Glu Arg Val
            275                 280                 285

Tyr Tyr Pro Gly Leu Glu Ser His Pro Gln His Glu Leu Ala Leu Arg
            290                 295                 300

Gln Gln Lys Ser Gly Gly Ala Val Val Ser Phe Val Lys Gly Gly
305                 310                 315                 320

Arg Lys Ala Ala Trp Lys Val Val Asp Ala Val Arg Val Ile Ser Arg
                325                 330                 335

Thr Ala Asn Leu Gly Asp Val Lys Thr Thr Leu Thr His Pro Ala Ser
            340                 345                 350

Thr Thr His Ala Arg Val Thr Gln Glu Ala Arg Glu Arg Ala Gly Ile
        355                 360                 365

Val Glu Gly Leu Leu Arg Val Ser Val Gly Leu Glu Asn Val Arg Asp
        370                 375                 380

Leu Gln Gln Asp Leu Leu Arg Gly Leu Asp
385                 390
```

<210> SEQ ID NO 13
<211> LENGTH: 1200
<212> TYPE: DNA
<213> ORGANISM: Hyphomonas neptunium
<220> FEATURE:
<221> NAME/KEY: misc_feature
<222> LOCATION: 1..1200
<223> OTHER INFORMATION: Hyphomonas neptunium ATCC 15444 (strain)
<220> FEATURE:
<221> NAME/KEY: CDS
<222> LOCATION: 1..1200
<223> OTHER INFORMATION: /note="nucleotide sequence comprising locus_tag HNE_2672 disclosed in CP000158"
    /transl_table=11
<220> FEATURE:
<221> NAME/KEY: misc_feature
<222> LOCATION: 1..1200
<223> OTHER INFORMATION: /gene="metZ from Hyphomonas neptunium ATCC 15444"

<400> SEQUENCE: 13

```
atg gcg gat gca ccc ggc ggc gac aag aag ggc tgg aag cct gcg acc      48
Met Ala Asp Ala Pro Gly Gly Asp Lys Lys Gly Trp Lys Pro Ala Thr
1               5                   10                  15 cag gcg gta cgc ggc ggc ctg atg cgg tcc cag cat ggg gag att tcc      96
Gln Ala Val Arg Gly Gly Leu Met Arg Ser Gln His Gly Glu Ile Ser
                20                  25                  30 gag gcg ctg tat ctg acc tcc ggc tac gct tac gac tcg gcc gag cag     144
Glu Ala Leu Tyr Leu Thr Ser Gly Tyr Ala Tyr Asp Ser Ala Glu Gln
            35                  40                  45 gcg atg cgc cgg atg gcg ggc gag gaa gaa ggc ttc gtc tat tcc cgc     192
Ala Met Arg Arg Met Ala Gly Glu Glu Glu Gly Phe Val Tyr Ser Arg
        50                  55                  60 tat ggc agc ccg acc aat gag atg ctg caa cag cgc ctc gcg ctg att     240
Tyr Gly Ser Pro Thr Asn Glu Met Leu Gln Gln Arg Leu Ala Leu Ile
65                  70                  75                  80 gaa ggc gcc gaa gcg tgc cgg gtg acg ggc tct ggc atg ggc gcg att     288
Glu Gly Ala Glu Ala Cys Arg Val Thr Gly Ser Gly Met Gly Ala Ile
                85                  90                  95 tcg tcg gcc atc ctg gcg ccg ctt aaa gcg ggc gac cgg gtg gtg gcg     336
Ser Ser Ala Ile Leu Ala Pro Leu Lys Ala Gly Asp Arg Val Val Ala
                100                 105                 110 gcg acc gcg ctg ttt ggc tcg tgc cgc tgg atc att gcc aac cag atg     384
Ala Thr Ala Leu Phe Gly Ser Cys Arg Trp Ile Ile Ala Asn Gln Met
```

```
                115                 120                 125
ccg aag ttt ggc atc gag gca gtg ttc gtg gac ggg gcc gat ctt gat    432
Pro Lys Phe Gly Ile Glu Ala Val Phe Val Asp Gly Ala Asp Leu Asp
    130                 135                 140 gct tgg aag cgc gag atc gac aag ggc tgc cag ctg gtg ctg atc gaa    480
Ala Trp Lys Arg Glu Ile Asp Lys Gly Cys Gln Leu Val Leu Ile Glu
145                 150                 155                 160 agc ccg gcc aat ccg ttg ctc gac ggc gtg gac atc gaa gcg gtc gcc    528
Ser Pro Ala Asn Pro Leu Leu Asp Gly Val Asp Ile Glu Ala Val Ala
                165                 170                 175 agg ctc gcc aag gcg gcg ggc gcg ctg ctg gtg gtg gac aat gtg ttt    576
Arg Leu Ala Lys Ala Ala Gly Ala Leu Leu Val Val Asp Asn Val Phe
            180                 185                 190 gcc acg ccg gtg ctt cag cgg ccg ctg gaa atg ggc gcc gat gtg atc    624
Ala Thr Pro Val Leu Gln Arg Pro Leu Glu Met Gly Ala Asp Val Ile
        195                 200                 205 gcc tat tcg gcc acc aaa cat atg gac ggg cag ggc cgc gtt ctg ctg    672
Ala Tyr Ser Ala Thr Lys His Met Asp Gly Gln Gly Arg Val Leu Leu
    210                 215                 220 ggc gcg atc ctg acg gac gcc aag cgg atg agt gat gtg tat gat ccg    720
Gly Ala Ile Leu Thr Asp Ala Lys Arg Met Ser Asp Val Tyr Asp Pro
225                 230                 235                 240 tgg ctg cgc cat atg ggg ccg gcc gcc tcg ccg ttt aac gcc tgg gta    768
Trp Leu Arg His Met Gly Pro Ala Ala Ser Pro Phe Asn Ala Trp Val
                245                 250                 255 gtg ctg aag ggc ctt gag acg atg cag ctg cgc gtg gaa gcg cag agc    816
Val Leu Lys Gly Leu Glu Thr Met Gln Leu Arg Val Glu Ala Gln Ser
            260                 265                 270 cgc acg gcg gcg cgg ctg gcg gat gtt ctg gcc gat cat ccg gcg gtc    864
Arg Thr Ala Ala Arg Leu Ala Asp Val Leu Ala Asp His Pro Ala Val
        275                 280                 285 aat gcc gtg cgc tat ccc cac cgc aag gat cac ccg cat tat gag gtg    912
Asn Ala Val Arg Tyr Pro His Arg Lys Asp His Pro His Tyr Glu Val
    290                 295                 300 cac aag cgc cag atg aaa tcg ggc ggc acg ctg ctc gcg ctg tcg ctc    960
His Lys Arg Gln Met Lys Ser Gly Gly Thr Leu Leu Ala Leu Ser Leu
305                 310                 315                 320 aag ggc ggg cag gac gcg gcg ttc cgc ttc ctc aac ggg ctg cag ctg   1008
Lys Gly Gly Gln Asp Ala Ala Phe Arg Phe Leu Asn Gly Leu Gln Leu
                325                 330                 335 gtc gac atc tgc aac aac ctt ggc gat acg aaa tcg ctg gcc tgt cat   1056
Val Asp Ile Cys Asn Asn Leu Gly Asp Thr Lys Ser Leu Ala Cys His
            340                 345                 350 ccc tcc acc acg acg cac cgc gcg ttg agt gat gag gat cag gcg gcg   1104
Pro Ser Thr Thr Thr His Arg Ala Leu Ser Asp Glu Asp Gln Ala Ala
        355                 360                 365 atg ggg ctt gac cgc agc tgg gtc cgg ctc tct gtt ggt ctt gaa gac   1152
Met Gly Leu Asp Arg Ser Trp Val Arg Leu Ser Val Gly Leu Glu Asp
    370                 375                 380 gca gat gat ctg gaa gct gat ctt ctc gct tcg ctt aac agc ttg tga   1200
Ala Asp Asp Leu Glu Ala Asp Leu Leu Ala Ser Leu Asn Ser Leu
385                 390                 395

<210> SEQ ID NO 14
<211> LENGTH: 399
<212> TYPE: PRT
<213> ORGANISM: Hyphomonas neptunium
<220> FEATURE:
<221> NAME/KEY: misc_feature
<222> LOCATION: 1..399
<223> OTHER INFORMATION: Hyphomonas neptunium ATCC 15444 (strain)
```

<220> FEATURE:
<223> OTHER INFORMATION: [CDS]:1..1200 from SEQ ID NO 13

<400> SEQUENCE: 14

Met Ala Asp Ala Pro Gly Gly Asp Lys Lys Gly Trp Lys Pro Ala Thr
1               5                   10                  15

Gln Ala Val Arg Gly Gly Leu Met Arg Ser Gln His Gly Glu Ile Ser
            20                  25                  30

Glu Ala Leu Tyr Leu Thr Ser Gly Tyr Ala Tyr Asp Ser Ala Glu Gln
        35                  40                  45

Ala Met Arg Arg Met Ala Gly Glu Glu Gly Phe Val Tyr Ser Arg
    50                  55                  60

Tyr Gly Ser Pro Thr Asn Glu Met Leu Gln Gln Arg Leu Ala Leu Ile
65                  70                  75                  80

Glu Gly Ala Glu Ala Cys Arg Val Thr Gly Ser Gly Met Gly Ala Ile
                85                  90                  95

Ser Ser Ala Ile Leu Ala Pro Leu Lys Ala Gly Asp Arg Val Val Ala
            100                 105                 110

Ala Thr Ala Leu Phe Gly Ser Cys Arg Trp Ile Ile Ala Asn Gln Met
        115                 120                 125

Pro Lys Phe Gly Ile Glu Ala Val Phe Val Asp Gly Ala Asp Leu Asp
    130                 135                 140

Ala Trp Lys Arg Glu Ile Asp Lys Gly Cys Gln Leu Val Leu Ile Glu
145                 150                 155                 160

Ser Pro Ala Asn Pro Leu Leu Asp Gly Val Asp Ile Glu Ala Val Ala
                165                 170                 175

Arg Leu Ala Lys Ala Ala Gly Ala Leu Leu Val Val Asp Asn Val Phe
            180                 185                 190

Ala Thr Pro Val Leu Gln Arg Pro Leu Glu Met Gly Ala Asp Val Ile
        195                 200                 205

Ala Tyr Ser Ala Thr Lys His Met Asp Gly Gln Gly Arg Val Leu Leu
    210                 215                 220

Gly Ala Ile Leu Thr Asp Ala Lys Arg Met Ser Asp Val Tyr Asp Pro
225                 230                 235                 240

Trp Leu Arg His Met Gly Pro Ala Ala Ser Pro Phe Asn Ala Trp Val
                245                 250                 255

Val Leu Lys Gly Leu Glu Thr Met Gln Leu Arg Val Glu Ala Gln Ser
            260                 265                 270

Arg Thr Ala Ala Arg Leu Ala Asp Val Leu Ala Asp His Pro Ala Val
        275                 280                 285

Asn Ala Val Arg Tyr Pro His Arg Lys Asp His Pro His Tyr Glu Val
    290                 295                 300

His Lys Arg Gln Met Lys Ser Gly Gly Thr Leu Leu Ala Leu Ser Leu
305                 310                 315                 320

Lys Gly Gly Gln Asp Ala Ala Phe Arg Phe Leu Asn Gly Leu Gln Leu
                325                 330                 335

Val Asp Ile Cys Asn Asn Leu Gly Asp Thr Lys Ser Leu Ala Cys His
            340                 345                 350

Pro Ser Thr Thr Thr His Arg Ala Leu Ser Asp Glu Asp Gln Ala Ala
        355                 360                 365

Met Gly Leu Asp Arg Ser Trp Val Arg Leu Ser Val Gly Leu Glu Asp
    370                 375                 380

Ala Asp Asp Leu Glu Ala Asp Leu Leu Ala Ser Leu Asn Ser Leu
385                 390                 395

```
<210> SEQ ID NO 15
<211> LENGTH: 1254
<212> TYPE: DNA
<213> ORGANISM: Hyphomonas neptunium
<220> FEATURE:
<221> NAME/KEY: misc_feature
<222> LOCATION: 1..1254
<223> OTHER INFORMATION: Hyphomonas neptunium ATCC 15444 (strain)
<220> FEATURE:
<221> NAME/KEY: misc_feature
<222> LOCATION: 4..9
<223> OTHER INFORMATION: /note="restriction site XbaI"
<220> FEATURE:
<221> NAME/KEY: CDS
<222> LOCATION: 46..1245
<223> OTHER INFORMATION: /transl_table=11
<220> FEATURE:
<221> NAME/KEY: misc_feature
<222> LOCATION: 1246..1251
<223> OTHER INFORMATION: /note="restriction site XhoI"

<400> SEQUENCE: 15
```

| | | |
|---|---|---|
| aaatctagaa ataattttgt ttaactttaa gaaggagata tacat atg gcg gat gca<br>                                                            Met Ala Asp Ala<br>                                                             1 | | 57 |

```
ccc ggc ggc gac aag aag ggc tgg aag cct gcg acc cag gcg gta cgc      105
Pro Gly Gly Asp Lys Lys Gly Trp Lys Pro Ala Thr Gln Ala Val Arg
  5              10                  15                  20 ggc ggc ctg atg cgg tcc cag cat ggg gag att tcc gag gcg ctg tat      153
Gly Gly Leu Met Arg Ser Gln His Gly Glu Ile Ser Glu Ala Leu Tyr
                 25                  30                  35 ctg acc tcc ggc tac gct tac gac tcg gcc gag cag gcg atg cgc cgg      201
Leu Thr Ser Gly Tyr Ala Tyr Asp Ser Ala Glu Gln Ala Met Arg Arg
             40                  45                  50 atg gcg ggc gag gaa gaa ggc ttc gtc tat tcc cgc tat ggc agc ccg      249
Met Ala Gly Glu Glu Glu Gly Phe Val Tyr Ser Arg Tyr Gly Ser Pro
         55                  60                  65 acc aat gag atg ctg caa cag cgc ctc gcg ctg att gaa ggc gcc gaa      297
Thr Asn Glu Met Leu Gln Gln Arg Leu Ala Leu Ile Glu Gly Ala Glu
     70                  75                  80 gcg tgc cgg gtg acg ggc tct ggc atg ggc gcg att tcg tcg gcc atc      345
Ala Cys Arg Val Thr Gly Ser Gly Met Gly Ala Ile Ser Ser Ala Ile
 85                  90                  95                 100 ctg gcg ccg ctt aaa gcg ggc gac cgg gtg gtg gcg gcg acc gcg ctg      393
Leu Ala Pro Leu Lys Ala Gly Asp Arg Val Val Ala Ala Thr Ala Leu
                105                 110                 115 ttt ggc tcg tgc cgc tgg atc att gcc aac cag atg ccg aag ttt ggc      441
Phe Gly Ser Cys Arg Trp Ile Ile Ala Asn Gln Met Pro Lys Phe Gly
            120                 125                 130 atc gag gca gtg ttc gtg gac ggg gcc gat ctt gat gct tgg aag cgc      489
Ile Glu Ala Val Phe Val Asp Gly Ala Asp Leu Asp Ala Trp Lys Arg
        135                 140                 145 gag atc gac aag ggc tgc cag ctg gtg ctg atc gaa agc ccg gcc aat      537
Glu Ile Asp Lys Gly Cys Gln Leu Val Leu Ile Glu Ser Pro Ala Asn
    150                 155                 160 ccg ttg ctc gac ggc gtg gac atc gaa gcg gtc gcc agg ctc gcc aag      585
Pro Leu Leu Asp Gly Val Asp Ile Glu Ala Val Ala Arg Leu Ala Lys
165                 170                 175                 180 gcg gcg ggc gcg ctg ctg gtg gtg gac aat gtg ttt gcc acg ccg gtg      633
Ala Ala Gly Ala Leu Leu Val Val Asp Asn Val Phe Ala Thr Pro Val
                185                 190                 195 ctt cag cgg ccg ctg gaa atg ggc gcc gat gtg atc gcc tat tcg gcc      681
Leu Gln Arg Pro Leu Glu Met Gly Ala Asp Val Ile Ala Tyr Ser Ala
```

|  |  |  |  |  |  |  |  |  |  |  |  |  |  |  |  |
|--|--|--|--|--|--|--|--|--|--|--|--|--|--|--|--|
|  | 200 |  |  |  | 205 |  |  |  | 210 |  |  |  |  |  |  |
| acc | aaa | cat | atg | gac | ggg | cag | ggc | cgc | gtt | ctg | ctg | ggc | gcg | atc | ctg | 729
| Thr | Lys | His | Met | Asp | Gly | Gln | Gly | Arg | Val | Leu | Leu | Gly | Ala | Ile | Leu |
|  |  | 215 |  |  |  | 220 |  |  |  | 225 |  |  |  |  |  |

```
acc aaa cat atg gac ggg cag ggc cgc gtt ctg ctg ggc gcg atc ctg       729
Thr Lys His Met Asp Gly Gln Gly Arg Val Leu Leu Gly Ala Ile Leu
        215                 220                 225 acg gac gcc aag cgg atg agt gat gtg tat gat ccg tgg ctg cgc cat       777
Thr Asp Ala Lys Arg Met Ser Asp Val Tyr Asp Pro Trp Leu Arg His
230                 235                 240 atg ggg ccg gcg gcc tcg ccg ttt aac gcc tgg gta gtg ctg aag ggc       825
Met Gly Pro Ala Ala Ser Pro Phe Asn Ala Trp Val Val Leu Lys Gly
    245                 250                 255                 260 ctt gag acg atg cag ctg cgc gtg gaa gcg cag agc cgc acg gcg gcg       873
Leu Glu Thr Met Gln Leu Arg Val Glu Ala Gln Ser Arg Thr Ala Ala
                265                 270                 275 cgg ctg gcg gat gtt ctg gcc gat cat ccg gcg gtc aat gcc gtg cgc       921
Arg Leu Ala Asp Val Leu Ala Asp His Pro Ala Val Asn Ala Val Arg
            280                 285                 290 tat ccc cac cgc aag gat cac ccg cat tat gag gtg cac aag cgc cag       969
Tyr Pro His Arg Lys Asp His Pro His Tyr Glu Val His Lys Arg Gln
        295                 300                 305 atg aaa tcg ggc ggc acg ctg ctc gcg ctg tcg ctc aag ggc ggg cag      1017
Met Lys Ser Gly Gly Thr Leu Leu Ala Leu Ser Leu Lys Gly Gly Gln
310                 315                 320 gac gcg gcg ttc cgc ttc ctc aac ggg ctg cag ctg gtc gac atc tgc      1065
Asp Ala Ala Phe Arg Phe Leu Asn Gly Leu Gln Leu Val Asp Ile Cys
325                 330                 335                 340 aac aac ctt ggc gat acg aaa tcg ctg gcc tgt cat ccc tcc acc acg      1113
Asn Asn Leu Gly Asp Thr Lys Ser Leu Ala Cys His Pro Ser Thr Thr
                345                 350                 355 acg cac cgc gcg ttg agt gat gag gat cag gcg gcg atg ggg ctt gac      1161
Thr His Arg Ala Leu Ser Asp Glu Asp Gln Ala Ala Met Gly Leu Asp
            360                 365                 370 cgc agc tgg gtc cgg ctc tct gtt ggt ctt gaa gac gca gat gat ctg      1209
Arg Ser Trp Val Arg Leu Ser Val Gly Leu Glu Asp Ala Asp Asp Leu
        375                 380                 385 gaa gct gat ctt ctc gct tcg ctt aac agc ttg tga ctcgagaaa           1254
Glu Ala Asp Leu Leu Ala Ser Leu Asn Ser Leu
390                 395
```

<210> SEQ ID NO 16
<211> LENGTH: 399
<212> TYPE: PRT
<213> ORGANISM: Hyphomonas neptunium
<220> FEATURE:
<221> NAME/KEY: misc_feature
<222> LOCATION: 1..399
<223> OTHER INFORMATION: Hyphomonas neptunium ATCC 15444 (strain)
<220> FEATURE:
<223> OTHER INFORMATION: [CDS]:46..1245 from SEQ ID NO 15

<400> SEQUENCE: 16

```
Met Ala Asp Ala Pro Gly Gly Asp Lys Lys Gly Trp Lys Pro Ala Thr
1               5                   10                  15

Gln Ala Val Arg Gly Gly Leu Met Arg Ser Gln His Gly Glu Ile Ser
            20                  25                  30

Glu Ala Leu Tyr Leu Thr Ser Gly Tyr Ala Tyr Asp Ser Ala Glu Gln
        35                  40                  45

Ala Met Arg Arg Met Ala Gly Glu Glu Gly Phe Val Tyr Ser Arg
    50                  55                  60

Tyr Gly Ser Pro Thr Asn Glu Met Leu Gln Gln Arg Leu Ala Leu Ile
65                  70                  75                  80
```

Glu Gly Ala Glu Ala Cys Arg Val Thr Gly Ser Gly Met Gly Ala Ile
                85                  90                  95

Ser Ser Ala Ile Leu Ala Pro Leu Lys Ala Gly Asp Arg Val Val Ala
            100                 105                 110

Ala Thr Ala Leu Phe Gly Ser Cys Arg Trp Ile Ile Ala Asn Gln Met
            115                 120                 125

Pro Lys Phe Gly Ile Glu Ala Val Phe Val Asp Gly Ala Asp Leu Asp
        130                 135                 140

Ala Trp Lys Arg Glu Ile Asp Lys Gly Cys Gln Leu Val Leu Ile Glu
145                 150                 155                 160

Ser Pro Ala Asn Pro Leu Leu Asp Gly Val Asp Ile Glu Ala Val Ala
                165                 170                 175

Arg Leu Ala Lys Ala Ala Gly Ala Leu Leu Val Val Asp Asn Val Phe
            180                 185                 190

Ala Thr Pro Val Leu Gln Arg Pro Leu Glu Met Gly Ala Asp Val Ile
            195                 200                 205

Ala Tyr Ser Ala Thr Lys His Met Asp Gly Gln Gly Arg Val Leu Leu
        210                 215                 220

Gly Ala Ile Leu Thr Asp Ala Lys Arg Met Ser Asp Val Tyr Asp Pro
225                 230                 235                 240

Trp Leu Arg His Met Gly Pro Ala Ala Ser Pro Phe Asn Ala Trp Val
                245                 250                 255

Val Leu Lys Gly Leu Glu Thr Met Gln Leu Arg Val Glu Ala Gln Ser
            260                 265                 270

Arg Thr Ala Ala Arg Leu Ala Asp Val Leu Ala Asp His Pro Ala Val
            275                 280                 285

Asn Ala Val Arg Tyr Pro His Arg Lys Asp His Pro His Tyr Glu Val
        290                 295                 300

His Lys Arg Gln Met Lys Ser Gly Gly Thr Leu Leu Ala Leu Ser Leu
305                 310                 315                 320

Lys Gly Gly Gln Asp Ala Ala Phe Arg Phe Leu Asn Gly Leu Gln Leu
                325                 330                 335

Val Asp Ile Cys Asn Asn Leu Gly Asp Thr Lys Ser Leu Ala Cys His
            340                 345                 350

Pro Ser Thr Thr Thr His Arg Ala Leu Ser Asp Glu Asp Gln Ala Ala
            355                 360                 365

Met Gly Leu Asp Arg Ser Trp Val Arg Leu Ser Val Gly Leu Glu Asp
        370                 375                 380

Ala Asp Asp Leu Glu Ala Asp Leu Leu Ala Ser Leu Asn Ser Leu
385                 390                 395

<210> SEQ ID NO 17
<211> LENGTH: 386
<212> TYPE: PRT
<213> ORGANISM: Escherichia coli
<220> FEATURE:
<221> NAME/KEY: misc_feature
<222> LOCATION: 1..386
<223> OTHER INFORMATION: Escherichia coli K-12 (strain)
<220> FEATURE:
<223> OTHER INFORMATION: metB

<400> SEQUENCE: 17

Met Thr Arg Lys Gln Ala Thr Ile Ala Val Arg Ser Gly Leu Asn Asp
1               5                   10                  15

Asp Glu Gln Tyr Gly Cys Val Val Pro Pro Ile His Leu Ser Ser Thr
            20                  25                  30

```
Tyr Asn Phe Thr Gly Phe Asn Glu Pro Arg Ala His Asp Tyr Ser Arg
         35                  40                  45

Arg Gly Asn Pro Thr Arg Asp Val Val Gln Arg Ala Leu Ala Glu Leu
 50                  55                  60

Glu Gly Gly Ala Gly Ala Val Leu Thr Asn Thr Gly Met Ser Ala Ile
 65                  70                  75                  80

His Leu Val Thr Thr Val Phe Leu Lys Pro Gly Asp Leu Leu Val Ala
                 85                  90                  95

Pro His Asp Cys Tyr Gly Gly Ser Tyr Arg Leu Phe Asp Ser Leu Ala
                100                 105                 110

Lys Arg Gly Cys Tyr Arg Val Leu Phe Val Asp Gln Gly Asp Glu Gln
                115                 120                 125

Ala Leu Arg Ala Ala Leu Ala Glu Lys Pro Lys Leu Val Leu Val Glu
            130                 135                 140

Ser Pro Ser Asn Pro Leu Leu Arg Val Val Asp Ile Ala Lys Ile Cys
145                 150                 155                 160

His Leu Ala Arg Glu Val Gly Ala Val Ser Val Val Asp Asn Thr Phe
                165                 170                 175

Leu Ser Pro Ala Leu Gln Asn Pro Leu Ala Leu Gly Ala Asp Leu Val
            180                 185                 190

Leu His Ser Cys Thr Lys Tyr Leu Asn Gly His Ser Asp Val Val Ala
        195                 200                 205

Gly Val Val Ile Ala Lys Asp Pro Asp Val Val Thr Glu Leu Ala Trp
    210                 215                 220

Trp Ala Asn Asn Ile Gly Val Thr Gly Gly Ala Phe Asp Ser Tyr Leu
225                 230                 235                 240

Leu Leu Arg Gly Leu Arg Thr Leu Val Pro Arg Met Glu Leu Ala Gln
                245                 250                 255

Arg Asn Ala Gln Ala Ile Val Lys Tyr Leu Gln Thr Gln Pro Leu Val
            260                 265                 270

Lys Lys Leu Tyr His Pro Ser Leu Pro Glu Asn Gln Gly His Glu Ile
        275                 280                 285

Ala Ala Arg Gln Gln Lys Gly Phe Gly Ala Met Leu Ser Phe Glu Leu
    290                 295                 300

Asp Gly Asp Glu Gln Thr Leu Arg Arg Phe Leu Gly Gly Leu Ser Leu
305                 310                 315                 320

Phe Thr Leu Ala Glu Ser Leu Gly Gly Val Glu Ser Leu Ile Ser His
                325                 330                 335

Ala Ala Thr Met Thr His Ala Gly Met Ala Pro Glu Ala Arg Ala Ala
            340                 345                 350

Ala Gly Ile Ser Glu Thr Leu Leu Arg Ile Ser Thr Gly Ile Glu Asp
        355                 360                 365

Gly Glu Asp Leu Ile Ala Asp Leu Glu Asn Gly Phe Arg Ala Ala Asn
    370                 375                 380

Lys Gly
385

<210> SEQ ID NO 18
<211> LENGTH: 403
<212> TYPE: PRT
<213> ORGANISM: Pseudomonas aeruginosa
<220> FEATURE:
<221> NAME/KEY: misc_feature
<222> LOCATION: 1..403
<223> OTHER INFORMATION: Pseudomonas aeruginosa PA01 (strain)
```

```
<220> FEATURE:
<223> OTHER INFORMATION: metZ

<400> SEQUENCE: 18
```

Met Thr Gln Asp Trp Asp Ala Gly Arg Leu Asp Ser Asp Leu Glu Gly
1               5                   10                  15

Ala Ala Phe Asp Thr Leu Ala Val Arg Ala Gly Gln Arg Arg Thr Pro
            20                  25                  30

Glu Gly Glu His Gly Glu Ala Leu Phe Thr Thr Ser Ser Tyr Val Phe
        35                  40                  45

Arg Thr Ala Ala Asp Ala Ala Arg Phe Ala Gly Glu Val Pro Gly
50                  55                  60

Asn Val Tyr Ser Arg Tyr Thr Asn Pro Thr Val Arg Thr Phe Glu Glu
65                  70                  75                  80

Arg Ile Ala Ala Leu Glu Gly Ala Glu Gln Ala Val Ala Thr Ala Ser
                85                  90                  95

Gly Met Ser Ala Ile Leu Ala Leu Val Met Ser Leu Cys Ser Ser Gly
            100                 105                 110

Asp His Val Leu Val Ser Arg Ser Val Phe Gly Ser Thr Ile Ser Leu
        115                 120                 125

Phe Asp Lys Tyr Phe Lys Arg Phe Gly Ile Gln Val Asp Tyr Pro Pro
130                 135                 140

Leu Ser Asp Leu Ala Ala Trp Glu Ala Ala Cys Lys Pro Asn Thr Lys
145                 150                 155                 160

Leu Phe Phe Val Glu Ser Pro Ser Asn Pro Leu Ala Glu Leu Val Asp
                165                 170                 175

Ile Ala Ala Leu Ala Glu Ile Ala His Ala Lys Gly Ala Leu Leu Ala
            180                 185                 190

Val Asp Asn Cys Phe Cys Thr Pro Ala Leu Gln Gln Pro Leu Lys Leu
        195                 200                 205

Gly Ala Asp Val Val Ile His Ser Ala Thr Lys Tyr Ile Asp Gly Gln
210                 215                 220

Gly Arg Gly Met Gly Gly Val Val Ala Gly Arg Gly Glu Gln Met Lys
225                 230                 235                 240

Glu Val Val Gly Phe Leu Arg Thr Ala Gly Pro Thr Leu Ser Pro Phe
                245                 250                 255

Asn Ala Trp Leu Phe Leu Lys Gly Leu Glu Thr Leu Arg Ile Arg Met
            260                 265                 270

Gln Ala His Ser Ala Ser Ala Leu Ala Leu Ala Glu Trp Leu Glu Arg
        275                 280                 285

Gln Pro Gly Ile Glu Arg Val Tyr Tyr Ala Gly Leu Pro Ser His Pro
290                 295                 300

Gln His Glu Leu Ala Arg Arg Gln Gln Ser Gly Phe Gly Ala Val Val
305                 310                 315                 320

Ser Phe Asp Val Lys Gly Gly Arg Asp Ala Ala Trp Arg Phe Ile Asp
                325                 330                 335

Ala Thr Arg Met Val Ser Ile Thr Thr Asn Leu Gly Asp Thr Lys Thr
            340                 345                 350

Thr Ile Ala His Pro Ala Thr Ser His Gly Arg Leu Ser Pro Glu
        355                 360                 365

Asp Arg Ala Arg Ala Gly Ile Gly Asp Ser Leu Ile Arg Val Ala Val
370                 375                 380

Gly Leu Glu Asp Leu Asp Asp Leu Lys Ala Asp Met Ala Arg Gly Leu
385                 390                 395                 400

Ala Ala Leu

<210> SEQ ID NO 19
<211> LENGTH: 425
<212> TYPE: PRT
<213> ORGANISM: Pseudomonas aeruginosa
<220> FEATURE:
<221> NAME/KEY: misc_feature
<222> LOCATION: 1..425
<223> OTHER INFORMATION: Pseudomonas aeruginosa PAO1 (strain)
<220> FEATURE:
<223> OTHER INFORMATION: metY

<400> SEQUENCE: 19

```
Met Lys Leu Glu Thr Leu Ala Val His Ala Gly Tyr Ser Pro Asp Pro
1               5                   10                  15

Thr Thr Arg Ala Val Ala Val Pro Ile Tyr Gln Thr Thr Ser Tyr Ala
            20                  25                  30

Phe Asp Asp Thr Gln His Gly Ala Asp Leu Phe Asp Leu Lys Val Pro
        35                  40                  45

Gly Asn Ile Tyr Thr Arg Ile Met Asn Pro Thr Asn Asp Val Leu Glu
    50                  55                  60

Gln Arg Val Ala Ala Leu Glu Gly Gly Val Gly Ala Leu Ala Val Ala
65                  70                  75                  80

Ser Gly Met Ala Ala Ile Thr Tyr Ala Ile Gln Thr Val Ala Glu Ala
                85                  90                  95

Gly Asp Asn Ile Val Ser Val Ala Lys Leu Tyr Gly Gly Thr Tyr Asn
            100                 105                 110

Leu Leu Ala His Thr Leu Pro Arg Ile Gly Ile Gln Ala Arg Phe Ala
        115                 120                 125

Ala His Asp Asp Val Ala Ala Leu Glu Ala Leu Ile Asp Glu Arg Thr
    130                 135                 140

Lys Ala Val Phe Cys Glu Thr Ile Gly Asn Pro Ala Gly Asn Ile Ile
145                 150                 155                 160

Asp Leu Gln Ala Leu Ala Asp Ala Ala His Arg His Gly Val Pro Leu
                165                 170                 175

Ile Val Asp Asn Thr Val Ala Thr Pro Val Leu Cys Arg Pro Phe Glu
            180                 185                 190

His Gly Ala Asp Ile Val Val His Ser Leu Thr Lys Tyr Met Gly Gly
        195                 200                 205

His Gly Thr Ser Ile Gly Gly Ile Val Val Asp Ser Gly Lys Phe Asp
    210                 215                 220

Trp Ala Ala Asn Lys Ser Arg Phe Pro Leu Leu Asn Thr Pro Asp Pro
225                 230                 235                 240

Ser Tyr His Gly Val Thr Tyr Thr Glu Ala Phe Gly Pro Ala Ala Phe
                245                 250                 255

Ile Gly Arg Cys Arg Val Val Pro Leu Arg Asn Met Gly Ala Ala Leu
            260                 265                 270

Ser Pro Phe Asn Ala Phe Leu Ile Leu Gln Gly Leu Glu Thr Leu Ala
        275                 280                 285

Leu Arg Met Glu Arg His Cys Asp Asn Ala Leu Ala Val Ala Arg Tyr
    290                 295                 300

Leu Gln Gln His Pro Gln Val Ala Trp Val Lys Tyr Ala Gly Leu Ala
305                 310                 315                 320

Asp Asn Pro Glu His Ala Leu Ala Arg Arg Tyr Leu Gly Gly Arg Pro
                325                 330                 335
```

```
Ala Ala Ile Leu Ser Phe Gly Ile Gln Gly Gly Ser Ala Ala Gly Ala
            340                 345                 350

Arg Phe Ile Asp Ala Leu Lys Leu Val Val Arg Leu Val Asn Ile Gly
            355                 360                 365

Asp Ala Lys Ser Leu Ala Cys His Pro Ala Ser Thr Thr His Arg Gln
            370                 375                 380

Leu Asn Ala Glu Glu Leu Ala Arg Ala Gly Val Ser Asp Asp Met Val
385                 390                 395                 400

Arg Leu Ser Ile Gly Ile Glu His Ile Asp Asp Ile Leu Ala Asp Leu
            405                 410                 415

Asp Gln Ala Leu Ala Ala Ala Arg
            420                 425

<210> SEQ ID NO 20
<211> LENGTH: 403
<212> TYPE: PRT
<213> ORGANISM: Pseudomonas putida
<220> FEATURE:
<221> NAME/KEY: misc_feature
<222> LOCATION: 1..403
<223> OTHER INFORMATION: Pseudomonas putida KT2440 (strain)
<220> FEATURE:
<223> OTHER INFORMATION: metZ

<400> SEQUENCE: 20

Met Thr Asp Gln Trp Asp Ala Gly Arg Leu Asp Ser Asp Leu Glu Gly
1               5                   10                  15

Val Gly Phe Asp Thr Leu Ala Val Arg Ala Gly Gln Asn Arg Thr Pro
            20                  25                  30

Glu Gly Glu His Ser Glu Ala Leu Phe Leu Thr Ser Ser Tyr Val Phe
            35                  40                  45

Arg Thr Ala Ala Asp Ala Ala Ala Arg Phe Ala Gly Glu Thr Pro Gly
            50                  55                  60

Asn Val Tyr Ser Arg Tyr Thr Asn Pro Ser Val Arg Ala Phe Glu Glu
65                  70                  75                  80

Arg Leu Ala Ala Met Glu Gly Ala Glu Gln Ala Val Gly Thr Ser Thr
            85                  90                  95

Gly Met Ala Ala Ile Leu Ala Val Val Met Ser Leu Cys Ser Ala Gly
            100                 105                 110

Asp His Val Leu Val Ser Gln Ser Val Phe Gly Ser Thr Ile Ser Leu
            115                 120                 125

Phe Glu Lys Tyr Phe Lys Arg Phe Gly Val Glu Val Asp Tyr Val Pro
            130                 135                 140

Leu Val Asp Leu Thr Gly Trp Glu Lys Ala Ile Lys Ala Asn Thr Lys
145                 150                 155                 160

Leu Leu Ile Val Glu Ser Pro Ser Asn Pro Leu Ala Glu Leu Val Asp
            165                 170                 175

Ile Thr Ala Leu Ser Glu Ile Ala His Ala Gln Gly Ala Met Leu Val
            180                 185                 190

Val Asp Asn Cys Phe Ser Thr Pro Ala Leu Gln Gln Pro Leu Lys Leu
            195                 200                 205

Gly Ala Asp Ile Val Phe His Ser Ala Thr Lys Phe Ile Asp Gly Gln
            210                 215                 220

Gly Arg Cys Met Gly Gly Val Val Ala Gly Arg Thr Glu Gln Met Lys
225                 230                 235                 240

Glu Val Val Gly Phe Leu Arg Thr Ala Gly Pro Thr Leu Ser Pro Phe
```

```
                    245                 250                 255
Asn Ala Trp Ile Phe Thr Lys Gly Leu Glu Thr Leu Arg Leu Arg Met
            260                 265                 270

Arg Ala His Cys Glu Ser Ala Gln Ala Leu Ala Glu Trp Leu Glu Gln
        275                 280                 285

Gln Asp Gly Val Glu Lys Val His Tyr Ala Gly Leu Pro Ser His Pro
    290                 295                 300

Gln His Glu Leu Ala Lys Arg Gln Met Ser Gly Phe Gly Ala Val Val
305                 310                 315                 320

Ser Phe Glu Val Lys Gly Gly Lys Gly Ala Trp Arg Phe Ile Asp
                325                 330                 335

Ala Thr Arg Val Ile Ser Ile Thr Thr Asn Leu Gly Asp Ser Lys Thr
            340                 345                 350

Thr Ile Ala His Pro Ala Thr Ser His Gly Arg Leu Ser Pro Gln
        355                 360                 365

Glu Arg Glu Ala Ala Gly Ile Arg Asp Ser Leu Ile Arg Val Ala Val
    370                 375                 380

Gly Leu Glu Asp Val Ala Asp Leu Gln Ala Asp Leu Ala Arg Gly Leu
385                 390                 395                 400

Ala Ala Leu

<210> SEQ ID NO 21
<211> LENGTH: 386
<212> TYPE: PRT
<213> ORGANISM: Corynebacterium glutamicum
<220> FEATURE:
<221> NAME/KEY: misc_feature
<222> LOCATION: 1..386
<223> OTHER INFORMATION: Corynebacterium glutamicum ATCC 13032 (strain)
<220> FEATURE:
<223> OTHER INFORMATION: metB

<400> SEQUENCE: 21

Met Ser Phe Asp Pro Asn Thr Gln Gly Phe Ser Thr Ala Ser Ile His
1               5                   10                  15

Ala Gly Tyr Glu Pro Asp Asp Tyr Tyr Gly Ser Ile Asn Thr Pro Ile
            20                  25                  30

Tyr Ala Ser Thr Thr Phe Ala Gln Asn Ala Pro Asn Glu Leu Arg Lys
        35                  40                  45

Gly Tyr Glu Tyr Thr Arg Val Gly Asn Pro Thr Ile Val Ala Leu Glu
    50                  55                  60

Gln Thr Val Ala Ala Leu Glu Gly Ala Lys Tyr Gly Arg Ala Phe Ser
65                  70                  75                  80

Ser Gly Met Ala Ala Thr Asp Ile Leu Phe Arg Ile Ile Leu Lys Pro
                85                  90                  95

Gly Asp His Ile Val Leu Gly Asn Asp Ala Tyr Gly Gly Thr Tyr Arg
            100                 105                 110

Leu Ile Asp Thr Val Phe Thr Ala Trp Gly Val Glu Tyr Thr Val Val
        115                 120                 125

Asp Thr Ser Val Val Glu Glu Val Lys Ala Ala Ile Lys Asp Asn Thr
    130                 135                 140

Lys Leu Ile Trp Val Glu Thr Pro Thr Asn Pro Ala Leu Gly Ile Thr
145                 150                 155                 160

Asp Ile Glu Ala Val Ala Lys Leu Thr Glu Gly Thr Asn Ala Lys Leu
                165                 170                 175

Val Val Asp Asn Thr Phe Ala Ser Pro Tyr Leu Gln Gln Pro Leu Lys
```

```
                180                 185                 190
Leu Gly Ala His Ala Val Leu His Ser Thr Thr Lys Tyr Ile Gly Gly
                195                 200                 205

His Ser Asp Val Val Gly Gly Leu Val Val Thr Asn Asp Gln Glu Met
            210                 215                 220

Asp Glu Glu Leu Leu Phe Met Gln Gly Gly Ile Gly Pro Ile Pro Ser
225                 230                 235                 240

Val Phe Asp Ala Tyr Leu Thr Ala Arg Gly Leu Lys Thr Leu Ala Val
                245                 250                 255

Arg Met Asp Arg His Cys Asp Asn Ala Glu Lys Ile Ala Glu Phe Leu
            260                 265                 270

Asp Ser Arg Pro Glu Val Ser Thr Val Leu Tyr Pro Gly Leu Lys Asn
        275                 280                 285

His Pro Gly His Glu Val Ala Ala Lys Gln Met Lys Arg Phe Gly Gly
    290                 295                 300

Met Ile Ser Val Arg Phe Ala Gly Gly Glu Glu Ala Ala Lys Lys Phe
305                 310                 315                 320

Cys Thr Ser Thr Lys Leu Ile Cys Leu Ala Glu Ser Leu Gly Gly Val
                325                 330                 335

Glu Ser Leu Leu Glu His Pro Ala Thr Met Thr His Gln Ser Ala Ala
            340                 345                 350

Gly Ser Gln Leu Glu Val Pro Arg Asp Leu Val Arg Ile Ser Ile Gly
        355                 360                 365

Ile Glu Asp Ile Glu Asp Leu Leu Ala Asp Val Glu Gln Ala Leu Asn
    370                 375                 380

Asn Leu
385

<210> SEQ ID NO 22
<211> LENGTH: 434
<212> TYPE: PRT
<213> ORGANISM: Leptospira interrogans
<220> FEATURE:
<221> NAME/KEY: misc_feature
<222> LOCATION: 1..434
<223> OTHER INFORMATION: Leptospira interrogans serovar Lai str. 56601
      (strain)
<220> FEATURE:
<223> OTHER INFORMATION: met17

<400> SEQUENCE: 22

Met Pro Arg Asn Tyr Lys Pro Glu Thr Ile Ala Leu His Gly Gly Gln
1               5                   10                  15

Ser Pro Asp Pro Ser Thr Leu Ser Arg Ala Val Pro Ile Tyr Gln Thr
            20                  25                  30

Thr Ser Tyr Val Phe Lys Asn Thr Glu His Ala Ala Lys Leu Phe Gly
        35                  40                  45

Leu Gln Glu Phe Gly Asn Ile Tyr Thr Arg Ile Met Asn Pro Thr Thr
    50                  55                  60

Asp Val Leu Glu Gln Arg Ile Ala Ala Leu Glu Gly Val Ala Ala
65                  70                  75                  80

Leu Ala Thr Ala Ser Gly Gln Ala Ala Glu Thr Leu Ala Leu Leu Asn
                85                  90                  95

Ile Val Glu Ala Gly Gln Glu Ile Val Ala Ser Ser Ser Leu Tyr Gly
            100                 105                 110

Gly Thr Tyr Asn Leu Leu His Tyr Thr Phe Pro Lys Leu Gly Ile Lys
        115                 120                 125
```

```
Val His Phe Val Asp Pro Ser Asp Pro Glu Asn Phe Arg Lys Ala Val
    130                 135                 140

Asn Asp Lys Thr Arg Ala Phe Tyr Ala Glu Thr Leu Gly Asn Pro Lys
145                 150                 155                 160

Leu Asn Thr Leu Asn Leu Glu Ala Ile Ala Lys Val Ala His Asp Ser
                165                 170                 175

Glu Val Pro Leu Ile Ile Asp Asn Thr Leu Pro Ser Pro Tyr Leu Val
            180                 185                 190

Asn Pro Ile Glu His Gly Ala Asp Ile Val Val His Ser Leu Thr Lys
        195                 200                 205

Phe Leu Gly Gly His Gly Thr Ser Ile Gly Ile Ile Val Asp Ser
210                 215                 220

Gly Lys Phe Asn Trp Gly Asn Gly Lys Phe Asn Phe Thr Glu Pro
225                 230                 235                 240

Asp Pro Ser Tyr His Gly Leu Lys Phe Trp Glu Val Phe Gly Lys Phe
                245                 250                 255

Glu Pro Phe Gly Gly Val Asn Ile Ala Tyr Ile Ile Lys Ala Lys Val
            260                 265                 270

Gln Gly Leu Arg Asp Met Gly Ala Ser Ile Ser Pro Phe Asn Ala Trp
        275                 280                 285

Gln Ile Leu Gln Gly Val Glu Thr Leu Pro Leu Arg Met Arg Lys His
    290                 295                 300

Ser Glu Asn Ala Leu Ala Val Ala Glu Tyr Leu Thr Lys His Pro Lys
305                 310                 315                 320

Val Ser Trp Val Asn Tyr Pro Gly Leu Lys Met Asp Lys Asn Tyr Ser
                325                 330                 335

Leu Ala Lys Lys Tyr His Lys Lys Asp Leu Tyr Gly Ala Ile Leu Gly
            340                 345                 350

Phe Gly Ile Lys Gly Gly Ala Val Glu Ala Lys Lys Phe Ile Asp Gly
        355                 360                 365

Leu Glu Leu Phe Ser Leu Leu Ala Asn Val Gly Asp Ala Lys Ser Leu
    370                 375                 380

Val Ile His Pro Ala Ser Thr Thr His Gln Gln Leu Thr Pro Glu Glu
385                 390                 395                 400

Gln Leu Ser Ala Gly Val Thr Pro Asp Phe Val Arg Leu Ser Val Gly
                405                 410                 415

Leu Glu Asn Ile Glu Asp Ile Leu Phe Asp Leu Glu Glu Ala Leu Lys
            420                 425                 430

Lys Val

<210> SEQ ID NO 23
<211> LENGTH: 444
<212> TYPE: PRT
<213> ORGANISM: Saccharomyces cerevisiae
<220> FEATURE:
<221> NAME/KEY: misc_feature
<222> LOCATION: 1..444
<223> OTHER INFORMATION: Saccharomyces cerevisiae S288c (strain)
<220> FEATURE:
<223> OTHER INFORMATION: Met17

<400> SEQUENCE: 23

Met Pro Ser His Phe Asp Thr Val Gln Leu His Ala Gly Gln Glu Asn
1               5                   10                  15

Pro Gly Asp Asn Ala His Arg Ser Arg Ala Val Pro Ile Tyr Ala Thr
            20                  25                  30
```

```
Thr Ser Tyr Val Phe Glu Asn Ser Lys His Gly Ser Gln Leu Phe Gly
         35                  40                  45

Leu Glu Val Pro Gly Tyr Val Tyr Ser Arg Phe Gln Asn Pro Thr Ser
 50                  55                  60

Asn Val Leu Glu Glu Arg Ile Ala Ala Leu Glu Gly Gly Ala Ala Ala
 65                  70                  75                  80

Leu Ala Val Ser Ser Gly Gln Ala Ala Gln Thr Leu Ala Ile Gln Gly
                 85                  90                  95

Leu Ala His Thr Gly Asp Asn Ile Val Ser Thr Ser Tyr Leu Tyr Gly
                100                 105                 110

Gly Thr Tyr Asn Gln Phe Lys Ile Ser Phe Lys Arg Phe Gly Ile Glu
            115                 120                 125

Ala Arg Phe Val Glu Gly Asp Asn Pro Glu Glu Phe Glu Lys Val Phe
        130                 135                 140

Asp Glu Arg Thr Lys Ala Val Tyr Leu Glu Thr Ile Gly Asn Pro Lys
145                 150                 155                 160

Tyr Asn Val Pro Asp Phe Glu Lys Ile Val Ala Ile Ala His Lys His
                165                 170                 175

Gly Ile Pro Val Val Asp Asn Thr Phe Gly Ala Gly Gly Tyr Phe
                180                 185                 190

Cys Gln Pro Ile Lys Tyr Gly Ala Asp Ile Val Thr His Ser Ala Thr
            195                 200                 205

Lys Trp Ile Gly Gly His Gly Thr Thr Ile Gly Gly Ile Ile Val Asp
        210                 215                 220

Ser Gly Lys Phe Pro Trp Lys Asp Tyr Pro Glu Lys Phe Pro Gln Phe
225                 230                 235                 240

Ser Gln Pro Ala Glu Gly Tyr His Gly Thr Ile Tyr Asn Glu Ala Tyr
                245                 250                 255

Gly Asn Leu Ala Tyr Ile Val His Val Arg Thr Glu Leu Leu Arg Asp
            260                 265                 270

Leu Gly Pro Leu Met Asn Pro Phe Ala Ser Phe Leu Leu Leu Gln Gly
        275                 280                 285

Val Glu Thr Leu Ser Leu Arg Ala Glu Arg His Gly Glu Asn Ala Leu
        290                 295                 300

Lys Leu Ala Lys Trp Leu Glu Gln Ser Pro Tyr Val Ser Trp Val Ser
305                 310                 315                 320

Tyr Pro Gly Leu Ala Ser His Ser His His Glu Asn Ala Lys Lys Tyr
                325                 330                 335

Leu Ser Asn Gly Phe Gly Gly Val Leu Ser Phe Gly Val Lys Asp Leu
            340                 345                 350

Pro Asn Ala Asp Lys Glu Thr Asp Pro Phe Lys Leu Ser Gly Ala Gln
        355                 360                 365

Val Val Asp Asn Leu Lys Leu Ala Ser Asn Leu Ala Asn Val Gly Asp
        370                 375                 380

Ala Lys Thr Leu Val Ile Ala Pro Tyr Phe Thr Thr His Lys Gln Leu
385                 390                 395                 400

Asn Asp Lys Glu Lys Leu Ala Ser Gly Val Thr Lys Asp Leu Ile Arg
                405                 410                 415

Val Ser Val Gly Ile Glu Phe Ile Asp Asp Ile Ile Ala Asp Phe Gln
            420                 425                 430

Gln Ser Phe Glu Thr Val Phe Ala Gly Gln Lys Pro
        435                 440
```

```
<210> SEQ ID NO 24
<211> LENGTH: 404
<212> TYPE: PRT
<213> ORGANISM: Nocardia farcinica
<220> FEATURE:
<221> NAME/KEY: misc_feature
<222> LOCATION: 1..404
<223> OTHER INFORMATION: Nocardia farcinica IFM 10152 (strain)
<220> FEATURE:
<223> OTHER INFORMATION: metZ

<400> SEQUENCE: 24
```

| Met | Ile | Thr | Gly | Gly | Ala | Phe | Asp | Lys | Pro | Leu | Pro | Glu | Gly | Val | Gly |
|---|---|---|---|---|---|---|---|---|---|---|---|---|---|---|---|
| 1 | | | | 5 | | | | | 10 | | | | | 15 | |

| Pro | Ala | Thr | Leu | Gly | Val | Arg | Gly | Gly | Leu | Arg | Arg | Ser | Gly | Phe | Glu |
|---|---|---|---|---|---|---|---|---|---|---|---|---|---|---|---|
| | | | 20 | | | | | 25 | | | | | 30 | | |

| Glu | Thr | Ala | Glu | Ala | Leu | Tyr | Leu | Thr | Ser | Gly | Phe | Val | Tyr | Glu | Ser |
|---|---|---|---|---|---|---|---|---|---|---|---|---|---|---|---|
| | | 35 | | | | | 40 | | | | | 45 | | | |

| Ala | Glu | Ala | Ala | Glu | Ala | Ala | Phe | Thr | Gly | Glu | Val | Glu | His | Phe | Val |
|---|---|---|---|---|---|---|---|---|---|---|---|---|---|---|---|
| | 50 | | | | | 55 | | | | | 60 | | | | |

| Tyr | Ser | Arg | Tyr | Gly | Asn | Pro | Thr | Val | Ala | Met | Phe | Glu | Glu | Arg | Ile |
|---|---|---|---|---|---|---|---|---|---|---|---|---|---|---|---|
| 65 | | | | | 70 | | | | | 75 | | | | | 80 |

| Arg | Leu | Met | Asp | Gly | Ala | Glu | Ala | Ala | Phe | Ala | Thr | Ala | Ser | Gly | Met |
|---|---|---|---|---|---|---|---|---|---|---|---|---|---|---|---|
| | | | | 85 | | | | | 90 | | | | | 95 | |

| Ser | Ala | Val | Phe | Thr | Ala | Leu | Gly | Ala | Leu | Leu | Gly | Ala | Gly | Asp | Arg |
|---|---|---|---|---|---|---|---|---|---|---|---|---|---|---|---|
| | | | | 100 | | | | | 105 | | | | | 110 | |

| Leu | Val | Ala | Ala | Arg | Ser | Leu | Phe | Gly | Ser | Cys | Phe | Val | Val | Cys | Asn |
|---|---|---|---|---|---|---|---|---|---|---|---|---|---|---|---|
| | | | 115 | | | | | 120 | | | | | 125 | | |

| Glu | Ile | Leu | Pro | Arg | Trp | Gly | Val | Glu | Thr | Val | Phe | Val | Asp | Gly | Glu |
|---|---|---|---|---|---|---|---|---|---|---|---|---|---|---|---|
| | 130 | | | | | 135 | | | | | 140 | | | | |

| Asp | Leu | Asp | Gln | Trp | Glu | Arg | Ala | Leu | Ser | Val | Pro | Thr | Ala | Ala | Val |
|---|---|---|---|---|---|---|---|---|---|---|---|---|---|---|---|
| 145 | | | | | 150 | | | | | 155 | | | | | 160 |

| Phe | Phe | Glu | Thr | Pro | Ala | Asn | Pro | Met | Gln | Thr | Leu | Val | Asp | Val | Arg |
|---|---|---|---|---|---|---|---|---|---|---|---|---|---|---|---|
| | | | | 165 | | | | | 170 | | | | | 175 | |

| Arg | Val | Thr | Glu | Leu | Ala | His | Ala | Ala | Gly | Ala | Lys | Val | Val | Leu | Asp |
|---|---|---|---|---|---|---|---|---|---|---|---|---|---|---|---|
| | | | 180 | | | | | 185 | | | | | 190 | | |

| Asn | Val | Phe | Ala | Thr | Pro | Leu | Leu | Gln | Lys | Gly | Phe | Asp | Leu | Gly | Ala |
|---|---|---|---|---|---|---|---|---|---|---|---|---|---|---|---|
| | | 195 | | | | | 200 | | | | | 205 | | | |

| Asp | Val | Val | Val | Tyr | Ser | Gly | Thr | Lys | His | Ile | Asp | Gly | Gln | Gly | Arg |
|---|---|---|---|---|---|---|---|---|---|---|---|---|---|---|---|
| 210 | | | | | 215 | | | | | 220 | | | | | |

| Val | Leu | Gly | Gly | Ala | Ile | Leu | Gly | Asp | Arg | Glu | Tyr | Ile | Asp | Gly | Pro |
|---|---|---|---|---|---|---|---|---|---|---|---|---|---|---|---|
| 225 | | | | | 230 | | | | | 235 | | | | | 240 |

| Val | Lys | Thr | Leu | Met | Arg | His | Thr | Gly | Pro | Ala | Leu | Ser | Pro | Phe | Asn |
|---|---|---|---|---|---|---|---|---|---|---|---|---|---|---|---|
| | | | | 245 | | | | | 250 | | | | | 255 | |

| Ala | Trp | Thr | Leu | Leu | Lys | Gly | Leu | Glu | Thr | Met | Pro | Leu | Arg | Val | Arg |
|---|---|---|---|---|---|---|---|---|---|---|---|---|---|---|---|
| | | | 260 | | | | | 265 | | | | | 270 | | |

| His | Ser | Thr | Glu | Ser | Ala | Leu | Arg | Ile | Ala | Arg | Phe | Leu | Glu | Ser | Asn |
|---|---|---|---|---|---|---|---|---|---|---|---|---|---|---|---|
| | | 275 | | | | | 280 | | | | | 285 | | | |

| Pro | Ala | Val | Ser | Trp | Val | Lys | Tyr | Pro | Phe | Leu | Glu | Ser | His | Pro | Gln |
|---|---|---|---|---|---|---|---|---|---|---|---|---|---|---|---|
| 290 | | | | | 295 | | | | | 300 | | | | | |

| Tyr | Asp | Leu | Ala | Arg | Ala | Gln | Met | Ser | Gly | Gly | Gly | Thr | Val | Val | Thr |
|---|---|---|---|---|---|---|---|---|---|---|---|---|---|---|---|
| 305 | | | | | 310 | | | | | 315 | | | | | 320 |

| Phe | Glu | Leu | Lys | Ala | Ala | Glu | Gly | Glu | Ala | Lys | Lys | Arg | Ala | Phe | Glu |
|---|---|---|---|---|---|---|---|---|---|---|---|---|---|---|---|
| | | | | 325 | | | | | 330 | | | | | 335 | |

| Val | Leu | Asp | Arg | Leu | Arg | Ile | Ile | Asp | Ile | Ser | Asn | Asn | Leu | Gly | Asp |
|---|---|---|---|---|---|---|---|---|---|---|---|---|---|---|---|
| | | | | 340 | | | | | 345 | | | | | 350 | |

```
Ala Lys Thr Leu Ile Thr His Pro Ala Thr Thr His Arg Ala Met
        355                 360                 365

Gly Pro Glu Gly Arg Ala Gly Ile Gly Leu Thr Asp Gly Val Val Arg
370                 375                 380

Ile Ser Val Gly Leu Glu Asp Val Asp Asp Leu Leu Ser Asp Leu Glu
385                 390                 395                 400

His Ala Leu Ser

<210> SEQ ID NO 25
<211> LENGTH: 395
<212> TYPE: PRT
<213> ORGANISM: Bradyrhizobium japonicum
<220> FEATURE:
<221> NAME/KEY: misc_feature
<222> LOCATION: 1..395
<223> OTHER INFORMATION: Bradyrhizobium japonicum USDA 6 (strain)
<220> FEATURE:
<223> OTHER INFORMATION: metZ

<400> SEQUENCE: 25

Met Ser Lys Ser Thr Ala Asn Tyr Arg Pro Glu Thr Arg Leu Val His
1               5                   10                  15

Ser Gly Thr Leu Arg Ser Gln Tyr Gly Glu Thr Ser Glu Ala Leu Phe
            20                  25                  30

Leu Thr Gln Gly Tyr Val Tyr Asn Ser Ala Glu Cys Glu Ala Arg
        35                  40                  45

Phe Lys Gly Glu Asp Pro Gly Phe Ile Tyr Ser Arg Tyr Ser Asn Pro
    50                  55                  60

Thr Ile Ala Met Phe Glu Arg Arg Met Ile Glu Leu Glu Gly Ala Glu
65                  70                  75                  80

Ala Ala Arg Ser Ala Ala Thr Gly Met Ala Ala Val Thr Thr Ala Ile
                85                  90                  95

Leu Ala Pro Leu Lys Ala Gly Asp His Val Val Ala Ser Arg Ala Leu
            100                 105                 110

Phe Gly Ser Cys Leu Tyr Val Ile Gln Asp Leu Leu Pro Arg Tyr Gly
        115                 120                 125

Ile Glu Thr Thr Leu Val Asp Gly Leu Asp Leu Asp Gln Trp Gln Arg
    130                 135                 140

Ala Leu Arg Pro Asn Thr Lys Thr Phe Phe Leu Glu Ser Pro Thr Asn
145                 150                 155                 160

Pro Thr Leu Asp Val Leu Asp Ile Pro Gly Ile Ala Glu Ile Ala His
                165                 170                 175

Ser Gly Gly Ala Arg Leu Val Val Asp Asn Val Phe Ala Thr Pro Ile
            180                 185                 190

Trp Gln Ser Pro Leu Ala Leu Gly Ala Asp Val Val Val Tyr Ser Ala
        195                 200                 205

Thr Lys His Ile Asp Gly Gln Gly Arg Cys Leu Gly Gly Ile Ile Leu
    210                 215                 220

Ser Ser Glu Ala Phe Ile Ala Glu His Ile His Asn Phe Met Arg Gln
225                 230                 235                 240

Thr Gly Pro Ser Ile Ser Pro Phe Asn Ala Trp Val Leu Leu Lys Gly
                245                 250                 255

Leu Glu Thr Leu Gly Val Arg Val Arg Ala Gln Thr Glu Thr Ala Gly
            260                 265                 270

Arg Ile Ala Asp Val Leu Ala Ser His Pro Lys Ile Ser Arg Leu Val
        275                 280                 285
```

Tyr Pro Gly Arg Ala Asp His Pro Gln Ala Ala Leu Val Lys Lys Gln
            290                 295                 300

Met Arg Gly Gly Ser Thr Leu Val Gly Phe Glu Val Lys Gly Gly Lys
305                 310                 315                 320

Gln Gly Ala Phe Arg Val Leu Asn Glu Leu Lys Leu Ala Lys Ile Ser
                325                 330                 335

Asn Asn Leu Gly Asp Ala Lys Ser Leu Val Thr His Pro Ala Thr Thr
            340                 345                 350

Thr His Gln Arg Leu Lys Pro Glu Asp Arg Ala Ala Leu Gly Ile Ser
        355                 360                 365

Glu Gly Phe Ile Arg Phe Ser Ala Gly Leu Glu His Ala Asp Asp Leu
    370                 375                 380

Ile Glu Asp Leu Thr Ala Ala Leu Glu Lys Ala
385                 390                 395

<210> SEQ ID NO 26
<211> LENGTH: 383
<212> TYPE: PRT
<213> ORGANISM: Methylococcus capsulatus
<220> FEATURE:
<221> NAME/KEY: misc_feature
<222> LOCATION: 1..383
<223> OTHER INFORMATION: Methylococcus capsulatus str. Bath (strain)
<220> FEATURE:
<223> OTHER INFORMATION: metZ

<400> SEQUENCE: 26

Met Glu Thr Arg Ala Val Arg Ala Gly Gln Arg Arg Thr Met Glu Gln
1               5                   10                  15

Glu His Ala Glu Pro Ile Phe Ala Thr Ser Ser Tyr Val Phe Ala Ser
            20                  25                  30

Ala Ala Glu Ala Ala Glu Arg Phe Ala Gly Lys Ala Ala Gly Asn Ile
        35                  40                  45

Tyr Ser Arg Phe Thr Asn Pro Thr Val Arg Thr Phe Glu Glu Arg Leu
    50                  55                  60

Ala Ala Leu Glu Gly Gly Glu Arg Cys Val Ala Val Gly Ser Gly Met
65                  70                  75                  80

Ala Ala Ile Ala Ser Thr Ala Phe Gly Leu Leu Lys Ala Gly Asp His
                85                  90                  95

Val Val Cys Ser Arg Ser Val Phe Gly Asn Thr Thr Leu Leu Phe Gln
            100                 105                 110

Asn Tyr Leu Ala Lys Phe Gly Val Pro Thr Thr Phe Val Gly Leu Thr
        115                 120                 125

Asp Tyr Asp Gly Trp Ala Ala Ala Ile Arg Pro Glu Thr Arg Phe Leu
    130                 135                 140

Phe Ile Glu Thr Pro Ser Asn Pro Leu Thr Glu Ile Ala Asp Ile Pro
145                 150                 155                 160

Arg Leu Ala Glu Ile Ala His Ser Arg Gly Cys Leu Leu Val Val Asp
                165                 170                 175

Asn Cys Phe Cys Thr Pro Ala Leu Gln Arg Pro Leu Ala Leu Gly Ala
            180                 185                 190

Asp Ile Val Ile His Ser Ala Thr Lys Tyr Leu Asp Gly Gln Gly Arg
        195                 200                 205

Cys Val Gly Gly Ala Ile Val Gly Gly Arg Glu Leu Leu Asp Ala Glu
    210                 215                 220

Ile Tyr Pro Phe Leu Arg Thr Gly Gly Pro Ser Met Ser Pro Phe Asn

```
                225                 230                 235                 240
Ala Trp Val Phe Leu Lys Gly Leu Glu Thr Leu Asn Leu Arg Met Lys
                    245                 250                 255

Ala His Cys Glu Asn Ala Leu Gly Leu Ala Arg Trp Leu Glu Ala Gln
                    260                 265                 270

Pro Trp Val Glu Arg Val His Tyr Pro Gly Leu Ala Ser His Pro Gln
                    275                 280                 285

His Glu Leu Ala Ala Arg Gln Gln Ser Gly Phe Gly Gly Ile Val Ser
                    290                 295                 300

Phe Glu Val Lys Gly Gly Gln Glu Ala Ala Trp Arg Leu Ile Asp Ser
305                 310                 315                 320

Thr Arg Leu Leu Ser Ile Thr Gly Asn Leu Gly Asp Ala Lys Thr Thr
                    325                 330                 335

Ile Thr His Pro Ala Thr Thr Thr His Gly Arg Leu Ser Pro Glu Ala
                    340                 345                 350

Arg Ala Ala Ala Gly Ile Ala Asp Gly Leu Ile Arg Ile Ala Val Gly
                    355                 360                 365

Leu Glu Asn Leu Ala Asp Ile Gln Ala Asp Leu Ala Arg Phe Ala
                    370                 375                 380

<210> SEQ ID NO 27
<211> LENGTH: 392
<212> TYPE: PRT
<213> ORGANISM: Methylobacillus flagellatus
<220> FEATURE:
<221> NAME/KEY: misc_feature
<222> LOCATION: 1..392
<223> OTHER INFORMATION: Methylobacillus flagellatus KT (strain)
<220> FEATURE:
<223> OTHER INFORMATION: MFLA_RS08660

<400> SEQUENCE: 27

Met Ser Gln His Glu Trp His Ala Glu Thr Leu Gly Val Arg Ala Gly
1               5                   10                  15

Ser Glu His Thr Pro Phe Gly Glu Asn Ser Glu Ala Met Phe Leu Thr
                20                  25                  30

Ser Ser Phe Val Phe Glu Asn Ala Ala Gln Ala Ala Arg Phe Gly
            35                  40                  45

Gly Gln Glu Pro Gly Asn Ile Tyr Ser Arg Phe Thr Asn Pro Thr Val
    50                  55                  60

Ser Met Phe Gln Asn Lys Leu Ala Ala Leu Glu Gly Ala Glu Phe Cys
65                  70                  75                  80

Val Ala Thr Ser Ser Gly Met Ser Ala Ile Leu Ala Cys Val Met Gly
                85                  90                  95

Val Cys Ser Ala Gly Asp His Val Val Ala Ser Arg Ser Ile Phe Gly
                100                 105                 110

Thr Ser Val Gln Leu Phe Ser Asn Ile Leu Lys Arg Trp Gly Leu Glu
                115                 120                 125

Thr Thr Phe Val Gln Leu Ser Asp Pro Glu Ala Trp Thr Ala Ala Val
                130                 135                 140

Lys Pro Asn Thr Lys Leu Phe Phe Leu Glu Thr Pro Ser Asn Pro Leu
145                 150                 155                 160

Thr Glu Ile Cys Asp Ile Ala Val Val Ala Glu Ile Ala His Gln Ala
                165                 170                 175

Gly Ala Leu Leu Ala Val Asp Asn Cys Phe Cys Thr Pro Ala Leu Gln
                180                 185                 190
```

```
Lys Pro Leu Ala Leu Gly Ala Asp Ile Val Val His Ser Ala Thr Lys
            195                 200                 205

Tyr Ile Asp Gly Gln Gly Arg Cys Leu Gly Gly Ala Val Leu Gly Arg
            210                 215                 220

Lys Asp Val Leu Glu Pro Val Tyr Gly Phe Leu Arg Thr Ala Gly Pro
225                 230                 235                 240

Thr Met Ser Ala Phe Asn Ala Trp Val Phe Leu Lys Gly Leu Glu Thr
                245                 250                 255

Leu His Leu Arg Met Glu Ala His Ala Arg Asn Ala Leu Ala Leu Ala
            260                 265                 270

Gln Trp Leu Glu Gln Gln Pro Arg Val Glu Arg Val Tyr Tyr Pro Gly
        275                 280                 285

Leu Pro Ser His Pro Gln Tyr Ala Leu Ala Gln Lys Gln Gln Lys Ser
    290                 295                 300

Gly Gly Ala Ile Val Ser Phe Asp Val Lys Gly Gly Gln Pro Ala Ala
305                 310                 315                 320

Trp His Leu Ile Asp Ala Thr Arg Met Leu Ser Ile Thr Ala Asn Leu
                325                 330                 335

Gly Asp Ala Lys Ser Thr Ile Thr His Pro Ala Thr Thr Thr His Ser
            340                 345                 350

Arg Val Ser Ala Glu Ala Arg Ala Ala Gly Ile Gly Asp Gly Leu
        355                 360                 365

Val Arg Ile Ala Val Gly Leu Glu His Ile Asp Asp Ile Lys Ala Asp
    370                 375                 380

Leu Ala Trp Leu Gly His Gln Asp
385                 390

<210> SEQ ID NO 28
<211> LENGTH: 391
<212> TYPE: PRT
<213> ORGANISM: Nitrosomonas europaea
<220> FEATURE:
<221> NAME/KEY: misc_feature
<222> LOCATION: 1..391
<223> OTHER INFORMATION: Nitrosomonas europaea ATCC 19718 (strain)
<220> FEATURE:
<223> OTHER INFORMATION: metZ

<400> SEQUENCE: 28

Met Thr Asn Asp Leu Asp Pro Glu Thr Leu Ala Ile His Thr Gly Val
1               5                   10                  15

His Arg Ser Gln Phe Asn Glu His Ser Glu Ser Leu Tyr Leu Thr Ser
            20                  25                  30

Ser Phe Val Phe Asp Ser Ala Ala Gln Ala Ala Arg Phe Ser Gly
        35                  40                  45

Gln Glu Pro Gly Asn Ile Tyr Ser Arg Phe Thr Asn Pro Thr Val Thr
    50                  55                  60

Ala Met Gln Glu Arg Leu Ala Val Leu Glu Gly Ala Glu Ala Cys Ile
65                  70                  75                  80

Ala Thr Ala Ser Gly Met Ser Ala Ile Leu Thr Cys Val Met Gly Leu
                85                  90                  95

Leu Ser Ala Gly Asp His Ile Val Ala Ser Arg Ser Leu Phe Gly Ser
            100                 105                 110

Thr Val Ser Leu Phe Asn Asn Ile Leu Ser Arg Phe Gly Ile Gln Thr
        115                 120                 125

Thr Phe Val Ser Ala Thr Asp Pro Ala Glu Trp Gln Ala Ala Val Arg
    130                 135                 140
```

-continued

```
Pro Asn Thr Arg Leu Phe Phe Leu Glu Thr Pro Ser Asn Pro Leu Thr
145                 150                 155                 160

Glu Ile Ser Asp Ile Ala Ala Leu Ala Glu Ile Ala Lys Arg Ala Gly
                165                 170                 175

Val Trp Leu Ala Val Asp Asn Cys Phe Cys Thr Pro Ile Ile Gln Gln
            180                 185                 190

Pro Leu Lys Leu Gly Ala Asp Leu Val Ile His Ser Ala Thr Lys Tyr
        195                 200                 205

Leu Asp Gly Gln Gly Arg Val Leu Gly Gly Ala Ile Leu Gly Lys Arg
    210                 215                 220

Asp Leu Leu Met Asp Ser Gly Ile Phe Ser Phe Leu Arg Thr Ala Gly
225                 230                 235                 240

Pro Ser Leu Ser Ala Phe Asn Ala Trp Ile Ile Leu Lys Gly Met Glu
                245                 250                 255

Thr Leu Ser Leu Arg Val Lys Ala His Ser Asp His Ala Leu Glu Val
                260                 265                 270

Ala Arg Trp Leu Glu Thr His Pro Arg Val Gly Arg Val Phe Tyr Pro
            275                 280                 285

Gly Leu Pro Ser His Pro Gln His Glu Leu Ala Met Arg Gln Gln Lys
        290                 295                 300

Thr Gly Gly Gly Ile Val Ser Phe Glu Val Lys Gly Gly Arg Glu Ala
305                 310                 315                 320

Ala Trp Arg Val Val Asp Ala Ala Arg Leu Met Ser Ile Thr Ala Asn
                325                 330                 335

Leu Gly Asp Thr Lys Ser Thr Leu Thr His Pro Ala Thr Thr Thr His
                340                 345                 350

Gly Arg Ile Ser Gln Glu Ala Arg Glu Ala Ala Gly Ile Arg Asp Gly
            355                 360                 365

Leu Leu Arg Ile Ala Val Gly Leu Glu Ser Pro Asp Asp Leu Lys Ala
        370                 375                 380

Asp Leu Ala Arg Gly Leu Gln
385                 390
```

<210> SEQ ID NO 29
<211> LENGTH: 386
<212> TYPE: PRT
<213> ORGANISM: Klebsiella pneumoniae
<220> FEATURE:
<221> NAME/KEY: misc_feature
<222> LOCATION: 1..386
<223> OTHER INFORMATION: Klebsiella pneumoniae subsp. pneumoniae MGH
    78578 (strain)
<220> FEATURE:
<223> OTHER INFORMATION: metB

<400> SEQUENCE: 29

```
Met Thr Arg Lys Gln Ala Thr Ile Ala Val Arg Ser Gly Leu Asn Asp
1               5                   10                  15

Asp Glu Gln Tyr Gly Cys Val Val Pro Ile His Leu Ser Ser Thr
                20                  25                  30

Tyr Asn Phe Thr Gly Phe Asn Glu Pro Arg Ala His Asp Tyr Ser Arg
            35                  40                  45

Arg Gly Asn Pro Thr Arg Asp Val Val Gln Arg Ala Leu Ala Glu Leu
        50                  55                  60

Glu Gly Gly Ala Gly Ala Val Leu Thr Asn Thr Gly Met Ser Ala Ile
65                  70                  75                  80
```

```
Leu Leu Val Thr Thr Val Phe Leu Lys Pro Gly Asp Leu Leu Val Ala
             85                  90                  95

Pro His Asp Cys Tyr Gly Gly Ser Tyr Arg Leu Phe Asp Ser Leu Ala
        100                 105                 110

Lys Arg Gly Cys Tyr Arg Val Gln Phe Val Asp Gln Ser Asp Glu Gln
    115                 120                 125

Ala Leu Arg Ala Ala Leu Ala Glu Lys Pro Lys Leu Val Leu Val Glu
130                 135                 140

Ser Pro Ser Asn Pro Leu Leu Arg Val Val Asp Ile Ala Lys Ile Cys
145                 150                 155                 160

Gly Leu Ala Arg Glu Ala Gly Ala Ile Ser Val Val Asp Asn Thr Phe
                165                 170                 175

Leu Ser Pro Ala Leu Gln Asn Pro Leu Ala Leu Gly Ala Asp Leu Val
            180                 185                 190

Leu His Ser Cys Thr Lys Tyr Leu Asn Gly His Ser Asp Val Val Ala
        195                 200                 205

Gly Val Val Ile Ala Lys Asp Pro Ala Thr Val Thr Glu Leu Ala Trp
    210                 215                 220

Trp Ala Asn Asn Ile Gly Val Thr Gly Ser Ala Phe Asp Ser Tyr Leu
225                 230                 235                 240

Leu Leu Arg Gly Leu Arg Thr Leu Ser Pro Arg Met Glu Val Ala Gln
                245                 250                 255

Arg Asn Ala Leu Ala Ile Val Glu Tyr Leu Lys Thr Gln Pro Leu Val
            260                 265                 270

Lys Lys Leu Tyr His Pro Ser Leu Pro Glu Asn Gln Gly His Glu Ile
        275                 280                 285

Ala Ala Arg Gln Gln Lys Gly Phe Gly Ala Met Leu Ser Phe Glu Leu
    290                 295                 300

Asp Gly Asp Glu Gln Thr Leu Arg Arg Phe Leu Ser Gly Leu Ser Leu
305                 310                 315                 320

Phe Thr Leu Ala Glu Ser Leu Gly Gly Val Glu Ser Leu Ile Ser His
                325                 330                 335

Ala Ala Thr Met Thr His Ala Gly Met Ala Pro Glu Ala Arg Ala Ala
            340                 345                 350

Ala Gly Ile Ser Glu Thr Leu Leu Arg Ile Ser Thr Gly Ile Glu Asp
        355                 360                 365

Gly Glu Asp Leu Ile Ala Asp Leu Glu Asn Gly Phe Arg Ala Ala Asn
    370                 375                 380

Glu Glu
385

<210> SEQ ID NO 30
<211> LENGTH: 373
<212> TYPE: PRT
<213> ORGANISM: Bacillus subtilis
<220> FEATURE:
<221> NAME/KEY: misc_feature
<222> LOCATION: 1..373
<223> OTHER INFORMATION: Bacillus subtilis subsp. subtilis str. 168
      (strain)
<220> FEATURE:
<223> OTHER INFORMATION: metI

<400> SEQUENCE: 30

Met Ser Gln His Val Glu Thr Lys Leu Ala Gln Ile Gly Asn Arg Ser
1               5                   10                  15

Asp Glu Val Thr Gly Thr Val Ser Ala Pro Ile Tyr Leu Ser Thr Ala
```

```
                    20                  25                  30

Tyr Arg His Arg Gly Ile Gly Glu Ser Thr Gly Phe Asp Tyr Val Arg
            35                  40                  45

Thr Lys Asn Pro Thr Arg Gln Leu Val Glu Asp Ala Ile Ala Asn Leu
        50                  55                  60

Glu Asn Gly Ala Arg Gly Leu Ala Phe Ser Ser Gly Met Ala Ala Ile
    65                  70                  75                  80

Gln Thr Ile Met Ala Leu Phe Lys Ser Gly Asp Glu Leu Ile Val Ser
                    85                  90                  95

Ser Asp Leu Tyr Gly Gly Thr Tyr Arg Leu Phe Glu Asn Glu Trp Lys
                100                 105                 110

Lys Tyr Gly Leu Thr Phe His Tyr Asp Asp Phe Ser Asp Glu Asp Cys
                115                 120                 125

Leu Arg Ser Lys Ile Thr Pro Asn Thr Lys Ala Val Phe Val Glu Thr
            130                 135                 140

Pro Thr Asn Pro Leu Met Gln Glu Ala Asp Ile Glu His Ile Ala Arg
    145                 150                 155                 160

Ile Thr Lys Glu His Gly Leu Leu Leu Ile Val Asp Asn Thr Phe Tyr
                    165                 170                 175

Thr Pro Val Leu Gln Arg Pro Leu Glu Leu Gly Ala Asp Ile Val Ile
                180                 185                 190

His Ser Ala Thr Lys Tyr Leu Gly Gly His Asn Asp Leu Leu Ala Gly
                195                 200                 205

Leu Val Val Val Lys Asp Glu Arg Leu Gly Glu Glu Met Phe Gln His
            210                 215                 220

Gln Asn Ala Ile Gly Ala Val Leu Pro Pro Phe Asp Ser Trp Leu Leu
    225                 230                 235                 240

Met Arg Gly Met Lys Thr Leu Ser Leu Arg Met Arg Gln His Gln Ala
                    245                 250                 255

Asn Ala Gln Glu Leu Ala Ala Phe Leu Glu Glu Gln Glu Glu Ile Ser
                260                 265                 270

Asp Val Leu Tyr Pro Gly Lys Gly Gly Met Leu Ser Phe Arg Leu Gln
                275                 280                 285

Lys Glu Glu Trp Val Asn Pro Phe Leu Lys Ala Leu Lys Thr Ile Cys
        290                 295                 300

Phe Ala Glu Ser Leu Gly Gly Val Glu Ser Phe Ile Thr Tyr Pro Ala
    305                 310                 315                 320

Thr Gln Thr His Met Asp Ile Pro Glu Glu Ile Arg Ile Ala Asn Gly
                    325                 330                 335

Val Cys Asn Arg Leu Leu Arg Phe Ser Val Gly Ile Glu His Ala Glu
                340                 345                 350

Asp Leu Lys Glu Asp Leu Lys Gln Ala Leu Cys Gln Val Lys Glu Gly
                355                 360                 365

Ala Val Ser Phe Glu
        370

<210> SEQ ID NO 31
<211> LENGTH: 386
<212> TYPE: PRT
<213> ORGANISM: Shigella flexneri
<220> FEATURE:
<221> NAME/KEY: misc_feature
<222> LOCATION: 1..386
<223> OTHER INFORMATION: Shigella flexneri 2a str. 2457T (strain)
<220> FEATURE:
<223> OTHER INFORMATION: metB
```

-continued

<400> SEQUENCE: 31

```
Met Thr Arg Lys Gln Ala Thr Ile Ala Val Arg Ser Gly Leu Asn Asp
1               5                   10                  15

Asp Glu Gln Tyr Gly Cys Val Val Pro Pro Ile His Leu Ser Ser Thr
            20                  25                  30

Tyr Asn Phe Thr Gly Phe Asn Glu Pro Arg Ala His Asp Tyr Ser Arg
        35                  40                  45

Arg Gly Asn Pro Thr Arg Asp Val Val Gln Arg Ala Leu Ala Glu Leu
    50                  55                  60

Glu Gly Gly Ala Gly Ala Val Leu Thr Asn Thr Gly Met Ser Ala Ile
65                  70                  75                  80

His Leu Val Thr Thr Val Phe Leu Lys Pro Gly Asp Leu Leu Val Ala
                85                  90                  95

Pro His Asp Cys Tyr Gly Gly Ser Tyr Arg Leu Phe Asp Ser Leu Ala
            100                 105                 110

Lys Arg Gly Cys Tyr Arg Val Leu Phe Val Asp Gln Gly Asp Glu Gln
        115                 120                 125

Ala Leu Arg Ala Ala Leu Ala Glu Lys Pro Lys Leu Val Leu Val Glu
    130                 135                 140

Ser Pro Ser Asn Pro Leu Leu Arg Val Val Asp Ile Ala Lys Ile Cys
145                 150                 155                 160

His Leu Ala Arg Glu Val Gly Ala Val Ser Val Val Asp Asn Thr Phe
                165                 170                 175

Leu Ser Pro Ala Leu Gln Asn Pro Leu Ala Leu Gly Ala Asp Leu Val
            180                 185                 190

Leu His Ser Cys Thr Lys Tyr Leu Asn Gly His Ser Asp Val Val Ala
        195                 200                 205

Gly Val Val Ile Ala Lys Asp Pro Asp Val Val Thr Glu Leu Ala Trp
    210                 215                 220

Trp Ala Asn Asn Ile Gly Val Thr Gly Gly Ala Phe Asp Ser Tyr Leu
225                 230                 235                 240

Leu Leu Arg Gly Leu Arg Thr Leu Val Pro Arg Met Glu Leu Ala Gln
                245                 250                 255

Arg Asn Ala Gln Ala Ile Val Lys Tyr Leu Gln Thr Gln Pro Leu Val
            260                 265                 270

Lys Lys Leu Tyr His Pro Ser Leu Pro Glu Asn Gln Gly His Glu Ile
        275                 280                 285

Ala Ala Arg Gln Gln Lys Gly Phe Gly Ala Met Leu Ser Phe Glu Leu
    290                 295                 300

Asp Gly Asp Glu Gln Thr Leu Cys Arg Phe Leu Gly Gly Leu Ser Leu
305                 310                 315                 320

Phe Thr Leu Ala Glu Ser Leu Gly Gly Val Glu Ser Leu Ile Ser His
                325                 330                 335

Ala Ala Thr Met Thr His Ala Gly Met Ala Pro Glu Ala Arg Ala Ala
            340                 345                 350

Ala Gly Ile Ser Glu Thr Leu Leu Arg Ile Ser Thr Gly Ile Glu Asp
        355                 360                 365

Gly Glu Asp Leu Ile Ala Asp Leu Glu Asn Gly Phe Arg Ala Ala Asn
    370                 375                 380

Lys Gly
385
```

```
<210> SEQ ID NO 32
<211> LENGTH: 388
<212> TYPE: PRT
<213> ORGANISM: Colwellia psychrerythraea
<220> FEATURE:
<221> NAME/KEY: misc_feature
<222> LOCATION: 1..388
<223> OTHER INFORMATION: Colwellia psychrerythraea 34H (strain)
<220> FEATURE:
<223> OTHER INFORMATION: metB

<400> SEQUENCE: 32
```

Met Ser Ile Thr Lys Lys Gly Asn Ile Thr Thr Ser Ala Val Arg Ala
1               5                   10                  15

Gly Ile Asn Thr Asp Gln Gln His Gly Ala Val Val Ala Pro Ile Tyr
            20                  25                  30

Leu Ser Ser Thr Tyr Ser Leu Lys Gly Phe Asn Asn Lys Arg Gln Phe
        35                  40                  45

Asp Tyr Ser Arg Thr Gly Asn Pro Thr Arg Ala Thr Phe Ala Gly Ala
    50                  55                  60

Ile Ala Glu Leu Glu Gln Gly Ser Val Gly Ile Val Thr Ser Thr Gly
65                  70                  75                  80

Met Ala Ala Val His Leu Ile Cys Gln Leu Leu Ser Thr Gln Asp Thr
                85                  90                  95

Val Val Ile Pro His Asp Cys Tyr Gly Gly Ser Phe Arg Leu Phe Thr
            100                 105                 110

His Leu Ala Lys Arg Gly Gln Phe Lys Leu Ile Val Val Asp Gln Asn
        115                 120                 125

Asp Gln Gln Ala Leu Asp Asn Ala Leu Ala His Lys Pro Lys Leu Val
    130                 135                 140

Leu Leu Glu Ser Pro Ser Asn Pro Leu Leu Arg Leu Val Asp Ile Glu
145                 150                 155                 160

Val Val Thr Lys Ala Cys His Ala Val Gly Ala Leu Val Ala Val Asp
                165                 170                 175

Asn Thr Phe Leu Ser Pro Ala Leu Gln Gln Pro Leu Thr Leu Gly Ala
            180                 185                 190

Asp Ile Val Phe His Ser Thr Thr Lys Tyr Ile Asn Gly His Ser Asp
        195                 200                 205

Val Val Gly Gly Val Val Ala Lys Thr Glu Glu Leu Gly Glu Gln
    210                 215                 220

Leu Ala Trp Trp Ala Asn Cys Ile Gly Ile Thr Gly Ser Ala Phe Asp
225                 230                 235                 240

Ser Phe Leu Ala Leu Arg Gly Leu Lys Thr Leu Pro Val Arg Met Lys
                245                 250                 255

Gln His Gln Glu Asn Ala Leu Arg Val Ala Asp Phe Leu Lys Asn His
            260                 265                 270

Asp Ala Ile Asp Ala Ile Tyr Phe Pro Gly Phe Pro Glu His Thr Gly
        275                 280                 285

His His Ile Ala Lys Lys Gln Gln Tyr Gly Phe Gly Ala Met Leu Ser
    290                 295                 300

Phe Glu Ile Lys Gly Asp Val Glu Ala Val Lys Lys Leu Phe Glu Asn
305                 310                 315                 320

Leu Glu Leu Phe Thr Leu Ala Gln Ser Leu Gly Gly Val Glu Ser Leu
                325                 330                 335

Ile Ser His Pro Ser Thr Met Thr His Ala Gly Met Thr Ile Pro Asp
            340                 345                 350

```
Gln Leu Glu Ala Gly Ile Thr Gln Ser Leu Val Arg Ile Ser Val Gly
            355                 360                 365

Ile Glu Asp Ile Asp Asp Ile Leu Ala Asp Leu Ala His Gly Leu Thr
    370                 375                 380

Gln Ser Gln Leu
385

<210> SEQ ID NO 33
<211> LENGTH: 386
<212> TYPE: PRT
<213> ORGANISM: Salmonella enterica
<220> FEATURE:
<221> NAME/KEY: misc_feature
<222> LOCATION: 1..386
<223> OTHER INFORMATION: Salmonella enterica subsp. enterica serovar
      Paratyphi A str. ATCC 9150 (strain)
<220> FEATURE:
<223> OTHER INFORMATION: metB

<400> SEQUENCE: 33

Met Thr Arg Lys Gln Ala Thr Ile Ala Val Arg Ser Gly Leu Asn Asp
1               5                   10                  15

Asp Glu Gln Tyr Gly Cys Val Val Pro Pro Ile His Leu Ser Ser Thr
            20                  25                  30

Tyr Asn Phe Thr Gly Phe Asn Glu Pro Arg Ala His Asp Tyr Ser Arg
        35                  40                  45

Arg Gly Asn Pro Thr Arg Asp Val Val Gln Arg Ala Leu Ala Glu Leu
    50                  55                  60

Glu Gly Gly Ala Gly Ala Val Leu Thr Asn Thr Gly Met Ser Ala Ile
65                  70                  75                  80

His Leu Val Thr Thr Val Phe Leu Lys Pro Gly Asp Leu Leu Val Ala
                85                  90                  95

Pro His Asp Cys Tyr Gly Gly Ser Tyr Arg Leu Phe Asp Ser Leu Ala
            100                 105                 110

Thr Arg Gly Cys Tyr Cys Val Arg Phe Val Asp Gln Gly Asp Glu Arg
        115                 120                 125

Ala Leu Gln Ala Ala Leu Glu Glu Lys Pro Lys Leu Val Leu Val Glu
    130                 135                 140

Ser Pro Ser Asn Pro Leu Leu Arg Val Val Asp Ile Ala Lys Ile Cys
145                 150                 155                 160

Arg Leu Ala Arg Glu Ala Gly Ala Val Ser Val Val Asp Asn Thr Phe
                165                 170                 175

Leu Ser Pro Ala Leu Gln Asn Pro Leu Ala Leu Gly Ala Asp Leu Val
            180                 185                 190

Leu His Ser Cys Thr Lys Tyr Leu Asn Gly His Ser Asp Val Val Ala
        195                 200                 205

Gly Val Val Ile Ala Lys Asp Pro Glu Val Val Thr Glu Leu Ala Trp
    210                 215                 220

Trp Ala Asn Asn Ile Gly Val Thr Gly Gly Ala Phe Asp Ser Tyr Leu
225                 230                 235                 240

Leu Leu Arg Gly Leu Arg Thr Leu Val Pro Arg Met Glu Leu Ala Gln
                245                 250                 255

Arg Asn Ala Gln Ala Ile Val Lys Tyr Leu Gln Thr Gln Pro Leu Val
            260                 265                 270

Lys Lys Leu Tyr His Pro Ser Leu Pro Glu Asn Gln Gly His Glu Ile
        275                 280                 285

Ala Ala Arg Gln Gln Lys Gly Phe Gly Ala Met Leu Ser Phe Glu Leu
```

```
            290             295             300
Asp Gly Asp Glu Glu Thr Leu Arg Arg Phe Leu Gly Gly Leu Ser Leu
305             310             315             320

Phe Thr Leu Ala Glu Ser Leu Gly Gly Val Glu Ser Leu Ile Ser His
            325             330             335

Ala Ala Thr Met Thr His Ala Gly Met Ser Pro Gln Ala Arg Ala Ala
            340             345             350

Ala Gly Ile Ser Glu Thr Leu Leu Arg Ile Ser Thr Gly Ile Glu Asp
            355             360             365

Gly Glu Asp Leu Ile Ala Asp Leu Gly Asn Gly Phe Arg Ala Ala Asn
            370             375             380

Lys Gly
385

<210> SEQ ID NO 34
<211> LENGTH: 393
<212> TYPE: PRT
<213> ORGANISM: Rhodobacter sphaeroides
<220> FEATURE:
<221> NAME/KEY: misc_feature
<222> LOCATION: 1..393
<223> OTHER INFORMATION: Rhodobacter sphaeroides ATCC 17029 (strain)
<220> FEATURE:
<223> OTHER INFORMATION: metZ

<400> SEQUENCE: 34

Met Thr Lys Asp Trp Lys Thr Arg Thr Gln Leu Val His Gly Gly Ser
1               5               10              15

Arg Arg Ser Gln Tyr Gly Glu Met Ala Glu Ala Ile Phe Leu Thr Gln
            20              25              30

Gly Phe Val Tyr Asp Ser Ala Glu Gln Ala Glu Ala Arg Phe Ile Glu
            35              40              45

Thr Gly Ala Asp Glu Phe Ile Tyr Ala Arg Tyr Gly Asn Pro Thr Thr
50              55              60

Arg Met Phe Glu Glu Arg Ile Ala Ala Val Glu Gly Thr Glu Asp Ala
65              70              75              80

Phe Ala Thr Ala Ser Gly Met Ala Ala Ile His Gly Val Leu Thr Ser
            85              90              95

Ile Val Arg Ala Gly Asp His Leu Val Ala Ala Arg Ala Leu Phe Gly
            100             105             110

Ser Cys Ile Tyr Ile Leu Glu Glu Val Leu Gly Arg Phe Gly Val Glu
            115             120             125

Val Thr Phe Val Asp Gly Thr Asp Leu Asp Gln Trp Arg Ala Ala Val
130             135             140

Arg Pro Gly Thr Lys Ala Val Phe Phe Glu Ser Val Ser Asn Pro Thr
145             150             155             160

Leu Glu Val Ala Asp Ile Gly Ala Ile Ala Glu Ile Ala His Ala Val
            165             170             175

Gly Ala Leu Val Ile Val Asp Asn Val Phe Ala Thr Pro Val Phe Ser
            180             185             190

Thr Ala Val Arg Gln Gly Ala Asp Val Val Ile Tyr Ser Ala Thr Lys
            195             200             205

His Ile Asp Gly Gln Gly Arg Ala Leu Gly Gly Val Val Cys Ala Ser
            210             215             220

Gln Ala Phe Ile Arg Lys Val Leu Glu Pro Phe Met Lys His Thr Gly
225             230             235             240
```

```
Gly Ser Met Ser Pro Phe Asn Ala Trp Leu Met Leu Asn Gly Met Ala
            245             250             255
Thr Leu Asp Leu Arg Cys Arg Ala Met Ala Asp Thr Ala Glu Lys Ile
            260             265             270
Ala Arg Ala Leu Glu Gly His Pro Gln Leu Gly Arg Val Ile His Pro
            275             280             285
Ala Leu Glu Ser His Pro Gln His Asp Met Ala Lys Ala Gln Met Glu
        290             295             300
Arg Pro Gly Thr Met Ile Ala Leu Asp Leu Ala Gly Gly Lys Glu Ala
305             310             315             320
Ala Phe Arg Phe Leu Asp Ala Leu Lys Ile Val Lys Ile Ser Asn Asn
            325             330             335
Leu Gly Asp Ala Arg Ser Ile Ala Thr His Pro Ala Thr Thr Thr His
            340             345             350
Gln Arg Leu Ser Asp Ala Gln Lys Ala His Leu Gly Ile Thr Pro Gly
            355             360             365
Leu Val Arg Leu Ser Val Gly Leu Glu Asp Ala Asp Asp Leu Ile Ala
        370             375             380
Asp Leu Lys Gln Ala Leu Ala Val Ile
385             390
```

ENZYMATIC METHOD FOR PRODUCING L-GLUFOSINATE AND ITS PHOSPHOESTERS

CROSS-REFERENCE TO RELATED APPLICATIONS

This application is a National Stage entry under § 371 of International Application No. PCT/EP2022/058082, filed on Mar. 28, 2022, and which claims the benefit of priority to European Patent Application No. 21166546.8, filed on Apr. 1, 2021. The content of each of these applications is hereby incorporated by reference in its entirety.

REFERENCE TO A SEQUENCE LISTING

The present application is accompanied by an ASCII text file as a computer readable form containing the sequence listing entitled, "Seq-List-005787USPCT-as-filed.txt", created on Sep. 26, 2023, with a file size of 139,400 bytes, the content of which is hereby incorporated by reference in its entirety.

BACKGROUND OF THE INVENTION

Field of the Invention

The present invention relates to an enzymatically catalyzed method for producing L-glufosinate ("L-GA" or "LGA") or a phosphoester thereof. The method comprises a step in which an activated L-homoserine $H_A$ is reacted with a substrate S selected from methylphosphinic acid and the esters of methylphosphinic acid. The invention makes accessible new substrates in the enzymatic production of L-glufosinate and its phosphoesters.

1. Description of Related Art

1. BACKGROUND OF THE INVENTION

Organic phosphor compounds, i.e. chemical agents comprising a carbon-phosphor bond, are widely applied as herbicides in the area of plant protection. Agents such as the herbicides glyphosate (Roundup®, Touchdown) and glufosinate (Basta®, Liberty®) as well as the growth regulator glyphosine (Polaris®) are used for this purpose (as described for example by G. Horlein, Rev. Environ. Contam. Toxicol. 1994, 138, 73-145).

The esters of P-methyl phosphinic acid (for example, P-methyl phosphinic acid butyl ester; "MPBE"; CAS-No: 6172-80-1) have a key role as synthetic building blocks in the synthesis of the non-selective herbicide glufosinate. These esters are accessible via two fundamental synthetic pathways (summarized in FIGS. 3 a and 3 b, p. 130, of the article of K. Haack, Chem. Unserer Zeit 2003, 37, 128-138):

a. Reacting diethyl chlorophosphite $[ClP(OC_2H_5)_2]$ with $CH_3MgCl$ provides methyl diethoxy phosphine $[H_3CP(OC_2H_5)_2$; "DEMP"; CAS-No. 15715-41-0], which is partially hydrolyzed to give the corresponding methylphosphinic acid ethyl ester (MPEE; CAS-Nr-16391-074).
b. Alternatively, methane can be reacted with phosphor trichloride at 500° C. to give methyl dichloro phosphane $H_3CPCl_2$. The latter can then be solvolyzed in alcohols to give the corresponding methyl phosphinic acid esters.

The esters of P-methyl phosphinic acid add to carbon-carbon double bonds regioselectively. This property is used in the synthesis of glufosinate for the formation of the second phosphor-carbon bond. For example, $H_3CPH(O)OR$ (R=Alkyl) reacts with 1-cyano allyl acetate in an addition reaction to provide an intermediate. Subsequent exchange of the acetate substitent with ammonia and hydrolysis of the cyano group and the ester group of the phosphinic acid moiety give glufosinate.

Acrylic acid ester is a cheaper alternative starting material. It can react with the ester of P-methyl phosphinic acid to 3-[alkoxy(methyo)phosphinyl]propionic acid alkyl ester. Claisen reaction of this diesterwith diethy oxalate, hydrolysis and decarboxylation provide the corresponding α-keto acid, which can be reductively aminated to give glufosinate.

These and further synthetic mutes towards L-glufosinate are also described in the art, e.g. in WO 1999/009039 A1, EP 0 508 296 A1.

WO 2020/145513 A1 and WO 2020/145514 A1 describe a chemical route to L-glufosinate. In this route, a homoserine derivative such as 0-acetyl homoserine or O-succinyl homoserine is used as starting material and L-glufosinate is obtained by a sequence of reactions including lactonization and halogenation.

WO 2020/145627 A1 describes a similar route, wherein, during halogenation, a bromine derivative is obtained.

The route disclosed by CN 106083922 A is similar but starts off from L-methionine.

EP 2402453 A2 describes an enzymatic method for producing methionine by enzymatically reacting a mixture of methyl mercaptan and dimethyl sulfide with 0-acetyl homoserine or O-succinyl homoserine.

CN 108516991 A describes another synthetic pathway to L-glufosinate, starting with the azeotropic dehydration of L-homoserine to give L-3,6-bis(2-haloethyl)-2,5-diketopiperazine, followed by the introduction of a methylphosphinate diester group and hydrolysis.

A general disadvantage of all synthetic routes to glufosinate is that the obtained glufosinate is a racemic mixture. However, as there is no herbicidal activity of the D-enantiomer, L-glufosinate is the enantiomer of economical interest.

For the enantioselective syntheses of L-glufosinate, enzymatic pathways are described in the art.

WO 2017/151573 A1 discloses a two-step enzymatic synthesis of L-glufosinate from D-glufosinate.

In the first step, D-glufosinate is oxidatively deaminated to give 2-oxo-4-[hydroxy(methy)phosphinoyl]butyric acid ("PPO"), followed by the specific amination of PPO to L-glufosinate as the second step. The first step is carried out by the catalysis of a D-amino acid oxidase, the second step is catalyzed by a transaminase.

WO 2020/051188 A1 discloses a similar method of converting racemic glufosinate to the L-glufosinate enantiomer. In addition, it discloses a step in which the α-ketoacid or ketone byproduct formed during amination of PPO with an amine donor is converted by ketoglutarate decarboxylase to further shift the equilibrium to L-glufosinate.

WO 2019/018406 A1 discloses a method of purifying L-glufosinate from a mixture comprising L-glufosinate and glutamate. Glutamate is converted to pyroglutamate enzymatically by glutaminyl-peptidyl cyclotransferase, and L-glufosinate is then purified from the resulting mixture by ion-exchange.

The object of the present invention is to provide a further enzymatic process for producing L-gulfosinate in high enantiomeric excess. In particular, such process should allow to use new substrates which heretofore were not used in the enzymatic synthesis of L-glufosinate.

2. SUMMARY OF THE INVENTION

The present invention solves the problems mentioned above by providing a method for producing L-glufosinate from a substrate that has not been used in the enzymatic production of L-glufosinate before. In particular, the present invention provides a method for producing L-glufosinate or a phosphoester of L-glufosinate from methylphosphinic acid and its esters using an enzymatically catalyzed pathway. These phosphor compounds thus serve as alternative substrates in the production of L-glufosinate, allowing for flexibility of production where there is no reliance on the known substrates that are currently being used for L-glufosinate production.

In particular, this object is achieved by the present invention which relates to an enzymatically catalyzed method for producing L-glufosinate or a phosphoester thereof, comprising a step (a) in which an activated L-homoserine $H_A$ is reacted with a substrate S to produce these compounds.

3. BRIEF DESCRIPTION OF THE DRAWINGS

Figure 2:
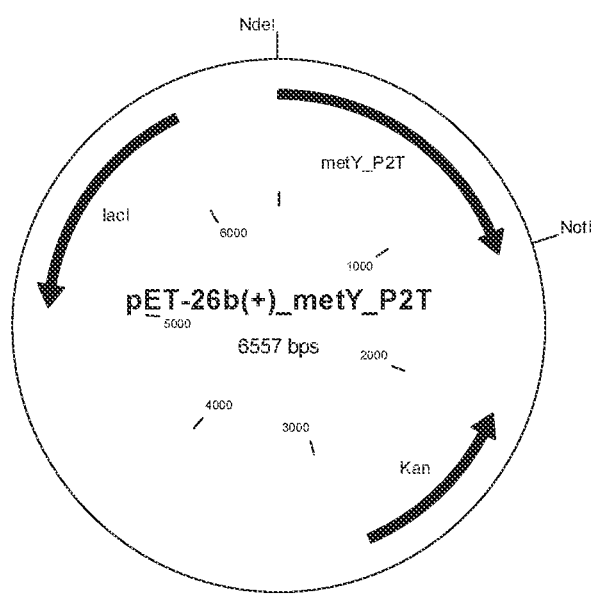
Figure 3:
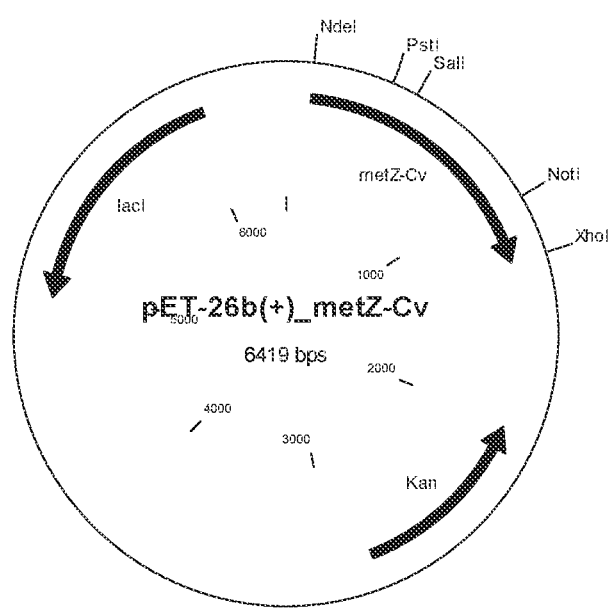
Figure 4:
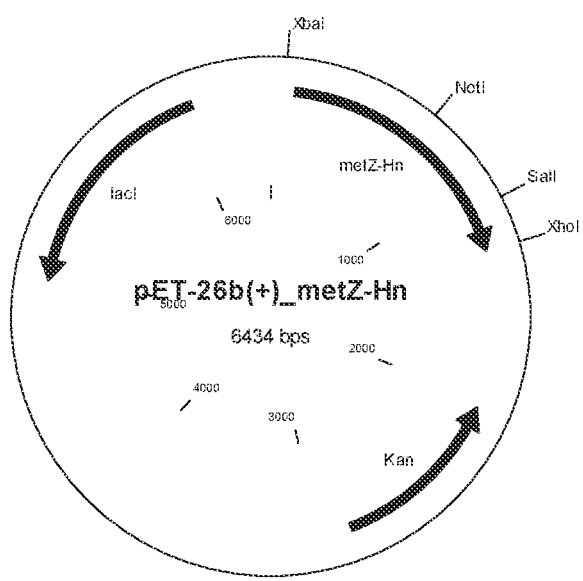

FIG. 1 shows the pET-26b(+)_metY-Cg plasmid map.
FIG. 2 shows the pET-26b(+)_metY_P2T plasmid map.
FIG. 3 shows the pET-26b(+)_metZ-Cv plasmid map.
FIG. 4 shows the pET-26b(+)_metZ-Hn plasmid map.

4. DETAILED DESCRIPTION OF THE INVENTION

It was surprisingly found that certain phosphor-containing compounds, namely methylphosphinic acid and esters of methylphosphinic acid, can react under enzymatic catalysis with activated L-homoserine, thus opening a new synthetic pathway to L-glufosinate and L-glufosinate posphoesters. This was especially surprising because similar compounds such as DEMP did not react in the analogous reaction with activated L-homoserine.

The present invention thus relates to an enzymatically catalyzed method for producing L-glufosinate or a phosphoester thereof, comprising a step (a) in which an activated L-homoserine $H_A$ is reacted with a substrate S of the following structure (I) to produce a compound of the following structure (III),

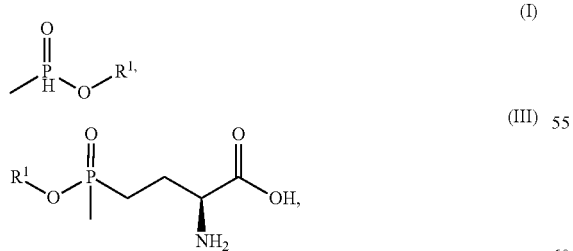

wherein $R^1$ is selected from hydrogen, alkyl, alkenyl, alkinyl, hydroxyalkyl, aryl.

The compounds denoted as "L-glufosinate or a phosphoester thereof" according to the invention are represented by structure (III). When $R^1$=hydrogen in structure (III), the compound is L-GA.

When $R^1$ is selected from alkyl, alkenyl, alkinyl, hydroxyalkyl, aryl in structure (III), the compound is a phosphoester of L-GA.

The activated L-homoserine $H_A$ has the following structure (II):

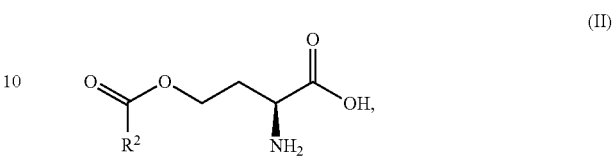

wherein $R^2$ is a hydrocarbon group with 1 to 15 carbon atoms which optionally comprises at least one functional group selected from OH, COOH, NH.

The reaction in step (a) is catalyzed by at least one enzyme selected from the group consisting of a sulfhydrylase $E_1$, a cystathionine γ-synthase $E_2$.

4.1 Substrate S

The substrate S according to the invention is selected from the group consisting of methylphosphinic acid and the esters of methylphosphinic acid.

The substrate S has the structure (I). In structure (I), $R^1$ is selected from hydrogen, alkyl, alkenyl, alkinyl, hydroxyalkyl, aryl,
preferably selected from hydrogen, alkyl,
preferably selected from hydrogen, alkyl with 1 to 6, preferably 1 to 4 carbon atoms,
more preferably selected from hydrogen, methyl, ethyl, iso-propyl, n-propyl, n-butyl, seoc-butyl, iso-butyl, ter-butyl, even more preferably selected from hydrogen, methyl, ethyl, n-butyl, even more preferably selected from hydrogen, methyl, n-butyl, preferably selected methyl, n-butyl. Most preferably, $R^1$ is n-butyl.

When $R^1$=hydrogen in structure (I), the compound is methylphosphinic acid.

When $R^1$ is selected from alkyl, alkenyl, alkinyl, hydroxyalkyl, aryl in structure (I), the compound is an ester of methylphosphinic acid.

$R^1$ in structure (I) and structure (III) is the same.

4.2 Activated L-Homoserine $H_A$

The other reaction partner in the reaction according to the present invention is activated L-homoserine $H_A$.

The skilled person is aware of activated L-homoserine $H_A$ (sometimes also denoted as "L-methionine precursor", e.g. in WO 2008/013432 A1), which in particular means O-acyl L-homoserine.

4.2.1 Activated L-Homoserine $H_A$

The activated L-homoserine has a chemical structure (II) as follows:

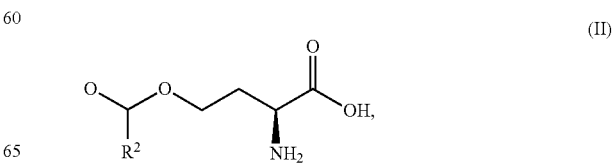

wherein $R^2$ is a hydrocarbon group with 1 to 15 carbon atoms which optionally comprises at least one functional group selected from OH, COOH, NH.

More preferably, the activated L-homoserine is selected from the group consisting of O-acetyl-L-homoserine [structure (II-A)], O-succinyl-L-homoserine [structure (II-B)], O-propionyl-L-homoserine [structure (II-C)], O-acetoacetyl-L-homoserine [structure (II-D)], O-coumaroyl-L-homoserine [structure (II-E)], O-malonyl-L-homoserine [structure (II-F)], O-hydroxymethylglutaryl-L-homoserine [structure (II-G)], and O-pimelyl-L-homoserine [structure (II-H)].

Even more preferably, the activated L-homoserines is selected from the group consisting of O-acetyl-L-homoserine [structure (II-A)], O-succinyl-L-homoserine [structure (II-B)].

Most preferably, the activated L-homoserine is O-acetyl-L-homoserine [structure (II-A)].

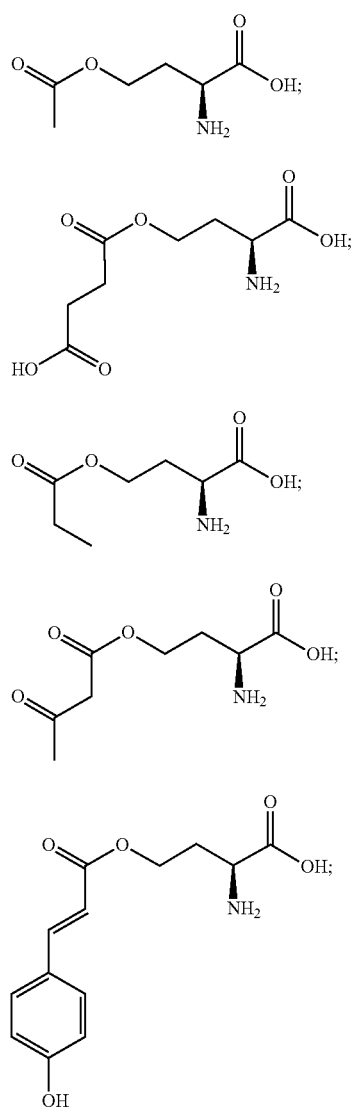

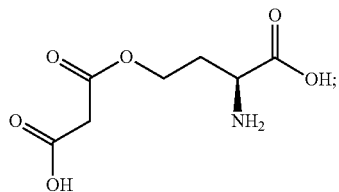

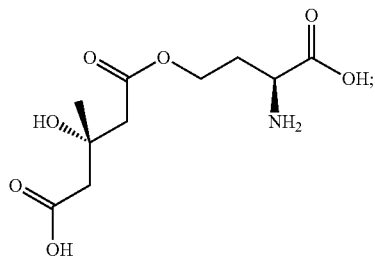

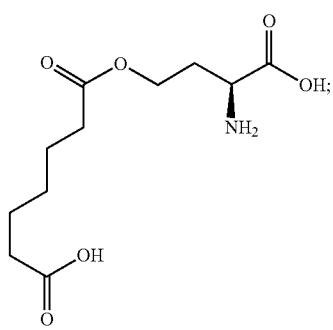

4.2.2 Chemical Synthesis of Activated L-Homoserine $H_A$

The activated L-homoserine $H_A$ used in the method of the present invention can be obtained by organochemical synthesis mutes known to the skilled person. For example, the synthesis of O-succinyl homoserine is described in M. Flavin, C. Slaughter, Biochemistry 1965, 4, 1370-1375. The synthesis of O-acetyl-homoserine is described by S. Nagai, M. Flavin, Methods in Enzymology, Metabolism of Amino Acids and Amines Part B 1971, 17(Part B), 423-424.

The chemical synthesis of the potential precursor is described for example by M. D. Armstrong, J. Am. Chem. Soc. 1948, 70, 1756-1759.

4.2.3 Biotechnological Synthesis of Activated L-Homoserine $H_A$

Alternatively, and preferably, the activated L-homoserine $H_A$ used in the present invention is obtained by biotechnological means. For example, this is described in WO 2008/013432 A1 or by H. Kase, K. Nakayama, Agr. Biol. Chem. 1974, 38, 2021-2030.

The strain producing activated L-homoserine $H_A$ is preferably selected from the group consisting of *Escherichia* sp., *Erwinia* sp., *Serratia* sp., *Providencia* sp., *Corynebacterum* sp., *Pseudomonas* sp., *Leptospira* sp., *Salmonella* sp., *Brevibacterium* sp., *Hypomononas* sp., *Chromobacterium* sp., *Norcardia* sp., fungi, which are in particular yeasts.

Biotechnological processes for obtaining L-homoserine are also described in the art, e.g. in U.S. Pat. Nos. 3,598,701, 6,303,348 B1, EP 0 994 190 A2, EP 1 149 911 A2, WO 2004/067757 A1.

4.3 Enzyme

The method according to the present invention is enzymatically catalyzed.

The term "enzyme" means any substance composed wholly or largely of protein or polypeptides that catalyzes or promotes, more or less specifically, one or more chemical or biochemical reactions.

Any of the enzymes used according to any aspect of the present invention may be an isolated enzyme. In particular, the enzymes used according to any aspect of the present invention may be used in an active state and in the presence of all cofactors, substrates, auxiliary and/or activating polypeptides or factors essential for its activity.

In particular, this also means that the terms "cystathionine γ-synthase" and "sulfhydrylase", in particular "O-acetyl homoserine sulfhydrylase" or "O-succinyl homoserine sulfhydrylase" comprise the respective enzymes in combination with all the cofactors necessary for their function. In particular, this cofactor is pyridoxal 5-phosphate mono-hydrate ("PMP").

A "polypeptide" is a chain of chemical building blocks called amino acids that are linked together by chemical bonds called peptide bonds. A protein or polypeptide, including an enzyme, may be "native" or "wild-type", meaning that it occurs in nature or has the amino acid sequence of a native protein, respectively. These terms are sometimes used interchangeably. A polypeptide may or may not be glycosylated.

The enzyme used according to any aspect of the present invention may be recombinant. The term "recombinant" as used herein, refers to a molecule or is encoded by such a molecule, particularly a polypeptide or nucleic acid that, as such, does not occur naturally but is the result of genetic engineering or refers to a cell that comprises a recombinant molecule. For example, a nucleic acid molecule is recombinant if it comprises a promoter functionally linked to a sequence encoding a catalytically active polypeptide and the promoter has been engineered such that the catalytically active polypeptide is overexpressed relative to the level of the polypeptide in the corresponding wild type cell that comprises the original unaltered nucleic acid molecule. As a further example, a polypeptide is recombinant if it is identical to a polypeptide sequence occurring in nature but has been engineered to contain one or more point mutations that distinguish it from any polypeptide sequence occurring in nature.

The term "overexpressed", as used herein, means that the respective polypeptide encoded or expressed is expressed at a level higher or at higher activity than would normally be found in the cell under identical conditions in the absence of genetic modifications carried out to increase the expression, for example in the respective wild type cell.

The term "isolated", as used herein, means that the enzyme of interest is enriched compared to the cell in which it occurs naturally. The enzyme may be enriched by SDS polyacrylamide electrophoresis and/or activity assays. For example, the enzyme of interest may constitute more than 5, 10, 20, 50, 75, 80, 85, 90, 95 or 99 percent of all the polypeptides present in the preparation as judged by visual inspection of a polyacrylamide gel following staining with Coomassie blue dye.

4.3.1 Enzymes $E_1$ and $E_2$

Step (a) of the method according to the invention is catalysed by at least one enzyme selected from the group consisting of a sulfhydrylase $E_1$ and a cystathionine γ-synthase $E_2$.

A sulfhydrylase is known to the skilled person as an enzyme that catalyzes at least one of the following reactions <1A>, <1B>:

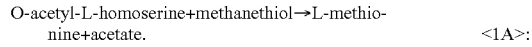

O-acetyl-L-homoserine+methanethiol→L-methionine+acetate.           <1A>:

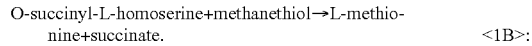

O-succinyl-L-homoserine+methanethiol→L-methionine+succinate.           <1B>:

A sulfhydrylase that has a higher catalytic activity for reaction <1A> than reaction <1B> may be denoted as an "O-acetyl-L-homoserine sulfhydrylase".

A sulfhydrylase that has a higher catalytic activity for reaction <1B> than reaction <1A> may be denoted as an "O-succinyl-L-homoserine sulfhydrylase".

A cystathionine γ-synthase is known to the skilled person as an enzyme that catalyzes at least the following reaction <2>:

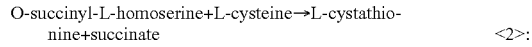

O-succinyl-L-homoserine+L-cysteine→L-cystathionine+succinate           <2>:

In a preferred embodiment, step (a) of the method according to the invention is catalysed by a sulfhydrylase $E_1$, which is even more preferably an O-acetyl homoserine sulfhydrylase or an O-succinyl homoserine sulfhydrylase, most preferably an O-acetyl homoserine sulfhydrylase.

The sulfhydrylase or the cystathionine γ-synthase that may be used in step (a) of the method according to the invention may be derived from *Bacillus* sp., in particular *Bacillus subtilis*; *Bradyrhizobium* sp., in particular *Bradyrhizobium japonicum*; *Brevibacterium* sp.; *Colwellia* sp., in particular *Colwellia psycherythraea*; *Corynebacterium* sp., in particular *Corynebacterium glutamicum*, *Corynebacterium humireducens*; *Chromobacterium* sp., in particular *Chromobacterium violaceum*; *Erwinia* sp.; *Escherichia* sp., in particular *Escherichia coli*; *Hyphomonas* sp., in particular *Hyphomonas neptunium*; *Klebsiella* sp., in particular *Klebsiella pneumoniae*; *Leptospira* sp., in particular *Leptospira interrogans*; *Methylobacillus* sp., in particular *Methylobacillus flagellates*; *Methylococcus* sp., in particular *Methylococcus capsulatus*; *Nitrosomonas* sp., in particular *Nitrosomonas europaea*; *Nocardia* sp., in particular *Nocardia farcinica*; *Providencia* sp.; *Pseudomonas* sp., in particular *Pseudomonas aeruginosa*; *Rhodobacter* sp., in particular *Rhodobacter sphaeroides*; *Salmonella* sp., in particular *Salmonella enterica*; *Serratia* sp.; *Shigella* sp., in particular *Shigella flexneri*; fungi, which are preferably yeast, more preferably *Saccharomyces* sp., even more preferably *Saccharomyces cerevisiae*.

The sulfhydrylase enzyme that may be used in the method according to the present invention may be an O-acetyl-L-homoserine sulfhydrylase categorized in the EC class EC 2.5.1.49 or an O-succinyl-L-homoserine sulfhydrylase categorized in the EC class EC 2.5.1.-.

These enzymes are part of the direct sulfurylation pathway for methionine biosynthesis and PMP-dependent. They are described e.g. by M. P. Feria and W. M. Patrick, Microbiology 2014, 160, 1571-1584.

WO 02/18613 A1, WO 2007/024933 A2, EP 2 657 345 A1, EP 2 657 250 A2, WO 2015/165746 A1 and WO 2008/013432 A1 disclose examples of enzymes having O-acetyl-L-homoserine sulfhydrylase and O-succinyl-L-homoserine sulfhydrylase activity according to the invention.

An O-acetyl-L-homoserine sulfhydrylase suitable for the method according to the present invention may originate from *Corynebacterium* sp., in particular *Corynebacterium glutamicum* or *Corynebacterium humireducens*; *Leptospira* sp., in particular *Leptospira interrogans*; *Pseudomonas* sp., in particular *Pseudomonas aeruginosa*; yeast, in particular *Saccharomyces* sp., preferably *Saccharomyces cerevisiae*. A preferable O-acetyl-L-homoserine sulfhydrylase suitable for the method according to the present invention may originate from *Corynebacterium* sp., more preferably *Corynebacterium glutamicum* or *Corynebacterium humireducens*, even more preferably *Corynebacterium glutamicum*, even more preferably *Corynebacterium glutamicum* ATCC 13032.

An O-succinyl-L-homoserine sulfhydrylase suitable for the method according to the present invention may originate from *Bradyrhizobium* sp., in particular *Bradyrhizobium japonicum*; *Chromobacterium* sp., in particular *Chromobacterium violaceum*; *Hyphomonas* sp., in particular *Hyphomonas neptunium*; *Methylobacillus* sp., in particular *Methylobacillus flagellatus*; *Methylococcus* sp., in particular *Methylococcus capsulatus*; *Nitrosomas* sp., in particular *Nitrosomas europaea*; *Nocardia* sp., *Nocardia farcinica*;

The respective sequences can be derived from databases such as the Braunschweig Enzyme Database (BRENDA, Germany, available underwww.brenda-enzymes.org/index-.php), the National Center for Biotechnological Information (NCBI, available under https://www.ncbi.nlm.nih.gov/) or the Kyoto Encyclopedia of Genes and Genomes (KEGG, Japan, available under www.https://www.genome.jp/kegg/).

The following table 1 gives preferred examples for sulfhydrylases and cystathionine γ-synthases that may be used in step (a) of the method according to the invention. The genes encoding sulfhydrylase are indicated as "metY", "met17", and "Met17" for O-acetyl-L-homoserine sulfhydrylase ("AHS") and "metZ" for O-succinyl-L-homoserine sulfhydrylase ("SHS"). The gene encoding cystathionine γ-synthase ("CGS") is indicated as "metB" and "met".

TABLE 1

| Strain | Gene name | Gene ID/locus tag | NCBI accession | SEQ ID NO: of the polypeptide |
| --- | --- | --- | --- | --- |
| *Corynebacterium glutamicum* ATCC 13032 | metY | NCgl0625 | NC_003450 | SEQ ID NO: 2 |
| *Corynebacterium glutamicum* ATCC 13032 | metY_P2T | — | — | SEQ ID NO: 6 |
| *Chromobacterium violaceum* ATCC 12472 | metZ | CV_2725 | AE016825 | SEQ ID NO: 10 |
| *Hyphomonas neptunium* ATCC 15444 | metZ | HNE_2672 | CP000158 | SEQ ID NO: 14 |
| *Escherichia coli* K12 MG1655 | metB | b3939 | U00096 | SEQ ID NO: 17 |
| *Pseudomonas aeruginosa* PAO1 | metZ | 880476/PA3107 | AE004091 | SEQ ID NO: 18 |
| *Pseudomonas aeruginosa* PAO1 | metY | 881205/PA5025 | AE004091 | SEQ ID NO: 19 |
| *Pseudomonas putida* KT2440 | metZ | PP_RS10380 | NC_002947 | SEQ ID NO: 20 |
| *Corynebacterium glutamicum* ATCC 13032 | metB | NCgl2360/CGL_RS12110 | NC_003450 | SEQ ID NO: 21 |
| *Leptospira interrogans* serovar *Lai* str. 56601 | met17 | LA_2062 | AE010300 | SEQ ID NO: 22 |
| *Saccharomyces cerevisiae* S288C | Met17 | Met17 | NC_001144 | SEQ ID NO: 23 |
| *Nocardia farcinica* IFM 10152 | metZ | NFA_53590 | AP006618 | SEQ ID NO: 24 |
| *Bradyrhizobium japonicum* USDA 6 | metZ | BJ6T_RS05520 | NC_017249 | SEQ ID NO: 25 |
| *Methylococcus capsulatus* str. Bath | metZ | MCA2488 | AE017282 | SEQ ID NO: 26 |
| *Methylobacillus flagellatus* KT | "metZ" | MFLA_RS08660 | NC_007947 | SEQ ID NO: 27 |
| *Nitrosomonas europaea* ATCC 19718 | metZ | ALW85_RS03655 | NC_004757 | SEQ ID NO: 28 |
| *Klebsiella pneumoniae* subsp. *pneumoniae* MGH 78578 | metB | KPN_RS22820 | NC_009648 | SEQ ID NO: 29 |
| *Bacillus subtilis* subsp. *subtilis* str. 168 | metI | BSU_11870 | NC_000964 | SEQ ID NO: 30 |
| *Shigella flexneri* 2a 2457T ATCC 700930 | metB | S3730 | AE014073 | SEQ ID NO: 31 |
| *Colwellia psychrerythraea* 34H ATCC BAA-681 | metB | CPS_0455 | CP000083 | SEQ ID NO: 32 |
| *Salmonella enterica* serovar *Paratyphi* A ATCC 9150 | metB | SPA3943 | CP000026 | SEQ ID NO: 33 |
| *Rhodobacter sphaeroides* ATCC 17029 | metZ | RSPH17029_RS02535 | NC_009049 | SEQ ID NO: 34 |

*Pseudomonas* sp., in particular *Pseudomonas aeruginosa*, *Pseudomonas putida*; *Rhodobacter* sp., in particular *Rhodobacter sphaeroides*.

A preferable O-succinyl-L-homoserine sulfhydrylase suitable for the method according to the present invention may originate from *Chromobacterium* sp., in particular *Chromobacterium violaceum*; *Hyphomonas* sp., in particular *Hyphomonas neptunium*. Even more preferably, it may originate from *Chromobacterium violaceum* ATCC 12472, *Hyphomonas neptunium* ATCC 15444.

The cystathionine γ-synthase that may be used in the method according to the present invention may be a cystathionine γ-synthase categorized in the EC class EC 2.5.1.48.

These enzymes are PMP-dependent and are described e.g. by T. Clausen, R. Huber, L. Prade, M. C. Wahl and A. Messerschmidt, The EMBO Journal 1998, 17, 6827-8838.

A cystathionine γ-synthase suitable for the method according to the present invention may originate from *Escherichia coli*, in particular *Escherichia coli*; *Corynebacterium* sp., in particular *Corynebacterium glutamicum*; *Klebsiella* sp., in particular *Klebsiella pneumoniae*; *Bacillus* sp., in particular *Bacillus subtilis*; *Shigella* sp., in particular *Shigella flexneri*; *Colwellia* sp., in particular *Colwellia psychrerythraea*; *Salmonella* sp., in particular *Salmonella enterica*.

In a preferred embodiment of the method of the present invention, the reaction in step (a) is catalyzed by at least one enzyme selected from the group consisting of a sulfhydrylase $E_1$, a cystathionine γ-synthase $E_2$, wherein the polypeptide sequence of the sulfhydrylase enzyme $E_1$ is selected from the group consisting of:

O-acetyl homoserine sulfhydrylases selected from the group consisting of SEQ ID NO: 2 and variants of SEQ ID NO: 2, SEQ ID NO: 6 and variants of SEQ ID NO: 6, SEQ ID NO: 19 and variants of SEQ ID NO: 19, SEQ ID NO: 22 and variants of SEQ ID NO: 22, SEQ ID NO: 23 and variants of SEQ ID NO: 23, and O-succinyl homoserine sulfhydrylases selected from the group consisting of SEQ ID NO: 10 and variants of SEQ ID NO: 10, SEQ ID NO: 14 and variants of SEQ ID NO: 14, SEQ ID NO: 18 and variants of SEQ ID NO: 18, SEQ ID NO: 20 and variants of SEQ ID NO: 20, SEQ ID NO: 24 and variants of SEQ ID NO: 24, SEQ ID NO: 25 and variants of SEQ ID NO: 25, SEQ ID NO: 26 and variants of SEQ ID NO: 26, SEQ ID NO: 27 and variants of SEQ ID NO: 27, SEQ ID NO: 28 and variants of SEQ ID NO: 28, SEQ ID NO: 34 and variants of SEQ ID NO: 34, and wherein the polypeptide sequence of the cystathionine γ-synthase $E_2$ is selected from the group consisting of SEQ ID NO: 17 and variants thereof, SEQ ID NO: 21 and variants thereof, SEQ ID NO: 29 and variants thereof, SEQ ID NO: 30 and variants thereof, SEQ ID NO: 31 and variants thereof, SEQ ID NO: 32 and variants thereof, SEQ ID NO: 33 and variants thereof.

In a more preferred embodiment of the method of the present invention, the reaction in step (a) is catalyzed by a sulfhydrylase $E_1$ selected from the group consisting of O-acetyl homoserine sulfhydrylases selected from the group consisting of SEQ ID NO: 2 and variants of SEQ ID NO: 2, SEQ ID NO: 6 and variants of SEQ ID NO: 6, SEQ ID NO: 19 and variants of SEQ ID NO: 19, SEQ ID NO: 22 and variants of SEQ ID NO: 22, SEQ ID NO: 23 and variants of SEQ ID NO: 23, and O-succinyl homoserine sulfhydrylases selected from the group consisting of SEQ ID NO: 10 and variants of SEQ ID NO: 10, SEQ ID NO: 14 and variants of SEQ ID NO: 14, SEQ ID NO: 18 and variants of SEQ ID NO: 18, SEQ ID NO: 20 and variants of SEQ ID NO: 20, SEQ ID NO: 24 and variants of SEQ ID NO: 24, SEQ ID NO: 25 and variants of SEQ ID NO: 25, SEQ ID NO: 26 and variants of SEQ ID NO: 26, SEQ ID NO: 27 and variants of SEQ ID NO: 27, SEQ ID NO: 28 and variants of SEQ ID NO: 28, SEQ ID NO: 34 and variants of SEQ ID NO: 34.

In an even more preferred embodiment of the method of the present invention, the reaction in step (a) is catalyzed by a sulfhydrylase $E_1$ selected from the group consisting of O-acetyl homoserine sulfhydrylases selected from the group consisting of SEQ ID NO: 2 and variants of SEQ ID NO: 2, SEQ ID NO: 6 and variants of SEQ ID NO: 6 and O-succinyl homoserine sulfhydrylases selected from the group consisting of SEQ ID NO: 10 and variants of SEQ ID NO: 10, SEQ ID NO: 14 and variants of SEQ ID NO: 14.

In an even more preferred embodiment of the method of the present invention, the reaction in step (a) is catalyzed by a sulfhydrylase $E_1$ selected from the group consisting of O-acetyl homoserine sulfhydrylases selected from the group consisting of SEQ ID NO: 2, SEQ ID NO: 6, and O-succinyl homoserine sulfhydrylases selected from the group consisting of SEQ ID NO: 10, SEQ ID NO: 14.

The term "variant" is further explained below (item 4.3.3.1). In the context of the present application, it is understood to mean a polypeptide sequences with at least 80% sequence identity to the respective polypeptide sequence.

4.3.2 Methods for Obtaining Enzymes

The enzymes that can be used in the method according to the present invention can be synthesized by methods that are known to the skilled person.

One approach is to express the enzyme(s) in microorganism(s) such as *Escherichia coli* (="*E. coli*"), *Saccharomyces cerevisiae*, *Pichia pastoris*, and others, and to add the whole cells to the reactions as whole cell biocatalysts. Another approach is to express the enzyme(s), lyse the microorganisms, and add the cell lysate. Yet another approach is to purify, or partially purify, the enzyme(s) from a lysate and add pure or partially pure enzyme(s) to the reaction. If multiple enzymes are required for a reaction, the enzymes can be expressed in one or several microorganisms, including expressing all enzymes within a single microorganism.

For example, the skilled person can obtain the enzymes according to the invention by expression, in particular, overexpression, (hereinafter, "expression, in particular overexpression" is abbreviated as (over)expression", and "express, in particular overexpress" is abbreviated as "(over)express") of these enzymes in a cell and subsequent isolation thereof, e.g. as described in DE 100 31 999 A1. Episomal plasmids, for example, are employed for increasing the expression of the respective genes. In such plasmids, the nucleic acid molecule to be (over)expressed or encoding the polypeptide or enzyme to be (over)expressed may be placed under the control of a strong inducible promoter such as the lac promoter, located upstream of the gene. A promoter is a DNA sequence consisting of about 40 to 50 base pairs which constitutes the binding site for an RNA polymerase holoenzyme and the transcriptional start point (M. Pátek, J. Holátko, T. Busche, J. Kalinowski, J. Nešvera, Microbial Biotechnology 2013, 6, 103-117), whereby the strength of expression of the controlled polynucleotide or gene can be influenced. A "functional linkage" is obtained by the sequential arrangement of a promoter with a gene, which leads to a transcription of the gene.

Suitable strong promoters or methods of producing such promoters for increasing expression are known from the literature (e.g. S. Lisser & H. Margalit, Nucleic Acid Research 1993, 21, 1507-1516; M. Paték and J. Nesvera in H. Yukawa and M Inui (eds.), *Corynebacterium glutamicum*, Microbiology Monographs 23, Springer Verlag Berlin Heidelberg 2013, 51-88; B. J. Eikmanns, E. Kleinertz, W. Liebl, H. Sahm, Gene 1991, 102, 93-98). For instance, native promoters may be optimized by altering the promoter sequence in the direction of known consensus sequences with respect to increasing the expression of the genes functionally linked to these promoters (M. Pitek, B. J. Eikmanns, J. Pitek, H. Sahm, Microbiology 1996, 142, 1297-1309; M. Pitek, J. Holitko, T. Busche, J. Kalinowski, J. Nešvera, Microbial Biotechnology 2013, 6, 103-117).

Constitutive promoters are also suitable for the (over) expression, in which the gene encoding the enzyme activity is expressed continuously under the control of the promoter such as, for example, the glucose dependent deo promoter. Chemically induced promoters are also suitable, such as tac, lac or rp. The most widespread system for the induction of promoters is the lac operon of *E. coli*. In this case, either lactose or isopropyl ß-D-thiogalactopyranoside (IPTG) is used as inducer. Also, systems using arabinose (e.g. the pBAD system) or rhamnose (e.g. *E. coli* KRX) are common as inducers. A system for physical induction is, for example, the temperature-induced cold shock promoter system based on the *E. coli* cspA promoter from Takara or Lambda PL and also osmotically inducible promoters, for example, osmB (e.g. WO 95/25785 A1).

Suitable plasmids or vectors are in principle all embodiments available for this purpose to the person skilled in the art. The state of the art describes standard plasmids that may be used for this purpose, for example the pET system of vectors exemplified by pET-3a or pET-26b(+) (commercially available from Novagen). Further plasmids and vectors can be taken, for example, from the brochures of the companies Novagen, Promega, New England Biolabs, Clontech or Gibco BRL. Further preferred plasmids and vectors can be found in: Glover, D. M. (1985) DNA cloning: a practical approach, Vol. I-III, IRL Press Ltd., Oxford; Rodriguez, R. L. and Denhardt, D. T (eds) (1988) Vectors: a survey of molecular cloning vectors and their uses, 179-204, Butterworth, Stoneham; Goeddel, D. V. (1990) Systems for heterologous gene expression, Methods Enzymol. 185, 3-7; Sambrook, J.; Fritsch, E. F. and Maniatis, T. (1989), Molecular cloning: a laboratory manual, 2nd ed., Cold Spring Harbor Laboratory Press, New York.

The plasmid vector, which contains the gene to be amplified, is then converted to the desired strain, e.g. by conjugation or transformation. The method of conjugation is described, for example, by A. Schäfer, J. Kalinowski, A. Pühler, Applied and Environmental Microbiology 1994, 60, 756-759. Methods for transformation are described, for example, in G. Thierbach, A. Schwarzer, A. Pühler, Applied Microbiology and Biotechnology 1988, 29, 356-362, L. K. Dunican & E. Shivnan, Bio/Technology 1989, 7, 1067-1070 and A. Tauch, O. Kirchner, L. Wehmeier, J. Kalinowski, A. Pühler, FEMS Microbiology Letters 1994, 123, 343-347. After homologous recombination by means of a "crossover" event, the resulting strain contains at least two copies of the gene concerned.

The desired enzyme can be isolated by disrupting cells which contain the desired activity in a manner known to the person skilled in the art, for example with the aid of a ball mill, a French press or of an ultrasonic disintegrator and subsequently separating off cells, cell debris and disruption aids, such as, for example, glass beads, by centrifugation for 10 minutes at 13000 rpm and 4° C. Using the resulting cell-free crude extract, enzyme assays with subsequent LC-ESI-MS detection of the products can then be carried out. Alternatively, the enzyme can be enriched in the manner known to the person skilled in the art by chromatographic methods (such as nickel-nitrilotriacetic acid affinity chromatography, streptavidin affinity chromatography, gel filtration chromatography or ion-exchange chromatography) or else purified to homogeneity.

Whether or not a nucleic acid or polypeptide is (over) expressed, may be determined by way of quantitative PCR reaction in the case of a nucleic acid molecule, SDS polyacrylamide electrophoreses, Western blotting or comparative activity assays in the case of a polypeptide. Genetic modifications may be directed to transcriptional, translational, and/or post-translational modifications that result in a change of enzyme activity and/or selectivity under selected and/or identified culture conditions.

4.3.3 Definitions

4.3.3.1 "Variants"

In the context of the present invention, the term "variant" with respect to polypeptide sequences refers to a polypeptide sequence with a degree of identity to the reference sequence of at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%. In still further particular embodiments, the degree of identity is at least 98.0%, more preferably at least 98.2%, more preferably at least 98.4%, more preferably at least 98.6%, more preferably at least 98.8%, more preferably at least 99.0%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, or at least more preferably at least 99.9%. It goes without saying that a "variant" of a certain polypeptide sequence is not identical to the polypeptide sequence.

Such variants may be prepared by introducing deletions, insertions, substitutions, or combinations thereof, in particular in amino acid sequences, as well as fusions comprising such macromolecules or variants thereof.

Modifications of amino acid residues of a given polypeptide sequence which lead to no significant modifications of the properties and function of the given polypeptide are known to those skilled in the art. Thus for example many amino acids can often be exchanged for one another without problems; examples of such suitable amino acid substitutions are: Ala by Ser; Arg by Lys; Asn by Gln or His; Asp by Glu; Cys by Ser; Gln by Asn; Glu by Asp; Gly by Pro; His by Asn or Gln; lie by Leu or Val; Leu by Met or Val; Lys by Arg or Gln or Glu; Met by Leu or Ile; Phe by Met or Leu or Tyr; Ser by Thr; Thr by Ser; Trp by Tyr; Tyr by Trp or Phe; Val by Ile or Leu. It is also known that modifications, particularly at the N- or C-terminus of a polypeptide in the form of for example amino acid insertions or deletions, often exert no significant influence on the function of the polypeptide.

In line with this, preferable variants according to the invention of any of SEQ ID NO: 2, SEQ ID NO: 6, SEQ ID NO: 19, SEQ ID NO: 22, SEQ ID NO: 23, SEQ ID NO: 10, SEQ ID NO: 14, SEQ ID NO: 18, SEQ ID NO: 20, SEQ ID NO: 24, SEQ ID NO: 25, SEQ ID NO: 26, SEQ ID NO: 27, SEQ ID NO: 28, SEQ ID NO: 34, SEQ ID NO: 17, SEQ ID NO: 21, SEQ ID NO: 29, SEQ ID NO: 30, SEQ ID NO: 31, SEQ ID NO: 32, and SEQ ID NO: 33, respectively, have a polypeptide sequence that comprises the amino acids of the respective sequence that are essential for the function, for example the catalytic activity of a protein, or the fold or structure of the protein. The other amino acids may be deleted, substituted or replaced by insertions or essential amino acids are replaced in a conservative manner to the effect that the activity of the enzyme, in particular the sulfhydrylase or the cystathionine γ-synthase, is preserved.

4.3.3.2 "Sequence Identity"

The person skilled in the art is aware that various computer programs are available for the calculation of similarity or identity between two nucleotide or amino acid sequences.

Preferred methods for determining the identity initially generate the greatest alignment between the sequences to be compared. Computer programs for determining the identity include, but are not limited to, the GCG program package including GAP [J. Deveroy et al., Nucleic Acid Research 1984, 12, page 387, Genetics Computer Group University of Wisconsin, Medicine (WI)], and BLASTP, BLASTN and FASTA (S. Altschul et al., Journal of Molecular Biology 1990, 215, 403-410). The BLAST program can be obtained from the National Center for Biotechnology Information (NCBI) and from other sources (BLAST Handbook, S. Altschul et al., NCBI NLM NIH Bethesda ND 22894; S. Altschul et al., above).

For instance, the percentage identity between two amino acid sequences can be determined by the algorithm developed by S. B. Needleman and C. D. Wunsch, J. Mol. Biol. 1970, 48, 443-453, which has been integrated into the GAP program in the GCG software package, using either a BLOSUM62 matrix or a PAM250 matrix, a gap weight of 16, 14, 12, 10, 8, 6 or 4 and a length weight of 1, 2, 3, 4, 5 or 6. The person skilled in the art will recognize that the use of different parameters will lead to slightly different results, but that the percentage identity between two amino acid sequences overall will not be significantly different. The BLOSUM62 matrix is typically used applying the default settings (gap weight: 12, length weight: 1).

In the context of the present invention, a sequence identity of 80% according to the above algorithm means 80% homology. The same applies to higher identities.

Most preferably, the degree of identity between sequences is determined in the context of the present invention by the programme "Needle" using the substitution matrix BLOSUM62, the gap opening penalty of 10, and the gap extension penalty of 0.5. The Needle program implements the global alignment algorithm described in S. B. Needleman and C. D. Wunsch, J. Mol. Biol. 1970, 48, 443-453. The substitution matrix used according to the present invention is BLOSUM62, gap opening penalty is 10, and gap extension penalty is 0.5. The preferred version used in the context of this invention is the one presented by F. Madeira, Y. M. Park, J. Lee, N. Buso, T. Gur, N. Madhusoodanan, P. Basutkar, A. R. N. Tivey, S. C. Potter, R. D. Finn, Nucleic Acids Research 2019, 47, W836-W841, Web Server issue (preferred version accessible online on Mar. 31, 2021 via https://www.ebi.ac.uk/Tools/psa/emboss_needle/).

In a particular embodiment, the percentage of identity of an amino acid sequence of a polypeptide with, or to, a reference polypeptide sequence is determined by i) aligning the two amino acid sequences using the Needle program, with the BLOSUM62 substitution matrix, a gap opening penalty of 10, and a gap extension penalty of 0.5; ii) counting the number of exact matches in the alignment; iii) dividing the number of exact matches by the length of the longest of the two amino acid sequences, and iv) converting the result of the division of iii) into percentage.

4.3.3.3 "Preferred Assay to Identify Particularly Active Variants"

4.3.3.3.1 Assay A

Especially preferable polypeptide variants of any of SEQ ID NO: 2, SEQ ID NO: 6, SEQ ID NO: 19, SEQ ID NO: 22, SEQ ID NO: 23, SEQ ID NO: 10, SEQ ID NO: 14, SEQ ID NO: 18, SEQ ID NO: 20, SEQ ID NO: 24, SEQ ID NO: 25, SEQ ID NO: 26, SEQ ID NO: 27, SEQ ID NO: 28, SEQ ID NO: 34, SEQ ID NO: 17, SEQ ID NO: 21, SEQ ID NO: 29, SEQ ID NO: 30, SEQ ID NO: 31, SEQ ID NO: 32, and SEQ ID NO: 33, respectively, in the context of the present invention may be identified by the skilled person as those displaying activity in the following assay ("Assay A").

Assay A is carried out by the following steps:
A1) First, the activity of the variant to be tested is determined by the following steps A1.1), A1.2), and A1.3) as follows:
A1.1) 990 µl of a reaction solution containing phosphate buffer (0.1 M, pH 7.5), 3 mM O-acetyl L-homoserine-HCl, 10 µM pyridoxal 5-phosphate mono-hydrate and 1.0 nmol of the polypeptide to be tested are prepared and heated to 50° C.
A1.2) The reaction is started by adding 10 µl of a 200 mM solution of butyl-P-methylphosphinate (MPBE, CAS #6172-80-1). The concentration of MPBE in the reaction solution is 2 mM.
A1.3) After addition of the MPBE, the reaction is conducted for 120 minutes at 50° C. Then, the reaction is stopped by adding 10 µl 1% formate solution and cooling on ice.
A2) Then, a blank test is carried out by the following steps A2.1), A2.2), and A2.3) as follows: A2.1) 990 µl of a reaction solution containing phosphate buffer (0.1 M, pH 7.5), 3 mM O-acetyl L-homoserine-HCl, 10 µM pyridoxal 5-phosphate mono-hydrate are prepared and heated to 50° C.
A2.2) The reaction is started by adding 10 µl of a 200 mM solution of butyl-P-methylphosphinate (MPBE, CAS #6172-80-1).
A2.3) After addition of the MPBE, the reaction is conducted for 120 minutes at 50° C. Then, the reaction is stopped by adding 10 µl 1% formate solution and cooling on ice.
A3) Finally, the amount (in mole) of the butyl-phosphoester of L-GA (i.e. the compound according to formula (III) with $R^1$=n-butyl) obtained in the reaction solution in A1.3) and A2.3), respectively, is determined and compared, preferably by LC-MS analysis described under item 5.7.
A4) If the amount of butyl-phosphoester of L-GA determined for A1.3) is more than the amount determined for A2.3), then the variant to be tested displays activity in Assay A.

If the amount of butyl-phosphoester of L-GA determined for A1.3) is the same or less than the amount determined for A2.3), then the variant to be tested does not display activity in Assay A.

Preferable formate solutions in steps A1.3) and A2.3) are ammonium formate or sodium formate solutions. Alternatively, the reaction in steps A 1.3) and A2.3) can also be stopped by adding methanol, preferably 1 ml of methanol.

4.3.3.3.2 Assay B

In a further assay ("Assay B"), the activity of a polypeptide variants of any of SEQ ID NO: 2, SEQ ID NO: 6, SEQ ID NO: 19, SEQ ID NO: 22, SEQ ID NO: 23, SEQ ID NO: 10, SEQ ID NO: 14, SEQ ID NO: 18, SEQ ID NO: 20, SEQ ID NO: 24, SEQ ID NO: 25, SEQ ID NO: 26, SEQ ID NO: 27, SEQ ID NO: 28, SEQ ID NO: 34, SEQ ID NO: 17, SEQ ID NO: 21, SEQ ID NO: 29, SEQ ID NO: 30, SEQ ID NO: 31, SEQ ID NO: 32, and SEQ ID NO: 33, respectively, with respect to the polypeptide may be determined.

Assay B is carried out by the following steps:
B1) First, the activity of the "standard" polypeptide standard (i.e., one polypeptide sequence selected from SEQ ID NO: 2, SEQ ID NO: 6, SEQ ID NO: 19, SEQ ID NO: 22, SEQ ID NO: 23, SEQ ID NO: 10, SEQ ID NO: 14, SEQ ID NO: 18, SEQ ID NO: 20, SEQ ID NO: 24, SEQ ID NO: 25, SEQ ID NO: 26, SEQ ID NO: 27, SEQ ID NO: 28, SEQ ID NO: 34, SEQ ID NO: 17, SEQ ID NO: 21, SEQ ID NO: 29, SEQ ID NO: 30, SEQ ID NO: 31, SEQ ID NO: 32, and SEQ ID NO: 33) is determined by the following steps B1.1), B1.2), and B1.3) as follows:
B1.1) 990 µl of a reaction solution containing phosphate buffer (0.1 M, pH 7.5), 3 mM O-acetyl L-homoserine-HCl, 10 µM pyridoxal 5-phosphate mono-hydrate and 1.0 nmol of the "standard" polypeptide to be tested are prepared and heated to 50° C.
B1.2) The reaction is started by adding 10 µl of a 200 mM solution of butyl-P-methylphosphinate (MPBE, CAS #6172-80-1). The concentration of MPBE in the reaction solution is 2 mM.
B1.3) After addition of the MPBE, the reaction is conducted for 120 minutes at 50° C. Then, the reaction is stopped by adding 10 µl 1% formate solution and cooling on ice.

B2) Then, steps B1.1), B1.2), and B1.3) are repeated with the variant: B2.1) 990 µl of a reaction solution containing phosphate buffer (0.1 M, pH 7.5), 3 mM O-acetyl L-homoserine-HCl, 10 µM pyridoxal 5-phosphate mono-hydrate and 1.0 nmol of the "variant" polypeptide to be tested are prepared and heated to 50° C.

B2.2) The reaction is started by adding 10 µl of a 200 mM solution of butyl-P-methylphosphinate (MPBE, CAS #6172-80-1). The concentration of MPBE in the reaction solution is 2 mM.

B2.3) After addition of the MPBE, the reaction is conducted for 120 minutes at 50° C. Then, the reaction is stopped by adding 10 µl 1% formate solution and cooling on ice.

B3) Finally, the amount of the butyl-phosphoester of L-GA (i.e. the compound according to formula (III) with $R^1$=n-butyl) obtained in the reaction solution in B1.3) and B2.3) is determined and compared, preferably by LC-MS analysis described under item 5.7.

B4) Then, the ratio of the amount (in mole) of butyl-phosphoester of L-GA obtained in B2.3) is divided by the amount (in mole) of butyl-phosphoester of L-GA obtained in B1.3). This ratio is then multiplied with a factor of 100, giving the relative activity of the variant polypeptide with respect to the "standard" polypeptide in percent.

Preferable formate solutions in steps B1.3) and B2.3) are ammonium formate or sodium formate solutions. Alternatively, the reaction in steps B1.3) and B2.3) can also be stopped by adding methanol, preferably 1 ml of methanol.

4.3.3.4 "Preferred Variants"

4.3.3.4.1 "Variants of SEQ ID NO: 2"

In particular, a variant of SEQ ID NO: 2 is a polypeptide with sequence identity of ≥80%, more preferably a ≥85%, more preferably a ≥90%, more preferably ≥91%, more preferably ≥92%, more preferably a ≥93%, more preferably a ≥94%, more preferably ≥95%, more preferably ≥96%, more preferably a ≥97%, more preferably a ≥98%, more preferably ≥99%, more preferably ≥99.9% sequence identity to polypeptide sequence SEQ ID NO: 2.

Preferred variants of SEQ ID NO: 2 display activity in Assay A under item 4.3.3.3.1.

Even more preferably, the activity of the respective variant of SEQ ID NO: 2 is at least 1%, preferably at least 10%, more preferably at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99% relative to the activity of SEQ ID NO: 2 as determined in Assay B under item 4.3.3.3.2.

Even more preferably, the activity of the respective variant of SEQ ID NO: 2 is in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% relative to the activity of SEQ ID NO: 2 as determined in Assay B under item 4.3.3.3.2.

4.3.3.4.2 "Variants of SEQ ID NO: 6"

In particular, a variant of SEQ ID NO: 6 is a polypeptide with sequence identity of ≥80%, more preferably a ≥85%, more preferably a ≥90%, more preferably a ≥91%, more preferably a ≥92%, more preferably a ≥93%, more preferably a ≥94%, more preferably a ≥95%, more preferably a ≥96%, more preferably a ≥97%, more preferably a ≥98%, more preferably a ≥99%, more preferably a ≥99.9% sequence identity to polypeptide sequence SEQ ID NO: 6.

Preferred variants of SEQ ID NO: 6 display activity in Assay A under item 4.3.3.3.1.

Even more preferably, the activity of the respective variant of SEQ ID NO: 6 is at least 1%, preferably at least 10%, more preferably at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99% relative to the activity of SEQ ID NO: 6 as determined in Assay B under item 4.3.3.3.2.

Even more preferably, the activity of the respective variant of SEQ ID NO: 6 is in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% relative to the activity of SEQ ID NO: 6 as determined in Assay B under item 4.3.3.3.2.

4.3.3.4.3 "Variants of SEQ ID NO: 10"

In particular, a variant of SEQ ID NO: 10 is a polypeptide with sequence identity of ≥80%, more preferably a ≥85%, more preferably a ≥90%, more preferably a ≥91%, more preferably a ≥92%, more preferably a ≥93%, more preferably a ≥94%, more preferably a ≥95%, more preferably a ≥96%, more preferably a ≥97%, more preferably a ≥98%, more preferably a ≥99%, more preferably a ≥99.9% sequence identity to polypeptide sequence SEQ ID NO: 10.

Preferred variants of SEQ ID NO: 10 show activity in Assay A under item 4.3.3.3.1.

Even more preferably, the activity of the respective variant of SEQ ID NO: 10 is at least 1%, preferably at least 10%, more preferably at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99% relative to the activity of SEQ ID NO: 10 as determined in Assay B under item 4.3.3.3.2.

Even more preferably, the activity of the respective variant of SEQ ID NO: 10 is in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% relative to the activity of SEQ ID NO: 10 as determined in Assay B under item 4.3.3.3.2.

4.3.3.4.4 "Variants of SEQ ID NO: 14"

In particular, a variant of SEQ ID NO: 14 is a polypeptide with sequence identity of ≥80%, more preferably a ≥85%, more preferably a ≥90%, more preferably a ≥91%, more preferably a ≥92%, more preferably a ≥93%, more preferably a ≥94%, more preferably a ≥95%, more preferably a ≥96%, more preferably a ≥97%, more preferably a ≥98%, more preferably a ≥99%, more preferably a ≥99.9% sequence identity to polypeptide sequence SEQ ID NO: 14.

Preferred variants of SEQ ID NO: 14 display activity in Assay A under item 4.3.3.3.1.

Even more preferably, the activity of the respective variant of SEQ ID NO: 14 is at least 1%, preferably at least 10%, more preferably at least 20%, more preferably of at least 30%, more preferably of at least 40%, more preferably of at least 50%, more preferably of at least 60%, more preferably of at least 70%, more preferably of at least 80%, more preferably of at least 90%, more preferably of at least 99% relative to the activity of SEQ ID NO: 14 as determined in Assay B under item 4.3.3.3.2.

Even more preferably, the activity of the respective variant of SEQ ID NO: 14 is in the range of 1 to 1000%, preferably in the range of 5 to 500%, more preferably in the range of 10 to 400%, more preferably in the range of 40 to 200%, more preferably in the range of 50 to 150%, more preferably in the range of 60 to 140%, more preferably in the range of 70 to 130%, more preferably in the range of 80 to 120%, more preferably in the range of 90 to 110%, more preferably 100% relative to the activity of SEQ ID NO: 14 as determined in Assay B under item 4.3.3.3.2.

4.3.3.4.5 Further Variants

Preferred variants of any of SEQ ID NO: 19, SEQ ID NO: 22, SEQ ID NO: 23, SEQ ID NO: 18, SEQ ID NO: 20, SEQ ID NO: 24, SEQ ID NO: 25, SEQ ID NO: 26, SEQ ID NO: 27, SEQ ID NO: 28, SEQ ID NO: 34, SEQ ID NO: 17, SEQ ID NO: 21, SEQ ID NO: 29, SEQ ID NO: 30, SEQ ID NO: 31, SEQ ID NO: 32, SEQ ID NO: 33, respectively, can be determined mutatis mutandis as described for SEQ ID NO: 2 as described under item 4.3.3.4.1.

Preferred variants of SEQ ID NO: 19 can be determined by the procedure that results when in the description under item 4.3.3.4.1, the word "SEQ ID NO: 2" is substituted by the word "SEQ ID NO: 19".

Preferred variants of SEQ ID NO: 22 can be determined by the procedure that results when in the description under item 4.3.3.4.1, the word "SEQ ID NO: 2" is substituted by the word "SEQ ID NO: 22".

Preferred variants of SEQ ID NO: 23 can be determined by the procedure that results when in the description under item 4.3.3.4.1, the word "SEQ ID NO: 2" is substituted by the word "SEQ ID NO: 23".

Preferred variants of SEQ ID NO: 18 can be determined by the procedure that results when in the description under item 4.3.3.4.1, the word "SEQ ID NO: 2" is substituted by the word "SEQ ID NO: 18".

Preferred variants of SEQ ID NO: 20 can be determined by the procedure that results when in the description under item 4.3.3.4.1, the word "SEQ ID NO: 2" is substituted by the word "SEQ ID NO: 20".

Preferred variants of SEQ ID NO: 24 can be determined by the procedure that results when in the description under item 4.3.3.4.1, the word "SEQ ID NO: 2" is substituted by the word "SEQ ID NO: 24".

Preferred variants of SEQ ID NO: 25 can be determined by the procedure that results when in the description under item 4.3.3.4.1, the word "SEQ ID NO: 2" is substituted by the word "SEQ ID NO: 25".

Preferred variants of SEQ ID NO: 26 can be determined by the procedure that results when in the description under item 4.3.3.4.1, the word "SEQ ID NO: 2" is substituted by the word "SEQ ID NO: 26".

Preferred variants of SEQ ID NO: 27 can be determined by the procedure that results when in the description under item 4.3.3.4.1, the word "SEQ ID NO: 2" is substituted by the word "SEQ ID NO: 27".

Preferred variants of SEQ ID NO: 28 can be determined by the procedure that results when in the description under item 4.3.3.4.1, the word "SEQ ID NO: 2" is substituted by the word "SEQ ID NO: 28".

Preferred variants of SEQ ID NO: 34 can be determined by the procedure that results when in the description under item 4.3.3.4.1, the word "SEQ ID NO: 2" is substituted by the word "SEQ ID NO: 34".

Preferred variants of SEQ ID NO: 17 can be determined by the procedure that results when in the description under item 4.3.3.4.1, the word "SEQ ID NO: 2" is substituted by the word "SEQ ID NO: 17".

Preferred variants of SEQ ID NO: 21 can be determined by the procedure that results when in the description under item 4.3.3.4.1, the word "SEQ ID NO: 2" is substituted by the word "SEQ ID NO: 21".

Preferred variants of SEQ ID NO: 29 can be determined by the procedure that results when in the description under item 4.3.3.4.1, the word "SEQ ID NO: 2" is substituted by the word "SEQ ID NO: 29".

Preferred variants of SEQ ID NO: 30 can be determined by the procedure that results when in the description under item 4.3.3.4.1, the word "SEQ ID NO: 2" is substituted by the word "SEQ ID NO: 30".

Preferred variants of SEQ ID NO: 31 can be determined by the procedure that results when in the description under item 4.3.3.4.1, the word "SEQ ID NO: 2" is substituted by the word "SEQ ID NO: 31".

Preferred variants of SEQ ID NO: 32 can be determined by the procedure that results when in the description under item 4.3.3.4.1, the word "SEQ ID NO: 2" is substituted by the word "SEQ ID NO: 32".

Preferred variants of SEQ ID NO: 33 can be determined by the procedure that results when in the description under item 4.3.3.4.1, the word "SEQ ID NO: 2" is substituted by the word "SEQ ID NO: 33".

4.4 Method Conditions

The reaction in step a) of the method according to the present invention may be carried out under conditions known to the skilled person.

The reaction medium in which activated L-homoserine $H_A$ is reacted with the substrate S is preferably aqueous, more preferably an aqueous buffer.

Exemplary buffers commonly used in biotransformation reactions and advantageously used herein include Tris, phosphate, or any of Good's buffers, such as 2-(N-morpholino) ethanesulfonic acid ("MES"), N-(2-acetamido)iminodiacetic acid ("ADA"), piperazine-N,N'-bis(2-ethanesulfonic acid) ("PIPES"), N-(2-acetamido)-2-aminoethanesulfonic acid ("ACES"), P-hydroxy-4-morpholinepropanesulfonic acid ("MOPSO"), cholamine chloride, 3-(N-morpholino) propanesulfonic acid ("MOPS"), N,N-Bis(2-hydroxyethy)-2-aminoethanesulfonic acid ("BES"), 2-[[1,3-dihydroxy-2-(hydroxymethyopropan-2-yl]amino]ethanesulfonic acid ("TES"), 4-(2-hydroxyethy)-1-piperazineethanesulfonic acid ("HEPES"), 3-(Bis(2-hydroxyethyoamino)-2-hydroxypropane-1-sulfonic acid ("DIPSO"), acetamidoglycine, 3-(N-Tris(hydroxymethyomethylamino(-2-hydroxypropane)sulfonic acid ("TAPSO"), piperazine-N,N'-bis(2-hydroxypropanesulfonic acid) ("POPSO"), 4-(2-Hydroxyethyopiperazine-1-(2-hydroxypropanesulfonic acid)

("HEPPSO"), 3-[4-(2-HydroxyethyD)-1-piperazinyl]propanesulfonic acid ("HEPPS"), tricine, glycinamide, bicine, or 3-[[1,3-dihydroxy-2-(hydroxymethylpropan-2-yl]amino] propane-1-sulfonic acid ("TAPS").

In some embodiments, ammonium can act as a buffer. One or more organic solvents can also be added to the reaction.

Preferably, step a) of the method according to the invention is carried out in a phosphate buffer.

The pH of the reaction medium in step a) of the method is preferably in the range of from 2 to 10, more preferably in the range of from 5 to 8, most preferably 7.5.

The method according to the invention is preferably carried out at a temperature in the range of from 20° C. to 70° C., more preferably in the range of from 30° C. to 55° C., most preferably 50° C.

4.5 L-Glufosinate Phosphoester

The product of the method according to the invention, is a compound of the following structure (III):

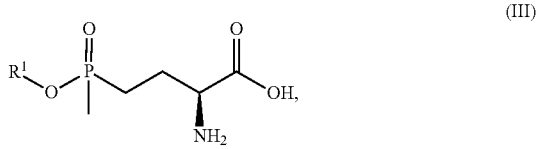

(III)

The compound according to structure (III) is L-glufosinate (for $R^1$=H) or L-glufosinate phosphoester (for $R^1$=alkyl, alkenyl, alkinyl, hydroxyalkyl or aryl).

The compound according to structure (III), wherein $R^1$=n-butyl, is abbreviated as "L-GA-Bu" or "LGA-Bu".

The skilled person understands that the identity of residue $R^1$ in the compound according to structure (III) depends on the identity of residue $R^1$ in the substrate structure (I).

If $R^1$ is hydrogen, L-glufosinate is directly obtained in the method according to the invention.

In the preferred embodiment, in which $R^1$ is selected from alkyl, alkenyl, alkinyl, hydroxyalkyl, aryl, preferably alkyl, more preferably methyl, ethyl, n-butyl, the compound (III) is a L-glufosinate phosphoester.

In those embodiments, it is further preferable that the method according to the invention contains a further step b) wherein the compound of the structure (III) which is obtained in step (a), and in which $R^1$ is selected from alkyl, alkenyl, alkinyl, hydroxyalkyl, aryl, preferably alkyl, more preferably methyl, ethyl, n-butyl, is saponified to give L-glufosinate.

This can be carried out by methods known to the skilled person.

Preferably, such saponification is carried out under acidic conditions, more preferably by mixing 1 Volume of the reaction medium containing the compound of the structure (III) which is obtained in step (a) and 4 Volumes of 6N HCl for 2 h and incubating the resulting mixture at a temperature of 50° C. to 150° C., preferably at 100° C.

Alternatively, an enzymatic saponification can be carried out.

5. EXAMPLES

Genes of different origin encoding sulfhydrylase (EC 2.5.1.- and EC 2.5.1.49) were tested for their ability to react with an activated homoserine derivate and different substrates according to structure (I) to form a glufosinate derivate.

5.1 Example 1 Identification of Suitable Enzymes and Construction of Plasmids

5.1.1 Examined Sulfhydrylase

Bibliographic details of the genes of O-acetylhomoserine sulfhydrylases and O-succinylhomoserine sulfhydrylases that were used in the examples are summarized in table 2.

TABLE 2

| Strain | comment | Gene name | Gene ID | ReferenceNCBI accession | SEQ ID NO: |
|---|---|---|---|---|---|
| Corynebacterium glutamicum ATCC 13032 | wild type | metY | NCgl0625 | NC_003450 | 1 |
| Corynebacterium glutamicum ATCC 13032 | metY variant | metY_P2T | | | 5 |
| Chromobacterium violaceum ATCC 12472 | wild type | metZ | CV_2725 | AE016825 | 9 |
| Hyphomonas neptunium ATCC 15444 | wild type | metZ | HNE_2672 | CP000158 | 13 |

5.1.2 Preparation of the Gene Expression Plasmids

5.1.2.1 O-acetylhomoserine sulfhydrylase metY derived from *Corynebacterium glutamicum*

The metY gene derived from *Corynebacterium glutamicum* ATCC 13032 codes for an O-acetylhomoserine sulfhydrylase and can be found at the NCBI under locus tag NCgl0625 of the genome sequence accessible under NC_003450.

To realize the expression of the enzyme, the expression vector pET-26b(+) (Novagen EMD Millipore) was used. Therefore, the metY_Cg polynucleotide according to SEQ ID NO: 3 was synthesized by GeneArt (ThermoFisher Scientific (Waltham, USA)).

To assemble the expression vector pET-26b(+)_metY-Cg, the vector pET-26(+) and the metY_Cg polynucleotide were both treated with NdeI and NotI, ligated, and the ligation mixture was used to transform *E. coli*. The resulting vector, pET-26b(+)_metY-Cg, is shown schematically in FIG. 1. DNA of the expression vector pET-26b(+)_metY-Cg was isolated from a transformant.

5.1.2.2 O-acetylhomoserine sulfhydrylase metY_P2T derived from *Corynebacterium glutamicum*

The O-acetylhomoserine sulfhydrylase variant metY_P2T is encoded by a polynucleotide according to SEQ ID NO: 5, which is identical to the polynucleotide of SEQ ID NO: 1, except that the nucleobases from position 4 to 6 are aca.

The polynucleotide of SEQ ID NO: 5 encodes a polypeptide comprising the amino acid sequence of SEQ ID NO: 6, which is identical to the polynucleotide of SEQ ID NO: 1, except that the amino acid proline at position 2 is substituted by threonine.

To realize the expression of the enzyme variant metY_P2T, the expression vector pET-26b(+) (Novagen EMD Millipore) was used. Therefore, the metY_P2T polynucleotide according to SEQ ID NO: 7 was synthesized by GeneArt (ThermoFisher Scientific (Waltham, USA)).

To assemble the expression vector pET-26b(+)_metY_P2T, the vector pET-26(+) and the metY_P2T polynucleotide were both treated with NdeI and NotI, ligated, and the ligation mixture was used to transform *E. coli*. The resulting vector, pET-26b(+)_metY_P2T, is shown schematically in FIG. 2.

DNA of the expression vector pET-26b(+)_metY_P2T was isolated from a transformant.

5.1.2.3 O-succinylhomoserine sulfhydrylase metZ derived from *Chromobacterium violaceaum*

The metZ gene derived from *Chromobacterium violaceaum* ATCC 12472 codes for an O-succinylhomoserine sulfhydrylase and can be found at the NCBI under locus tag CV_2725 of the genome sequence accessible under AE016825.

To realize the expression of the enzyme, the expression vector pET-26b(+) (Novagen EMD Millipore) was used. Therefore, the metZ_Cv polynucleotide according to SEQ ID NO: 11 was synthesized by GeneArt (ThermoFisher Scientific (Waltham, USA)).

To assemble the expression vector pET-26b(+)_metZ-Cv the vector pET-26(+) and the metZ_Cv polynucleotide were both treated with NdeI and XhoI, ligated, and the ligation mixture was used to transform *E. coli*. The resulting vector, pET-26b(+)_metZ-Cv, is shown schematically in FIG. 3. DNA of the expression vector pET-26b(+)_metZ-Cv was isolated from a transformant.

5.1.2.4 O-succinylhomoserine sulfhydrylase metZ derived from *Hyphomonas neptunium*

The metZ gene derived from *Hyphomonas neptunium* ATCC 15444 codes for an O-succinylhomoserine sulfhydrylase and can be found at the NCBI under locus tag HNE_2672 of the genome sequence accessible under CP000158.

To realize the expression of the enzyme, the expression vector pET-26b(+) (Novagen EMD Millipore) was used. Therefore, the metZ_Hn polynucleotide according to SEQ ID NO: 15 was synthesized by GeneArt (ThermoFisher Scientific (Waltham, USA)).

To assemble the expression vector pET-26b(+)_metZ-Hn, the vector pET-26(+) and the metZ_Hn polynucleotide were both treated with XbaI and XhoI, ligated, and the ligation mixture was used to transform *E. coli*. The resulting vector, pET-26b(+)_metZ-Hn, is shown schematically in FIG. 4.

DNA of the expression vector pET-26b(+)_metZ-Hn was isolated from a transformant.

5.2 Transforming and Expression of the Sulfhydrylase

These vectors carrying the sulfhydrylases genes were each transformed in *Escherichia coli* BL21 (DE3) (New England Biolabs), which were subsequently cultured on LB medium agar plates with 50 mg/l kanamycin at 37° C. for 16 h. Strain BL21 carrying the vector pET26b(+) without any insert was used as negative control.

The resulting strain were named Ec BL21 pET-26b(+)_metY-Cg, Ec BL21 pET-26b(+)_metY-Cg_P2T, Ec BL21 pET-26b(+)_metZ-Cv, Ec BL21 pET-26b(+)_metZ-Hn and Ec BL21 pET-26b(+) respectively.

In each case a colony has been selected which was inoculated into 10 ml of LB medium with 50 mg/l kanamycin and cultured at 37° C., 250 rpm for 6 hours. 50 µl of LB medium were subsequently treated with 50 mg/l kanamycin and inoculated with 50 µl of the growth cell culture and incubated at 28° C., 250 rpm for 16 h. This cell culture was diluted with 200 mi of fresh LB medium containing 50 µg/l kanamycin in a 2 l flask to an OD of 0.15 and was further cultured under identical conditions until an OD of 0.5 was attained (circa 4 h). The start point of the induction of gene expression was then affected by adding 200 µl of a 300 mM IPTG stock solution (final concentration 300 µM isopropyl-β-D-thiogalactopyranoside (IPTG), Sigma-Aldrich, Germany). The induction was carried out at 28° C., 250 rpm for 4 h. The culture was then harvested (8 ml normalised to an OD=1), the supernatant removed by centrifugation (20 min, 4000 rpm, 4° C.) and the pelleted cells were washed twice with 800 µl of 0.1 M potassium phosphate buffer (pH 7.5) and taken up in 1 mi of buffer. The mechanical cell digestion was carried out in a FastPrep FP120 instrument (QBiogene, Heidelberg), wherein the cells were shaken four times for 30 s at 6.5 m/s in digestion vessels with 300 mg of glass beads (Ø0.2-0.3 mm). The crude extract was then centrifuged at 12000 rpm, 4° C., 20 min, in order to remove undigested cells and cell debris. The supernatant was used for the enzyme assay. The concentration of the polypeptide in the supernatant was determined by SDS page and analysis of the respective bands via the software GelQuant® (BiochemLab-Solutions).

5.3 Inventive Examples I1 to I4

The following assay was carried out to determine whether the respective polypeptide catalyzed the reaction of the respective phosphor-containing substrate and activated L-homoserine. O-acetyl L-homoserine was used as activated L-homoserine substrate.

To 880 µl phosphate buffer (0.1 M, pH 7.5) containing 1 nmol of the polypeptide to be tested were added 100 µl of a 30 mM aqueous solution of 0-acetyl homoserine-HCl, 10 µl of a 1 mM aqueous solution of pyridoxal 5'-phosphate mono-hydrate (1 mM), and 10 µl of a 200 mM aqueous solution of Butyl P-methylphosphinate (CAS-No. 6172-80-1; "MPBE"). The reaction was conducted for 120 min at 50°

C. Then, 100 µl batch solution was diluted in 100 µl methanol and applied on the LC-MS QQQ (item 5.7) to analyse the LGA-Bu.

5.4 Inventive Examole I5

Catalysis of the polypeptide isolated from pET-26b(+)_metY-Cg_P2T was further tested in a reaction with methyl P-methylphosphinate ("MPME"; CAS-No. 16391-06-3).

To 880 µl phosphate buffer (0.1 M, pH 7.5) containing 1 nmol of this polypeptide were added 100 µl of a 30 mM aqueous solution of 0-acetyl homoserine-HCl, 10 µl of a 1 mM aqueous solution of pyridoxal 5'-phosphate mono-hydrate (1 mM), and 10 µl of a 200 mM aqueous solution of MPME. The reaction was conducted for 120 min at 50° C. Then, 100 µl batch solution was diluted in 100 µl methanol and applied on the LC-MS QQQ (item 5.7) to analyse the LGA-Bu.

5.4 Comparative Examples C1 to C4

It was further investigated whether other phosphor compounds would serve as substrates for the above reaction. To this end, diethyl methylphosphonite ("DEMP"; CAS-No. 15715-41-0) was tested.

To 880 µl phosphate buffer (0.1 M, pH 7.5) containing 1 nmol of the polypeptide to be tested were added 100 µl of a 30 mM aqueous solution of 0-acetyl homoserine-HCl, 10 µl of a 1 mM aqueous solution of pyridoxal 5'-phosphate mono-hydrate (1 mM), and 10 µl of a 200 mM aqueous solution of DEMP. The reaction was conducted for 120 min at 50° C. Then, 100 µl batch solution was diluted in 100 µl methanol and applied on the LC-MS QQQ (item 5.7) to analyse the LGA-Bu.

5.5 Comparative Examples C5 to C8

It was further investigated whether the respective polypeptide would catalyze the wild type reaction of O-acetyl-homoserine with methylmercaptane ("MM"; CAS-No. 74-93-1) according to the above reaction <1A>.

To 880 µl phosphate buffer (0.1 M, pH 7.5) containing 1 nmol of the polypeptide to be tested were added 100 µl of a 30 mM aqueous solution of 0-acetyl homoserine-HCl, 10 µl of a 1 mM aqueous solution of pyridoxal 5'-phosphate mono-hydrate (1 mM), and 10 µl of a 200 mM aqueous solution of MM. The reaction was conducted for 120 min at 50° C. Then, 100 µl batch solution was diluted 40 in 100 µl methanol and applied on the LC-MS QQQ (item 5.7) to analyse for the respective product.

In case of inventive examples 11 to 14, the product is the compound according to structure (III), wherein $R^1$=n-butyl ("LGA-Bu").

In case of inventive example 15, the product is the compound according to structure (III), wherein $R^1$=methyl.

In case of comparative examples C1 to C4, the product is the compound according to structure (III), wherein $R^1$=ethyl ("LGA-Et").

In case of comparative examples C5 to C6, the product is methionine.

The results are summarized in the following table 3. The abbreviations used are

"DEMP"=methyl diethoxy phosphine (CAS-No. 15715-41-0);
"MPBE"=butyl P-methylphosphinate (CAS-No. 6172-80-1);
"MPME"=methyl P-methylphosphinate (CAS-No. 16391-06-3);
"MM"=methyl mercaptane (CAS-No: 74-93-1).

TABLE 3

| Example | Enzyme | Polypeptide | Substrate | Product |
|---|---|---|---|---|
| I1 | Cg_MetY | SEQ ID NO: 2 | MPBE | yes |
| I2 | Cg_MetY_P2T | SEQ ID NO: 6 | MPBE | yes |
| I3 | Cv_MetZ | SEQ ID NO: 10 | MPBE | yes |
| I4 | Hn_MetZ | SEQ ID NO: 14 | MPBE | yes |
| I5 | Cg_MetY_P2T | SEQ ID NO: 6 | MPME | yes |
| C1 | Cg_MetY | SEQ ID NO: 2 | DEMP | no |
| C2 | Cg_MetY_P2T | SEQ ID NO: 6 | DEMP | no |
| C3 | Cv_MetZ | SEQ ID NO: 10 | DEMP | no |
| C4 | Hn_MetZ | SEQ ID NO: 14 | DEMP | no |
| C5 | Cg_MetY | SEQ ID NO: 2 | MM | yes |
| C6 | Cg_MetY_P2T | SEQ ID NO: 6 | MM | yes |
| C7 | Cv_MetZ | SEQ ID NO: 10 | MM | yes |
| C8 | Hn_MetZ | SEQ ID NO: 14 | MM | yes |

5.6 Results

The results summarized in table 3 surprisingly show that the tested polypeptides accept other substrates methylphosphinic acid compounds such as MPBE and MPME, and catalyze their reaction with activated L-homoserine to the respective n-butyl or methyl phosphate ester of LGA. This finding was even more surprising, as the skilled person would not have expected that these enzyme would catalyze these reactions, as other phosphate compounds such as DEMP do not work as substrates.

This finding opens new enzymatic pathways to LGA and its derivatives.

5.7 Analytical Methods

All analytical measurements for the experiments have been carried out via a scan on a LC-MS QQQ system. Samples were diluted in in methanol (v:v=1:2).

The applied HPLC belongs to the 1260 Infinity-series from Agilent connected to a mass spectrometer 6420 triple quadrupole with electrospray ionization. Peak identification was carried out via retention time and molecular mass in a positive detection mode.

Data evaluation was carried out via peak area and a quadratic calibration without zero.

Acquisition Method Details

Ion Source ESI (electrospray ionization)

Time Parameters

Mass Range m/z=50-300
Scans per second 400
Fragmentation 40 V
Polarity Positive (Scan-Mode)

Source Parameters

Gas temperature 350° C.
Gas flow 12 l/min
Nebulizer 50 psi
Capillary 4000 V

Binary Pump

Injection Volume 2.00 μL
Flow 0.60 mL/min
Solvent Composition
Solvent A 100 mM Ammonium acetate plus 0.1% (v/v) formic acid in H$_2$O
Solvent B 0.1% formic acid in acetonitrile
Gradient see table 4.

TABLE 4

| Time (min) | Solvent A (%) | Solvent B (%) |
|---|---|---|
| 0.5 | 5 | 95 |
| 1.2 | 45 | 55 |
| 4.0 | 45 | 55 |
| 4.1 | 95 | 5 |
| 7.0 | 95 | 5 |
| 7.1 | 5 | 95 |
| 10.0 | 5 | 95 |

Column

Type Luna HILIC; 100×2 mm; 3 μm; Phenomenex 00D-4449-BO
Temperature 30.0° C.

6. SEQUENCE OVERVIEW

The following table provides an overview of the DNA and protein sequences referred to in the context of the present application:

Abbreviations used are: "AHS"=-acetylhomoserine sulfhydrylase; "SHS"=O-succinylhomoserine sulfhydrylase; "CGS"=cystathionine γ-synthase.

| SEQ ID NO: | |
|---|---|
| 1 | DNA sequence of metY gene (nucleotide sequence comprising locus_tag NCgl0625 disclosed in NC_003450) from *Corynebacterium glutamicum* ATCC 13032, encoding AHS. |
| 2 | Protein sequence translated from SEQ ID NO: 1. |
| 3 | DNA sequence: nucleotides 7 to 1320 are identical with SEQ ID NO: 1, further containing six additional nucleotides (aaacat) at position 1 to 6, thus forming a Ndel restriction site (nucleotides 4 to 9), and ten additional nucleotides at 1321-1330 (gcggccgcaaa), forming a Notl restriction site (nucleotides 1321-1328). |
| 4 | Protein sequence translated from nucleotides 7 to 1320 of SEQ ID NO: 3; identical with SEQ ID NO: 2. |
| 5 | DNA sequence identical to SEQ ID NO: 1, except for one allelic variation [cca (for Pro)→ aca (for Thr)] at nucleotides 4-6. "metY_P2T"-variant of AHS |
| 6 | Protein sequence translated from SEQ ID NO: 5 (99.8% sequence identity with SEQ ID NO: 2). |
| 7 | DNA sequence: nucleotides 7 to 1320 are identical with SEQ ID NO: 5, further containing six additional nucleotides (aaacat) at position 1 to 6, thus forming a Ndel restriction site (nucleotdies 4 to 9), and ten additional nucleotides at 1321-1330 (gcggccgcaaa), forming a Notl restriction site. |
| 8 | Protein sequence translated from nucleotides 7 to 1320 of SEQ ID NO: 7; identical with SEQ ID NO: 6. |
| 9 | DNA sequence of metZ gene (nucleotide sequence comprising locus_tag CV_2725 disclosed in AE016825) from *Chromobacterium violaceum* ATCC 12472, encoding SHS. |
| 10 | Protein sequence translated from SEQ ID NO: 9. |
| 11 | DNA sequence: nucleotides 7 to 1191 are identical with SEQ ID NO: 9, further containing six additional nucleotides (aaacat) at position 1 to 6, thus forming a Ndel restriction site (nucleotides 4 to 9), and nine additional nucleotides at positions 1192-1200 (ctcgagaaa), forming a Xhol restriction site (nucleotides 1192-1197). |
| 12 | Protein sequence translated from nucleotides 7 to 1191 of SEQ ID NO: 9; identical with SEQ ID NO: 10. |
| 13 | DNA sequence of metZ gene (nucleotide sequence comprising locus_tag HNE_2672 disclosed in CP000158) from *Hyphomonas neptunium* ATCC 15444, encoding SHS. |
| 14 | Protein sequence translated from SEQ ID NO: 13. |
| 15 | DNA sequence: nucleotides 46 to 1245 are identical with SEQ ID NO: 13, further containing 45 additional nucleotides (aaatctagaa ataattttgt ttaactttaa gaaggagata tacat) at position 1 to 45, thus forming a Xbal restriction site (nucleotides 4 to 9), and nine additional nucleotides at positions 1246-1254 (ctcgagaaa), forming a Xhol restriction site (nucleotides 1246-1251). |
| 16 | Protein sequence translated from nucleotides 46 to 1245 of SEQ ID NO: 13; identical with SEQ ID NO: 14. |
| 17 | Protein sequence of metB-gene from *Escherichia coli* K-12, encoding CGS. |
| 18 | Protein sequence of metZ-gene from *Pseudomonas aeruginosa* PAO1, encoding SHS. |
| 19 | Protein sequence of metY-gene from *Pseudomonas aeruginosa* PAO1, encoding AHS. |
| 20 | Protein sequence of metZ-gene from *Pseudomonas putida* KT2440, encoding SHS. |
| 21 | Protein sequence of metB-gene from *Corynebacterium glutamicum* ATCC 13032, encoding CGS. |
| 22 | Protein sequence of met17 gene from *Leptospira interrogans* serovar *Lai* str. 56601, encoding AHS. |
| 23 | Protein sequence of Met17 gene from *Saccharomyces cerevisiae* S288c, encoding AHS. |
| 24 | Protein sequence of metZ-gene from *Nocardia farcinica* IFM 10152, encoding SHS. |
| 25 | Protein sequence of metZ-gene from *Bradyrhizobium japonicum* USDA 6, encoding SHS. |
| 26 | Protein sequence of metZ-gene from *Methylococcus capsulatus* str. Bath, encoding SHS. |
| 27 | Protein sequence from *Methylobacillus flagellatus* KT, encoding an SHS, therefore abbreviated herein as "metZ". |
| 28 | Protein sequence of metZ-gene from *Nitrosomonas europaea* ATCC 19718, encoding SHS. |
| 29 | Protein sequence of metB-gene from *Klebsiella pneumoniae* subsp. *pneumoniae* MGH 78578, encoding CGS. |
| 30 | Protein sequence of metI-gene from *Bacillus subtilis* subsp. *subtilis* str. 168, encoding CGS. |
| 31 | Protein sequence of metB-gene from *Shigella flexneri* 2a str. 2457T, encoding CGS. |
| 32 | Protein sequence of metB-gene from *Colwellia psychrerythraea* 34H, encoding CGS. |
| 33 | Protein sequence of metB-gene from *Salmonella enterica* serovar *Paratyphi* A ATCC 9150, encoding CGS. |
| 34 | Protein sequence of metZ-gene from *Rhodobacter sphaeroides* ATCC 17029, encoding SHS. |

The invention claimed is:

1. An enzymatically catalyzed method for producing L-glufosinate or a phosphoester thereof, the method comprising:

reacting an activated L-homoserine $H_A$ with a substrate S of the following structure (I) to produce a compound of the following structure (III),

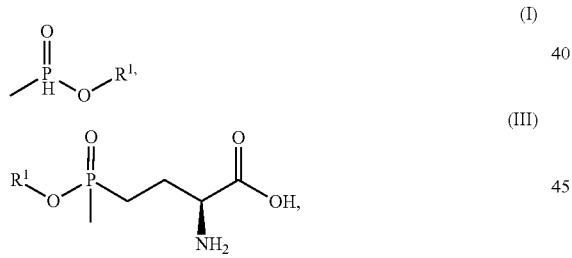

wherein $R^1$ is selected from the group consisting of hydrogen, an alkyl, an alkenyl, an alkinyl, a hydroxyalkyl, and an aryl, and wherein the activated L-homoserine HA has the following structure (II):

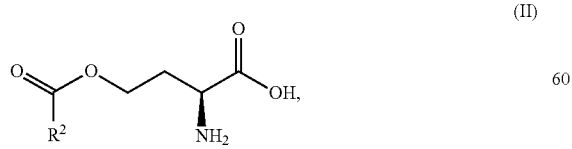

wherein $R^2$ is a hydrocarbon group with 1 to 15 carbon atoms which optionally comprises at least one functional group selected from OH, COOH, NH, and wherein the reaction is catalyzed by at least one enzyme selected from the group consisting of a sulfhydrylase and a cystathionine γ-synthase, wherein the sulfhydrylase comprises a polypeptide sequence selected from the group consisting of SEQ ID NO: 2 and variants of SEQ ID NO: 2, SEQ ID NO: 6 and variants of SEQ ID NO: 6, SEQ ID NO: 19 and variants of SEQ ID NO: 19, SEQ ID NO: 22 and variants of SEQ ID NO: 22, SEQ ID NO: 23 and variants of SEQ ID NO: 23, SEQ ID NO: 10 and variants of SEQ ID NO: 10, SEQ ID NO: 14 and variants of SEQ ID NO: 14, SEQ ID NO: 18 and variants of SEQ ID NO: 18, SEQ ID NO: 20 and variants of SEQ ID NO: 20, SEQ ID NO: 24 and variants of SEQ ID NO: 24, SEQ ID NO: 25 and variants of SEQ ID NO: 25, SEQ ID NO: 26 and variants of SEQ ID NO: 26, SEQ ID NO: 27 and variants of SEQ ID NO: 27, SEQ ID NO: 28 and variants of SEQ ID NO: 28, and SEQ ID NO: 34 and variants of SEQ ID NO: 34, wherein the variants of SEQ ID NOs: 2, 6, 10, 14, 18-20, 22-28, and 34 are defined as polypeptide sequences with at least 95% sequence identity to SEQ ID NOs: 2, 6, 10, 14, 18-20, 22-28, and 34 respectively, and wherein the cystathionine γ-synthase comprises a polypeptide sequence selected from the group consisting of SEQ ID NO: 17 and variants of SEQ ID NO: 17, SEQ ID NO: 21 and variants of SEQ ID NO: 21, SEQ ID NO: 29 and variants of SEQ ID NO: 29, SEQ ID NO: 30 and variants of SEQ ID NO: 30, SEQ ID NO: 31 and variants of SEQ ID NO: 31, SEQ ID NO: 32 and variants of SEQ ID NO: 32, and SEQ ID NO: 33 and variants of SEQ ID NO: 33, wherein the variants of SEQ ID NOs: 17, 21, and 29-33 are defined as polypeptide sequences with at least 95% sequence identity to SEQ ID NOs: 17, 21, and 29-33 respectively.

2. The method according to claim 1, wherein the activated L-homoserine $H_A$ is selected from the group consisting of O-succinyl-L-homoserine and O-acetyl-L-homoserine.

3. The method according to claim 2, wherein the activated L-homoserine $H_A$ is O-acetyl-L-homoserine.

4. The method according to claim 1, wherein $R^1$ is selected from the group consisting of hydrogen and an alkyl group.

5. The method according to claim 4, wherein the alkyl group is selected from the group consisting of methyl, ethyl, and n-butyl.

6. The method according to claim 1, wherein $R^1$ is selected from the group consisting of an alkyl, an alkenyl, an alkinyl, a hydroxyalkyl, and an aryl, further comprising saponifying the compound of the structure (III) obtained in the reaction to give L-glufosinate.

7. The method according to claim 1, wherein the reaction is catalyzed by the sulfhydrylase.

8. The method according to claim 7, wherein the sulfhydrylase is an O-acetyl homoserine sulfhydrylase or an O-succinyl homoserine sulfhydrylase.

9. The method according to claim 1, wherein the activated L-homoserine $H_A$ is prepared by fermentation of a strain producing activated L-homoserine $H_A$.

10. The method according to claim 9, wherein the strain producing activated L-homoserine $H_A$ is selected from the group consisting of *Escherichia* sp., *Erwinia* sp., *Serratia* sp., *Providencia* sp., *Corynebacterium* sp., *Pseudomonas* sp., Leptospira sp., Salmonella sp., Brevibacterium sp., Hypomononas sp., Chromobacterium sp., and *Norcardia* sp., fungi.

11. The method according to claim 1, wherein $R^2$ is a hydrocarbon group with 1 to 15 carbon atoms comprising at least one functional group selected from the group consisting of OH, COOH, and NH.

\* \* \* \* \*